(12) United States Patent
Allen et al.

(10) Patent No.: US 11,338,107 B2
(45) Date of Patent: May 24, 2022

(54) SYSTEMS, METHODS AND ARTICLES FOR ENHANCING WELLNESS ASSOCIATED WITH HABITABLE ENVIRONMENTS

(71) Applicant: Delos Living LLC, New York, NY (US)

(72) Inventors: Samantha Kinko Allen, Hong Kong (CN); Trevor Starin Granger, New York, NY (US); Max Andrew Pollinger, New York, NY (US); Regina Vaicekonyte-Peters, Seattle, WA (US); Jie Zhao, Hoboken, NJ (US)

(73) Assignee: Delos Living LLC, New York, NY (US)

( * ) Notice: Subject to any disclaimer, the term of this patent is extended or adjusted under 35 U.S.C. 154(b) by 0 days.

(21) Appl. No.: 16/327,650

(22) PCT Filed: Aug. 24, 2017

(86) PCT No.: PCT/US2017/048382
§ 371 (c)(1),
(2) Date: Feb. 22, 2019

(87) PCT Pub. No.: WO2018/039433
PCT Pub. Date: Mar. 1, 2018

(65) Prior Publication Data
US 2019/0209806 A1   Jul. 11, 2019

Related U.S. Application Data

(60) Provisional application No. 62/379,086, filed on Aug. 24, 2016, provisional application No. 62/379,079, filed on Aug. 24, 2016.

(51) Int. Cl.
*A61M 21/02* (2006.01)
*A61M 21/00* (2006.01)
(Continued)

(52) U.S. Cl.
CPC ........ *A61M 21/02* (2013.01); *A61M 21/0094* (2013.01); *G05B 15/02* (2013.01);
(Continued)

(58) Field of Classification Search
CPC .............. A61M 21/02; A61M 21/0094; A61M 2230/04; A61M 2021/0011;
(Continued)

(56) References Cited

U.S. PATENT DOCUMENTS

| 628,351 A | 7/1899 | O'Neill |
| 828,733 A | 8/1906 | Fuller |

(Continued)

FOREIGN PATENT DOCUMENTS

| CA | 2307458 | 11/2001 |
| CA | 2740939 | 3/2010 |

(Continued)

OTHER PUBLICATIONS

International Search Report for PCT/US2017/048382 dated Jan. 4, 2018 (4 pages).
(Continued)

*Primary Examiner* — Charles R Kasenge
(74) *Attorney, Agent, or Firm* — Fitch, Even, Tabin & Flannery LLP

(57) ABSTRACT

Environmental characteristics or scenes of habitable environments (e.g., hotel or motel rooms, spas, resorts, cruise boat cabins, offices, hospitals and/or homes, apartments or residences, or other spaces or sub-spaces) are controlled to facilitate certain activities of a user in the environment by increasing focus, preparing for sleep, directing movement, masking ambient noise, and improving air quality, among others. Controllable characteristics include, for example, lighting, $CO_2/O_2$ levels, humidity levels, sound, aroma, and air temperature. Controls are provided for the occupant (Continued)

and/or facility personnel to select activities or scenes, or sensors detect the activity and implement an appropriate scene.

25 Claims, 17 Drawing Sheets

(51) Int. Cl.

| | | |
|---|---|---|
| H04L 12/28 | (2006.01) | |
| G16H 20/70 | (2018.01) | |
| G05B 15/02 | (2006.01) | |
| G16H 20/30 | (2018.01) | |
| H05B 47/11 | (2020.01) | |
| H05B 47/10 | (2020.01) | |
| F24F 11/00 | (2018.01) | |
| F24F 3/12 | (2006.01) | |
| A61N 5/06 | (2006.01) | |
| F24F 120/10 | (2018.01) | |
| A61M 16/16 | (2006.01) | |
| F24F 8/50 | (2021.01) | |
| G08C 23/04 | (2006.01) | |

(52) U.S. Cl.
CPC ............. *G16H 20/30* (2018.01); *G16H 20/70* (2018.01); *H04L 12/282* (2013.01); *H04L 12/2829* (2013.01); *H05B 47/10* (2020.01); *H05B 47/11* (2020.01); *A61M 16/161* (2014.02); *A61M 2021/0011* (2013.01); *A61M 2021/0016* (2013.01); *A61M 2021/0022* (2013.01); *A61M 2021/0027* (2013.01); *A61M 2021/0044* (2013.01); *A61M 2021/0066* (2013.01); *A61M 2205/0205* (2013.01); *A61M 2205/0238* (2013.01); *A61M 2205/3303* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/42* (2013.01); *A61M 2205/50* (2013.01); *A61M 2205/505* (2013.01); *A61M 2205/6018* (2013.01); *A61M 2205/6054* (2013.01); *A61M 2205/7509* (2013.01); *A61M 2205/7518* (2013.01); *A61M 2205/7545* (2013.01); *A61M 2230/04* (2013.01); *A61M 2230/50* (2013.01); *A61M 2230/63* (2013.01); *A61N 5/0618* (2013.01); *A61N 2005/0626* (2013.01); *F24F 3/12* (2013.01); *F24F 8/50* (2021.01); *F24F 11/0008* (2013.01); *F24F 2120/10* (2018.01); *G05B 2219/2642* (2013.01); *G08C 23/04* (2013.01)

(58) Field of Classification Search
CPC ........ A61M 2021/0022; A61M 16/161; A61M 2230/63; A61M 2205/50; A61M 2230/50; A61M 2205/3303; A61M 2205/7545; A61M 2205/7518; A61M 2205/7509; A61M 2205/6054; A61M 2205/6018; A61M 2205/505; A61M 2205/42; A61M 2205/3592; A61M 2205/3584; A61M 2205/3561; A61M 2205/3553; A61M 2205/3368; A61M 2205/0238; A61M 2205/0205; A61M 2021/0066; A61M 2021/0044; A61M 2021/0027; A61M 2021/0016; H05B 47/11; H05B 47/10; H04L 12/2829; H04L 12/282; G16H 20/30; G16H 20/70; G05B 15/02; G05B 2219/2642; F24F 2120/10; F24F 2003/1689; F24F 3/12; F24F 11/0008; A61N 2005/0626; A61N 5/0618; G08C 23/04
See application file for complete search history.

(56) References Cited

U.S. PATENT DOCUMENTS

| | | |
|---|---|---|
| 853,033 A | 5/1907 | Roberts |
| 1,648,277 A | 11/1927 | Korb |
| 2,184,644 A | 12/1939 | Homberger |
| RE27,027 E | 1/1971 | Cristofv |
| 3,621,838 A | 11/1971 | Harding |
| 3,678,337 A | 7/1972 | Grauvogel |
| 4,074,124 A | 2/1978 | Maute |
| 4,273,999 A | 6/1981 | Pierpoint |
| 4,308,911 A | 1/1982 | Mandl |
| 4,638,853 A | 1/1987 | Papak |
| D295,934 S | 5/1988 | Dyrhood |
| 4,803,625 A | 2/1989 | Fu |
| 4,828,609 A | 5/1989 | Anderson |
| 4,858,609 A | 8/1989 | Cole |
| 4,882,166 A | 11/1989 | Graham |
| 4,893,291 A | 1/1990 | Bick |
| 4,911,166 A | 3/1990 | Leighton |
| 4,911,737 A | 3/1990 | Yehl |
| 4,916,642 A | 4/1990 | Kaiser |
| 4,930,505 A | 6/1990 | Hatje |
| 4,938,582 A | 7/1990 | Leslie |
| 4,947,928 A | 8/1990 | Parker |
| 4,953,784 A | 9/1990 | Yasufuku |
| 4,962,687 A | 10/1990 | Belliveau |
| D312,018 S | 11/1990 | Giesy |
| 5,006,985 A | 4/1991 | Ehret |
| 5,010,777 A | 4/1991 | Yehl |
| 5,043,840 A | 8/1991 | Yehl |
| 5,079,682 A | 1/1992 | Roberts |
| 5,082,173 A | 1/1992 | Poehlman |
| 5,086,385 A | 2/1992 | Launey |
| 5,092,669 A | 3/1992 | Anderson |
| 5,103,391 A | 4/1992 | Barrett |
| 5,121,030 A | 6/1992 | Schott |
| 5,176,133 A | 1/1993 | Czeisler |
| 5,193,900 A | 3/1993 | Yano |
| 5,197,941 A | 3/1993 | Whitaker |
| 5,214,736 A | 5/1993 | Uemiya |
| D335,978 S | 6/1993 | Grahn |
| 5,250,799 A | 10/1993 | Werner |
| 5,259,553 A | 11/1993 | Shyu |
| 5,285,356 A | 2/1994 | Skene |
| D345,071 S | 3/1994 | Gould |
| 5,292,345 A | 3/1994 | Gerardo |
| 5,304,212 A | 4/1994 | Czeisler |
| 5,343,121 A | 8/1994 | Terman |
| 5,344,068 A | 9/1994 | Haessig |
| 5,350,977 A | 9/1994 | Hamamoto |
| 5,357,170 A | 10/1994 | Luchaco |
| 5,395,042 A | 3/1995 | Riley |
| 5,433,923 A | 7/1995 | Wolverton |
| 5,462,485 A | 10/1995 | Kinkead |
| D364,762 S | 12/1995 | Compton |
| D365,484 S | 12/1995 | Trattner, Jr. |
| 5,473,537 A | 12/1995 | Glazer |
| 5,503,637 A | 4/1996 | Kyricos |
| 5,545,192 A | 8/1996 | Czeisler |
| 5,589,741 A | 12/1996 | Terman |
| 5,692,501 A | 12/1997 | Minturn |
| 5,721,471 A | 2/1998 | Begemann |
| 5,742,516 A | 4/1998 | Olcerst |
| D396,581 S | 8/1998 | Schubert |
| 5,791,982 A | 8/1998 | Curry |
| 5,805,267 A | 9/1998 | Goldman |
| D401,085 S | 11/1998 | Grant |
| 5,861,717 A | 1/1999 | Begemann |
| 5,892,690 A | 4/1999 | Boatman |
| 5,919,217 A | 7/1999 | Hughes |
| 5,937,387 A | 8/1999 | Summerell |

(56) References Cited

U.S. PATENT DOCUMENTS

| | | |
|---|---|---|
| 5,963,294 A | 10/1999 | Schiffer |
| 5,976,010 A | 11/1999 | Reese |
| 6,053,936 A | 4/2000 | Koyama |
| 6,055,480 A | 4/2000 | Nevo |
| D424,356 S | 5/2000 | Hahn |
| 6,118,230 A | 9/2000 | Fleischmann |
| 6,135,970 A | 10/2000 | Kadhiresan |
| 6,166,496 A | 12/2000 | Lys |
| 6,170,318 B1 | 1/2001 | Lewis |
| 6,197,094 B1 | 3/2001 | Thofelt |
| 6,208,905 B1 | 3/2001 | Giddings |
| 6,235,046 B1 | 5/2001 | Gerdt |
| 6,238,337 B1 | 5/2001 | Kambhatla |
| 6,269,339 B1 | 7/2001 | Silver |
| 6,290,140 B1 | 9/2001 | Pesko |
| 6,331,160 B1 | 12/2001 | Bardy |
| 6,340,868 B1 | 1/2002 | Lys |
| 6,344,641 B1 | 2/2002 | Blalock |
| 6,348,867 B1 | 2/2002 | Myllymaeki |
| 6,350,275 B1 | 2/2002 | Vreman |
| 6,369,716 B1 | 4/2002 | Abbas |
| 6,387,844 B1 | 5/2002 | Fujishima |
| 6,441,558 B1 | 8/2002 | Muthu |
| 6,448,550 B1 | 9/2002 | Nishimura |
| 6,459,919 B1 | 10/2002 | Lys |
| 6,498,440 B2 | 12/2002 | Stam |
| 6,503,462 B1 | 1/2003 | Michalakos |
| 6,507,159 B2 | 1/2003 | Muthu |
| 6,507,709 B2 | 1/2003 | Hirai |
| 6,525,658 B2 | 2/2003 | Streetman |
| 6,535,190 B2 | 3/2003 | Evanicky |
| 6,554,439 B1 | 4/2003 | Teicher |
| 6,567,009 B2 | 5/2003 | Ohishi |
| 6,583,720 B1 | 6/2003 | Quigley |
| D477,158 S | 7/2003 | Calcerano |
| 6,589,912 B2 | 7/2003 | Kawai |
| 6,607,484 B2 | 8/2003 | Suzuki |
| 6,610,127 B2 | 8/2003 | Lu |
| 6,623,512 B1 | 9/2003 | Heller |
| 6,661,798 B2 | 12/2003 | Sano |
| 6,683,419 B2 | 1/2004 | Kriparos |
| 6,691,070 B1 | 2/2004 | Williams |
| 6,711,470 B1 | 3/2004 | Hartenstein |
| 6,720,745 B2 | 4/2004 | Lys |
| 6,727,091 B2 | 4/2004 | Darlington |
| 6,738,551 B2 | 5/2004 | Noda |
| 6,755,783 B2 | 6/2004 | Cosentino |
| 6,756,998 B1 | 6/2004 | Bilger |
| 6,757,710 B2 | 6/2004 | Reed |
| 6,772,016 B1 | 8/2004 | Oern |
| 6,774,802 B2 | 8/2004 | Bachinski |
| 6,782,351 B2 | 8/2004 | Reichel |
| 6,806,659 B1 | 10/2004 | Mueller |
| 6,834,208 B2 | 12/2004 | Gonzales |
| 6,862,529 B2 | 3/2005 | Brown |
| 6,865,428 B2 | 3/2005 | Gonzales |
| 6,878,191 B2 | 4/2005 | Escaffre |
| 6,879,451 B1 | 4/2005 | Hewlett |
| 6,888,453 B2 | 5/2005 | Lutz |
| 6,888,779 B2 | 5/2005 | Mollicone |
| 6,904,508 B2 | 6/2005 | Selkirk |
| 6,912,429 B1 | 6/2005 | Bilger |
| 6,933,486 B2 | 8/2005 | Pitigoi-Aron |
| 6,967,565 B2 | 11/2005 | Lingemann |
| 6,991,029 B2 | 1/2006 | Orfield |
| 6,992,803 B2 | 1/2006 | Chang |
| 7,014,336 B1 | 3/2006 | Ducharme |
| 7,024,256 B2 | 4/2006 | Krzyzanowski |
| 7,038,399 B2 | 5/2006 | Lys |
| 7,065,280 B2 | 6/2006 | Ogawa |
| 7,067,995 B2 | 6/2006 | Gunter |
| D526,512 S | 8/2006 | Hahn |
| 7,092,101 B2 | 8/2006 | Brady |
| 7,097,111 B2 | 8/2006 | Riley |
| 7,099,723 B2 | 8/2006 | Gonzales |
| 7,113,086 B2 | 9/2006 | Shorrock |
| D530,940 S | 10/2006 | Raile |
| 7,129,855 B2 | 10/2006 | Krzyzanowski |
| 7,145,295 B1 | 12/2006 | Lee |
| 7,145,614 B2 | 12/2006 | Lee |
| 7,173,384 B2 | 2/2007 | Ploetz |
| 7,190,126 B1 | 3/2007 | Paton |
| 7,202,613 B2 | 4/2007 | Morgan |
| 7,213,940 B1 | 5/2007 | Van De Ven |
| 7,215,086 B2 | 5/2007 | Maxik |
| 7,224,282 B2 | 5/2007 | Terauchi |
| 7,256,554 B2 | 8/2007 | Lys |
| 7,260,950 B2 | 8/2007 | Choi |
| 7,274,160 B2 | 9/2007 | Mueller |
| 7,288,902 B1 | 10/2007 | Melanson |
| 7,298,871 B2 | 11/2007 | Lee |
| 7,302,313 B2 | 11/2007 | Sharp |
| 7,308,296 B2 | 12/2007 | Lys |
| 7,319,298 B2 | 1/2008 | Jungwirth |
| 7,324,874 B2 | 1/2008 | Jung |
| 7,327,337 B2 | 2/2008 | Callahan |
| 7,328,243 B2 | 2/2008 | Yeager |
| 7,348,949 B2 | 3/2008 | Lee |
| D566,428 S | 4/2008 | Kester |
| 7,354,172 B2 | 4/2008 | Chemel |
| 7,358,679 B2 | 4/2008 | Lys |
| 7,364,583 B2 | 4/2008 | Rose |
| 7,366,989 B2 | 4/2008 | Naik |
| 7,387,405 B2 | 6/2008 | Ducharme |
| 7,415,310 B2 | 8/2008 | Bovee |
| 7,446,303 B2 | 11/2008 | Maniam |
| 7,453,217 B2 | 11/2008 | Lys |
| 7,457,834 B2 | 11/2008 | Jung |
| 7,520,634 B2 | 4/2009 | Ducharme |
| 7,524,279 B2 | 4/2009 | Auphan |
| 7,536,388 B2 | 5/2009 | Jung |
| 7,545,267 B2 | 6/2009 | Stortoni |
| 7,553,039 B2 | 6/2009 | Harris |
| 7,557,521 B2 | 7/2009 | Lys |
| 7,558,546 B2 | 7/2009 | Johnson |
| 7,567,956 B2 | 7/2009 | Yu |
| 7,572,028 B2 | 8/2009 | Mueller |
| 7,573,210 B2 | 8/2009 | Ashdown |
| 7,574,320 B2 | 8/2009 | Corwin |
| 7,577,915 B2 | 8/2009 | Hunter |
| 7,647,285 B2 | 1/2010 | Heckerman |
| 7,652,582 B2 | 1/2010 | Littell |
| 7,659,673 B2 | 2/2010 | Lys |
| 7,676,280 B1 | 3/2010 | Bash |
| 7,679,281 B2 | 3/2010 | Kim |
| 7,680,745 B2 | 3/2010 | Hunter |
| 7,689,437 B1 | 3/2010 | Teller |
| 7,759,854 B2 | 7/2010 | Miller |
| 7,767,280 B2 | 8/2010 | Klasen-Memmer |
| 7,772,965 B2 | 8/2010 | Farhan |
| 7,779,097 B2 | 8/2010 | Lamkin |
| 7,792,920 B2 | 9/2010 | Istvan |
| 7,827,039 B2 | 11/2010 | Butcher |
| 7,828,205 B2 | 11/2010 | Cronin |
| 7,839,275 B2 | 11/2010 | Spalink |
| 7,840,310 B2 | 11/2010 | Orfield |
| 7,843,353 B2 | 11/2010 | Pan |
| 7,848,945 B2 | 12/2010 | Rozell |
| D632,102 S | 2/2011 | Sato |
| D634,952 S | 3/2011 | Gile |
| 7,901,071 B1 | 3/2011 | Kulas |
| 7,906,789 B2 | 3/2011 | Jung |
| 7,918,406 B2 | 4/2011 | Rosen |
| 7,918,407 B2 | 4/2011 | Patch |
| 7,953,678 B2 | 5/2011 | Hunter |
| 7,967,731 B2 | 6/2011 | Kil |
| 7,973,759 B2 | 7/2011 | Huang |
| 7,977,904 B2 | 7/2011 | Berman |
| 7,987,490 B2 | 7/2011 | Ansari |
| 8,028,706 B2 | 10/2011 | Skene |
| 8,038,615 B2 | 10/2011 | Gobeyn |
| 8,042,049 B2 | 10/2011 | Killian |
| 8,064,295 B2 | 11/2011 | Palmer |
| 8,066,405 B2 | 11/2011 | Simon |

(56) References Cited

U.S. PATENT DOCUMENTS

| | | |
|---|---|---|
| 8,086,407 B2 | 12/2011 | Chan |
| 8,100,552 B2 | 1/2012 | Spero |
| 8,100,746 B2 | 1/2012 | Heidel |
| 8,143,792 B2 | 3/2012 | Joo |
| 8,147,302 B2 | 4/2012 | Desrochers |
| 8,154,398 B2 | 4/2012 | Rolf |
| 8,159,150 B2 | 4/2012 | Ashdown |
| 8,188,873 B2 | 5/2012 | Barth |
| 8,200,744 B2 | 6/2012 | Jung |
| D666,123 S | 8/2012 | Sichello |
| 8,253,349 B2 | 8/2012 | Shteynberg |
| 8,271,575 B2 | 9/2012 | Hunter |
| 8,296,408 B2 | 10/2012 | Anke |
| 8,308,784 B2 | 11/2012 | Streeter |
| 8,321,192 B2 | 11/2012 | Boyce |
| 8,344,665 B2 | 1/2013 | Verfuerth |
| 8,352,408 B2 | 1/2013 | Guillama |
| 8,358,214 B2 | 1/2013 | Amigo |
| 8,359,208 B2 | 1/2013 | Slutzky |
| 8,380,359 B2 | 2/2013 | Duchene |
| 8,392,025 B2 | 3/2013 | Orfield |
| 8,429,223 B2 | 4/2013 | Gilley |
| 8,436,556 B2 | 5/2013 | Eisele |
| 8,446,275 B2 | 5/2013 | Utter, II |
| 8,454,729 B2 | 6/2013 | Mittelmark |
| 8,484,153 B2 | 7/2013 | Mott |
| 8,490,006 B1 | 7/2013 | Reeser |
| 8,497,871 B2 | 7/2013 | Zulch |
| 8,506,612 B2 | 8/2013 | Ashdown |
| 8,508,169 B2 | 8/2013 | Zaharchuk |
| 8,515,785 B2 | 8/2013 | Clark |
| 8,527,213 B2 | 9/2013 | Kailas |
| 8,543,244 B2 | 9/2013 | Keeling |
| 8,543,665 B2 | 9/2013 | Ansari |
| 8,558,466 B2 | 10/2013 | Curasi |
| 8,558,687 B2 | 10/2013 | Haupt |
| 8,609,121 B2 | 12/2013 | Averett |
| 8,630,741 B1 | 1/2014 | Matsuoka |
| 8,640,038 B1 | 1/2014 | Reeser |
| 8,660,861 B2 | 2/2014 | Chun |
| 8,666,666 B2 | 3/2014 | Bassa |
| 8,674,842 B2 | 3/2014 | Zishaan |
| 8,690,771 B2 | 4/2014 | Wekell |
| 8,707,619 B2 | 4/2014 | Edwards |
| 8,716,952 B2 | 5/2014 | Van De Ven |
| 8,755,942 B2 | 6/2014 | Bonilla |
| 8,760,370 B2 | 6/2014 | Maxik |
| 8,795,169 B2 | 8/2014 | Cosentino |
| 8,801,636 B2 | 8/2014 | Lewicke |
| 8,836,243 B2 | 9/2014 | Eisele |
| 8,852,254 B2 | 10/2014 | Moscovici |
| 8,855,757 B2 | 10/2014 | Kapoor |
| 8,862,532 B2 | 10/2014 | Beaulieu |
| 8,870,740 B2 | 10/2014 | Clegg |
| 8,896,427 B1 | 11/2014 | Ramirez |
| 8,907,803 B2 | 12/2014 | Martin |
| 8,924,026 B2 | 12/2014 | Federspiel |
| 8,961,414 B2 | 2/2015 | Teller |
| 8,979,913 B2 | 3/2015 | D Ambrosio |
| 8,986,427 B2 | 3/2015 | Hauville |
| 9,007,877 B2 | 4/2015 | Godlieb |
| 9,010,019 B2 | 4/2015 | Mittelmark |
| 9,015,610 B2 | 4/2015 | Hunter |
| 9,020,647 B2 | 4/2015 | Johnson |
| 9,032,097 B2 | 5/2015 | Albanese |
| 9,032,215 B2 | 5/2015 | Kalofonos |
| 9,044,567 B2 | 6/2015 | Poirrier |
| 9,063,739 B2 | 6/2015 | Ward |
| 9,066,405 B2 | 6/2015 | Van De Ven |
| D734,958 S | 7/2015 | Gosling |
| 9,095,029 B2 | 7/2015 | Lu |
| D737,078 S | 8/2015 | McKinney |
| 9,098,114 B2 | 8/2015 | Potter |
| 9,104,183 B2 | 8/2015 | Zheng |
| 9,118,499 B2 | 8/2015 | Hunter |
| 9,125,257 B2 | 9/2015 | Eisele |
| 9,125,274 B1 | 9/2015 | Brunault |
| 9,147,296 B2 | 9/2015 | Ricci |
| 9,154,559 B1 | 10/2015 | Bovee |
| 9,155,165 B2 | 10/2015 | Chobot |
| 9,204,518 B2 | 12/2015 | Jung |
| 9,220,202 B2 | 12/2015 | Maxik |
| 9,226,371 B2 | 12/2015 | Mohan |
| 9,230,064 B2 | 1/2016 | Yanev |
| 9,230,560 B2 | 1/2016 | Ehsani |
| 9,236,026 B2 | 1/2016 | Jia |
| 9,248,309 B2 | 2/2016 | Pugh |
| 9,297,748 B2 | 3/2016 | Risk |
| 9,306,763 B2 | 4/2016 | Tatzel |
| 9,326,363 B2 | 4/2016 | Godlieb |
| 9,345,091 B2 | 5/2016 | Pickard |
| 9,360,731 B2 | 6/2016 | Berman |
| 9,370,689 B2 | 6/2016 | Guillama |
| D761,598 S | 7/2016 | Goodman |
| 9,392,665 B2 | 7/2016 | Eisele |
| 9,410,664 B2 | 8/2016 | Krames |
| 9,420,667 B2 | 8/2016 | Mohan |
| 9,429,009 B2 | 8/2016 | Paulk |
| 9,430,617 B2 | 8/2016 | Brust |
| 9,430,927 B2 | 8/2016 | Yu |
| 9,456,482 B1 | 9/2016 | Pope |
| 9,465,392 B2 | 10/2016 | Bradley |
| 9,493,112 B2 | 11/2016 | Thomas |
| 9,501,049 B2 | 11/2016 | Balakrishnan |
| 9,510,426 B2 | 11/2016 | Chemel |
| 9,526,455 B2 | 12/2016 | Horseman |
| 9,576,939 B2 | 2/2017 | Roth |
| 9,593,861 B1 | 3/2017 | Burnett |
| 9,595,118 B2 | 3/2017 | Maxik |
| 9,609,724 B2 | 3/2017 | Bulut |
| 9,615,429 B2 | 4/2017 | Roosli |
| 9,636,520 B2 | 5/2017 | Pedersen |
| 9,642,209 B2 | 5/2017 | Eisele |
| 9,655,195 B2 | 5/2017 | Tseng |
| 9,696,052 B2 | 7/2017 | Malchiondo |
| 9,699,874 B2 | 7/2017 | Phillips |
| 9,715,242 B2 * | 7/2017 | Pillai .................. F24F 11/0008 |
| 9,730,298 B2 | 8/2017 | Vangeel |
| 9,788,373 B1 | 10/2017 | Chowdhury |
| 9,827,439 B2 | 11/2017 | Maxik |
| 9,839,083 B2 | 12/2017 | Van De Ven |
| 9,887,854 B2 | 2/2018 | Park |
| 9,890,969 B2 | 2/2018 | Martin |
| 9,907,149 B1 | 2/2018 | Dolan |
| 9,909,772 B2 | 3/2018 | Bazar |
| 9,915,438 B2 | 3/2018 | Cheatham, III |
| 9,924,243 B2 | 3/2018 | Lupien |
| 9,933,182 B2 | 4/2018 | Alfakhrany |
| 9,939,823 B2 | 4/2018 | Ovadia |
| 9,952,614 B2 | 4/2018 | Hunter |
| 9,955,423 B2 | 4/2018 | Kates |
| 9,955,550 B2 | 4/2018 | Baek |
| 9,958,180 B2 | 5/2018 | Mahar |
| 9,959,997 B2 | 5/2018 | Bailey |
| 9,984,590 B2 | 5/2018 | Stevens |
| 9,986,313 B2 | 5/2018 | Schwarzkopf |
| 10,001,789 B2 | 6/2018 | Hunka |
| 10,022,556 B1 | 7/2018 | Holbert |
| 10,024,699 B2 | 7/2018 | Rapetti Mogol |
| 10,030,833 B2 | 7/2018 | Adler |
| 10,031,973 B2 | 7/2018 | Dey |
| 10,039,169 B2 | 7/2018 | Chen |
| 10,042,336 B2 | 8/2018 | Cipollo |
| 10,047,971 B2 | 8/2018 | Nyamjav |
| 10,051,707 B2 | 8/2018 | Deixler |
| 10,052,061 B2 | 8/2018 | Raymann |
| 10,054,534 B1 | 8/2018 | Nourbakhsh |
| 10,057,963 B2 | 8/2018 | Mead |
| 10,064,255 B2 * | 8/2018 | Barroso .................. A61N 5/0618 |
| 10,068,297 B2 | 9/2018 | Hull Roskos |
| 10,072,866 B2 | 9/2018 | Bazar |
| 10,075,757 B2 | 9/2018 | Ugan |
| 10,078,865 B2 | 9/2018 | Joshi |
| 10,088,577 B2 | 10/2018 | Klein |

(56) References Cited

U.S. PATENT DOCUMENTS

| | | |
|---|---|---|
| 10,091,017 B2 | 10/2018 | Landow et al. |
| 10,091,303 B1 | 10/2018 | Ledvina |
| 10,178,972 B2 | 1/2019 | Raymann |
| 10,203,267 B2 | 2/2019 | D'Orlando |
| 10,230,538 B2 | 3/2019 | Killian |
| 10,271,400 B2 * | 4/2019 | Parker .................. H05B 47/155 |
| 2002/0072322 A1 | 6/2002 | Sharp |
| 2002/0096121 A1 | 7/2002 | Ingman |
| 2002/0119281 A1 | 8/2002 | Higgins |
| 2002/0128864 A1 | 9/2002 | Maus |
| 2002/0163529 A1 | 11/2002 | Evanicky |
| 2002/0187082 A1 | 12/2002 | Wu |
| 2003/0100837 A1 | 5/2003 | Lys |
| 2003/0133292 A1 | 7/2003 | Mueller |
| 2003/0199244 A1 | 10/2003 | Siddaramanna |
| 2003/0209140 A1 | 11/2003 | Kutt |
| 2003/0209501 A1 | 11/2003 | Leung |
| 2004/0002792 A1 | 1/2004 | Hoffknecht |
| 2004/0060677 A1 | 4/2004 | Huang |
| 2004/0065098 A1 | 4/2004 | Choi |
| 2004/0105264 A1 | 6/2004 | Spero |
| 2004/0160199 A1 | 8/2004 | Morgan |
| 2004/0176666 A1 | 9/2004 | Chait |
| 2004/0178751 A1 | 9/2004 | Mueller |
| 2004/0212321 A1 | 10/2004 | Lys |
| 2004/0245351 A1 | 12/2004 | Orfield |
| 2004/0264193 A1 | 12/2004 | Okumura |
| 2004/0267385 A1 | 12/2004 | Lingemann |
| 2005/0004942 A1 | 1/2005 | Madsen |
| 2005/0110416 A1 | 5/2005 | Veskovic |
| 2005/0151489 A1 | 7/2005 | Lys |
| 2005/0177957 A1 | 8/2005 | Long |
| 2005/0191505 A1 | 9/2005 | Akarsu |
| 2005/0200578 A1 | 9/2005 | Lee |
| 2005/0213353 A1 | 9/2005 | Lys |
| 2005/0214533 A1 | 9/2005 | Shimosaki |
| 2005/0218870 A1 | 10/2005 | Lys |
| 2005/0225976 A1 | 10/2005 | Zampini |
| 2005/0231133 A1 | 10/2005 | Lys |
| 2005/0236998 A1 | 10/2005 | Mueller |
| 2005/0253533 A1 | 11/2005 | Lys |
| 2006/0000257 A1 | 1/2006 | Samadpour |
| 2006/0002110 A1 | 1/2006 | Dowling |
| 2006/0017928 A1 | 1/2006 | Crowther |
| 2006/0018118 A1 | 1/2006 | Lee |
| 2006/0018428 A1 | 1/2006 | Li |
| 2006/0026972 A1 | 2/2006 | Masui |
| 2006/0103728 A1 | 5/2006 | Ishigami |
| 2006/0106437 A1 | 5/2006 | Czeisler |
| 2006/0111944 A1 | 5/2006 | Sirmans, Jr. |
| 2006/0154596 A1 | 7/2006 | Meneely, Jr. |
| 2006/0162552 A1 | 7/2006 | Yost |
| 2006/0172579 A1 | 8/2006 | Murphy |
| 2006/0173580 A1 | 8/2006 | Desrochers |
| 2006/0184283 A1 | 8/2006 | Lee |
| 2006/0207730 A1 | 9/2006 | Berman |
| 2006/0246149 A1 | 11/2006 | Buchholz |
| 2007/0001617 A1 | 1/2007 | Pogodayev |
| 2007/0024210 A1 | 2/2007 | Zwanenburg |
| 2007/0115665 A1 | 5/2007 | Mueller |
| 2007/0162858 A1 | 7/2007 | Hurley |
| 2007/0198226 A1 | 8/2007 | Lee |
| 2007/0240437 A1 | 10/2007 | Yonezawa |
| 2007/0276270 A1 | 11/2007 | Tran |
| 2007/0288247 A1 | 12/2007 | Mackay |
| 2008/0031832 A1 | 2/2008 | Wakefield |
| 2008/0103561 A1 | 5/2008 | Moscovici |
| 2008/0146892 A1 | 6/2008 | LeBoeuf |
| 2008/0182506 A1 | 7/2008 | Jackson |
| 2008/0224121 A1 | 9/2008 | Bose |
| 2008/0225021 A1 | 9/2008 | Hekstra |
| 2008/0246629 A1 | 10/2008 | Tsui |
| 2008/0277486 A1 * | 11/2008 | Seem .................. F24F 11/30 236/49.3 |
| 2008/0294012 A1 | 11/2008 | Kurtz |
| 2008/0297027 A1 | 12/2008 | Miller |
| 2009/0015403 A1 | 1/2009 | Kuris |
| 2009/0053989 A1 | 2/2009 | Lunde |
| 2009/0065596 A1 | 3/2009 | Seem |
| 2009/0068089 A1 | 3/2009 | Hussain |
| 2009/0104086 A1 | 4/2009 | Zax |
| 2009/0115597 A1 * | 5/2009 | Giacalone ........... H04L 12/2827 340/506 |
| 2009/0126382 A1 | 5/2009 | Rubino |
| 2009/0128044 A1 | 5/2009 | Nevins |
| 2009/0169425 A1 | 7/2009 | Park |
| 2009/0177613 A1 | 7/2009 | Martinez |
| 2009/0223126 A1 | 9/2009 | Garner |
| 2009/0241496 A1 | 10/2009 | Pintault |
| 2009/0242485 A1 | 10/2009 | Cabados |
| 2009/0243517 A1 | 10/2009 | Verfuerth |
| 2009/0273470 A1 | 11/2009 | Sinkevicius |
| 2009/0292180 A1 | 11/2009 | Mirow |
| 2009/0300673 A1 | 12/2009 | Bachet |
| 2010/0021710 A1 | 1/2010 | Hunt |
| 2010/0084996 A1 | 4/2010 | Van De Sluis |
| 2010/0119461 A1 | 5/2010 | Bicard-Benhamou |
| 2010/0146855 A1 | 6/2010 | Ma |
| 2010/0169108 A1 | 7/2010 | Karkanias |
| 2010/0185064 A1 | 7/2010 | Bandic |
| 2010/0197495 A1 | 8/2010 | Filippini |
| 2010/0217099 A1 | 8/2010 | Leboeuf |
| 2010/0265803 A1 | 10/2010 | Lee |
| 2010/0277106 A1 | 11/2010 | Baaijens |
| 2010/0289643 A1 | 11/2010 | Trundle |
| 2010/0298981 A1 | 11/2010 | Chamorro |
| 2011/0010014 A1 | 1/2011 | Oexman |
| 2011/0066465 A1 | 3/2011 | Orfield |
| 2011/0084614 A1 | 4/2011 | Eisele |
| 2011/0186644 A1 * | 8/2011 | Yoshii ................ F24F 11/30 236/46 A |
| 2011/0190913 A1 | 8/2011 | Van De Sluis et al. |
| 2011/0190945 A1 * | 8/2011 | Yoshii ................ F24F 11/30 700/277 |
| 2012/0003198 A1 | 1/2012 | Barker |
| 2012/0011033 A1 | 1/2012 | Salgia |
| 2012/0019386 A1 | 1/2012 | Doraiswami |
| 2012/0031984 A1 | 2/2012 | Feldmeier |
| 2012/0064818 A1 | 3/2012 | Kurelowech |
| 2012/0072032 A1 * | 3/2012 | Powell ................ F24F 11/30 700/278 |
| 2012/0139720 A1 | 6/2012 | Mazar |
| 2012/0158203 A1 | 6/2012 | Feldstein |
| 2012/0176041 A1 | 7/2012 | Birru |
| 2012/0206726 A1 | 8/2012 | Pervez |
| 2012/0279120 A1 | 11/2012 | Prescott |
| 2012/0298599 A1 | 11/2012 | Sichello |
| 2013/0027637 A1 | 1/2013 | Hosoki |
| 2013/0035208 A1 | 2/2013 | Dalebout |
| 2013/0065098 A1 | 3/2013 | Ohkawa |
| 2013/0073093 A1 * | 3/2013 | Songkakul ........... G05B 15/02 700/276 |
| 2013/0081541 A1 | 4/2013 | Hasenoehrl |
| 2013/0102852 A1 | 4/2013 | Kozloski |
| 2013/0119891 A1 | 5/2013 | Herremans et al. |
| 2013/0134962 A1 | 5/2013 | Kamel |
| 2013/0141235 A1 | 6/2013 | Utter, II |
| 2013/0208576 A1 | 8/2013 | Loree, IV |
| 2013/0229114 A1 | 9/2013 | Eisele |
| 2013/0276371 A1 | 10/2013 | Birru |
| 2013/0342111 A1 | 12/2013 | Mohan |
| 2014/0039685 A1 | 2/2014 | Blount |
| 2014/0058566 A1 | 2/2014 | Rains, Jr. |
| 2014/0067130 A1 * | 3/2014 | Pillai .................. H05B 47/10 700/275 |
| 2014/0093551 A1 | 4/2014 | Averett |
| 2014/0099348 A1 | 4/2014 | Averett |
| 2014/0107846 A1 * | 4/2014 | Li ..................... F24F 11/30 700/275 |
| 2014/0142760 A1 * | 5/2014 | Drees ................. G05B 15/02 700/275 |
| 2014/0243935 A1 | 8/2014 | Brainard |

(56) References Cited

U.S. PATENT DOCUMENTS

| | | |
|---|---|---|
| 2014/0266669 A1* | 9/2014 | Fadell .................. H05B 47/115 340/501 |
| 2014/0277757 A1* | 9/2014 | Wang ....................... F24F 11/30 700/276 |
| 2014/0283450 A1 | 9/2014 | Darlington |
| 2014/0298719 A1 | 10/2014 | Mackin |
| 2014/0318011 A1 | 10/2014 | Järvinen |
| 2015/0015152 A1 | 1/2015 | Aboulnaga |
| 2015/0052975 A1 | 2/2015 | Martin |
| 2015/0066578 A1 | 3/2015 | Manocchia |
| 2015/0088786 A1 | 3/2015 | Anandhakrishnan |
| 2015/0102730 A1 | 4/2015 | Eisele |
| 2015/0126806 A1* | 5/2015 | Barroso ............... H05B 47/175 600/27 |
| 2015/0134123 A1 | 5/2015 | Obinelo |
| 2015/0204561 A1* | 7/2015 | Sadwick ............. G05D 23/1905 236/10 |
| 2015/0212057 A1 | 7/2015 | Darveau |
| 2015/0234369 A1 | 8/2015 | Wen |
| 2015/0309484 A1 | 10/2015 | Lyman |
| 2015/0312696 A1* | 10/2015 | Ribbich ................. H04W 4/029 455/418 |
| 2015/0382427 A1 | 12/2015 | Eisele |
| 2016/0019813 A1 | 1/2016 | Mullen |
| 2016/0139576 A1* | 5/2016 | Aiken .................. F24F 11/0001 700/276 |
| 2016/0151603 A1 | 6/2016 | Shouldice |
| 2016/0203700 A1 | 7/2016 | Bruhn |
| 2016/0206898 A1 | 7/2016 | Brainard |
| 2016/0213946 A1 | 7/2016 | Brainard |
| 2016/0231014 A1 | 8/2016 | Ro |
| 2016/0253802 A1 | 9/2016 | Venetianer |
| 2016/0313245 A1 | 10/2016 | Sato |
| 2016/0339203 A1 | 11/2016 | Krames |
| 2016/0341436 A1* | 11/2016 | Parker ..................... H05B 45/20 |
| 2016/0377305 A1* | 12/2016 | Kwa ....................... F24F 11/30 700/277 |
| 2017/0023225 A1 | 1/2017 | Chen |
| 2017/0038787 A1* | 2/2017 | Baker ..................... H05B 47/19 |
| 2017/0053068 A1 | 2/2017 | Pillai |
| 2017/0065792 A1 | 3/2017 | Bonvallet |
| 2017/0068782 A1 | 3/2017 | Pillai |
| 2017/0136206 A1 | 5/2017 | Pillai |
| 2017/0139386 A1 | 5/2017 | Pillai |
| 2017/0162548 A1 | 6/2017 | Roth |
| 2017/0189640 A1 | 7/2017 | Sadwick |
| 2017/0191695 A1 | 7/2017 | Bruhn |
| 2017/0196510 A1 | 7/2017 | Ouwerkerk |
| 2017/0238401 A1* | 8/2017 | Sadwick ................. F21K 9/235 315/294 |
| 2017/0259079 A1 | 9/2017 | Grajcar |
| 2017/0299210 A1 | 10/2017 | Nyamjav |
| 2017/0307243 A1* | 10/2017 | Burt ........................ F24F 11/30 |
| 2017/0319816 A1 | 11/2017 | Sokol |
| 2017/0325310 A1 | 11/2017 | Chen |
| 2017/0326380 A1 | 11/2017 | Moore-Ede |
| 2017/0348506 A1 | 12/2017 | Berman |
| 2017/0356670 A1 | 12/2017 | Zhang |
| 2017/0359879 A1 | 12/2017 | Eisele |
| 2017/0363314 A1* | 12/2017 | Barber ................... H05B 47/19 |
| 2018/0042077 A1 | 2/2018 | Riley |
| 2018/0043130 A1* | 2/2018 | Moore-Ede .......... A61N 5/0618 |
| 2018/0077767 A1 | 3/2018 | Soler |
| 2018/0149802 A1 | 5/2018 | Krames |
| 2018/0160944 A1 | 6/2018 | Aubert |
| 2018/0206783 A1 | 7/2018 | Yoon |
| 2018/0207445 A1 | 7/2018 | Maxik |
| 2018/0209683 A1 | 7/2018 | Cho |
| 2018/0285934 A1 | 10/2018 | Baughman |
| 2018/0295696 A1 | 10/2018 | Li |
| 2018/0295704 A1 | 10/2018 | Haverlag |
| 2018/0311464 A1 | 11/2018 | Krames |
| 2018/0318602 A1 | 11/2018 | Ciccarelli |
| 2018/0320919 A1 | 11/2018 | Tang |
| 2018/0322240 A1 | 11/2018 | Goyal |
| 2018/0322253 A1 | 11/2018 | Goyal |
| 2018/0331845 A1 | 11/2018 | Warren |
| 2018/0339127 A1 | 11/2018 | Van Reen |
| 2018/0349689 A1 | 12/2018 | Lee |
| 2018/0349945 A1 | 12/2018 | Jayaraman |
| 2018/0351758 A1 | 12/2018 | Becker |
| 2018/0351761 A1 | 12/2018 | Li |
| 2018/0353108 A1 | 12/2018 | Prate |
| 2019/0011146 A1 | 1/2019 | Seo |
| 2019/0013960 A1* | 1/2019 | Sadwick ............. H04L 12/2816 |
| 2019/0014643 A1 | 1/2019 | Gharabegian |
| 2019/0024926 A1 | 1/2019 | Kim |
| 2019/0028549 A1 | 1/2019 | Ledvina |
| 2019/0046109 A1 | 2/2019 | Lewis |
| 2019/0075687 A1 | 3/2019 | Brunstetter |
| 2019/0215184 A1 | 7/2019 | Emigh |
| 2019/0320516 A1* | 10/2019 | Parker ..................... H05B 45/20 |

FOREIGN PATENT DOCUMENTS

| | | |
|---|---|---|
| CN | 1150882 | 5/1997 |
| CN | 1544222 | 11/2004 |
| CN | 101421558 | 4/2009 |
| CN | 201414191 Y | 2/2010 |
| CN | 202551821 | 11/2012 |
| CN | 103040443 A | 4/2013 |
| CN | 103197659 A | 7/2013 |
| CN | 103277870 | 9/2013 |
| CN | 203175090 U | 9/2013 |
| CN | 103531174 A | 1/2014 |
| CN | 103604198 A | 2/2014 |
| CN | 203454309 U | 2/2014 |
| CN | 204759076 | 11/2015 |
| EP | 1067825 | 1/2001 |
| EP | 1271442 | 1/2003 |
| EP | 1511218 | 3/2005 |
| EP | 1821582 | 8/2007 |
| EP | 2016879 | 1/2009 |
| EP | 2132960 | 12/2009 |
| EP | 2296448 | 3/2011 |
| EP | 2431541 | 3/2012 |
| EP | 2488912 | 8/2012 |
| JP | S60110520 A | 6/1985 |
| JP | H0552361 A | 3/1993 |
| JP | H0658593 | 3/1994 |
| JP | H0658593 A | 3/1994 |
| JP | H06159763 A | 6/1994 |
| JP | H06225858 A | 8/1994 |
| JP | H09303842 A | 11/1997 |
| JP | H10238089 A | 9/1998 |
| JP | 2000130828 | 5/2000 |
| JP | 2000294388 | 10/2000 |
| JP | 2001224078 | 8/2001 |
| JP | 2001286226 | 10/2001 |
| JP | 2001314882 | 11/2001 |
| JP | 2002042546 A | 2/2002 |
| JP | 2002059152 A | 2/2002 |
| JP | 2003042507 | 2/2003 |
| JP | 2003042509 | 2/2003 |
| JP | 2003083590 | 3/2003 |
| JP | 2003232559 | 8/2003 |
| JP | 2004005313 A | 1/2004 |
| JP | 2004053130 A | 2/2004 |
| JP | 2005040769 A | 2/2005 |
| JP | 2005177726 | 7/2005 |
| JP | 2005211319 | 8/2005 |
| JP | 2005235634 | 9/2005 |
| JP | 2006210045 | 8/2006 |
| JP | 2006522699 | 10/2006 |
| JP | 2006321721 | 11/2006 |
| JP | 2007170761 | 7/2007 |
| JP | 2007184436 | 7/2007 |
| JP | 2008125541 | 6/2008 |
| JP | 2008157548 | 7/2008 |
| JP | 2008204640 | 9/2008 |
| JP | 2010182661 | 8/2010 |
| JP | 2010239878 | 10/2010 |
| JP | 2011146137 | 7/2011 |

(56) References Cited

FOREIGN PATENT DOCUMENTS

| | | |
|---|---|---|
| JP | 2012001931 | 1/2012 |
| JP | 2012149839 A | 8/2012 |
| JP | 2013140523 A | 7/2013 |
| JP | 6159763 A | 12/2015 |
| JP | 6225858 A | 4/2016 |
| KR | 20000009824 A | 2/2000 |
| KR | 20010048235 | 6/2001 |
| KR | 20030074107 A | 9/2003 |
| KR | 20050003899 | 1/2005 |
| KR | 100771486 | 10/2007 |
| KR | 100804892 | 2/2008 |
| KR | 101102733 | 5/2011 |
| KR | 20120004243 | 1/2012 |
| KR | 101135926 | 4/2012 |
| KR | 20120039359 A | 4/2012 |
| KR | 20130108709 | 10/2013 |
| KR | 20130124184 | 11/2013 |
| WO | 0039964 | 7/2000 |
| WO | 2000058873 | 10/2000 |
| WO | 2004037301 | 5/2004 |
| WO | 2007026387 | 3/2007 |
| WO | 2008043396 | 4/2008 |
| WO | 2008102308 | 8/2008 |
| WO | 2008120127 | 10/2008 |
| WO | 2008135093 | 11/2008 |
| WO | 2009030641 | 3/2009 |
| WO | 2009044330 A1 | 4/2009 |
| WO | 2010046875 | 4/2010 |
| WO | 2010087386 | 8/2010 |
| WO | 2010115720 | 10/2010 |
| WO | 2011033377 | 3/2011 |
| WO | 2011046875 | 4/2011 |
| WO | 2012104773 | 8/2012 |
| WO | 2012151407 | 11/2012 |
| WO | 2013014337 | 1/2013 |
| WO | 2013049297 | 4/2013 |
| WO | 2013175348 | 11/2013 |
| WO | 2014013376 | 1/2014 |
| WO | 2015130786 | 9/2015 |
| WO | 2015/200730 A1 | 12/2015 |
| WO | 2016/019005 A1 | 2/2016 |
| WO | 2016154320 | 9/2016 |
| WO | 2018039433 | 3/2018 |

OTHER PUBLICATIONS

Extended European Search report issued in EP Application No. 20152815.5 dated Aug. 4, 2020.
Extended European Search Report issued in EP Application No. 20191237.5 dated Sep. 21, 2020.
First Examination Report issued in IN Application No. 201617032677 dated Jul. 30, 2020.
Klein, Laura et al., "Coordinating occupant behavior for building energy and comfort management using multi-agent systems," Automatoin in Construction, vol. 22, Mar. 2012, pp. 525-536.
Wikipedia, "Home automation," Jan. 17, 2014, URL: https://en.wikipedia.org/w/index.php?title=Home_automation&oldid=591169195, retreived on Sep. 2, 2020 (11 pages).
Communication pursuant to Article 94(3) EPC issued in EP Application No. 20191237.5 dated Jun. 14, 2021 (13 pages).
Office Action issued in MX Application No. MX/a/2016/011107.
"Active Design Guidelines: Promoting Physical Activity and Health in Design," New York City Departments of Design and Construction, 2010.
"Assembly: Civic Design Guidelines," Center for Active Design, 2018.
Allergy Buyers Club, "Philips Wake Up Light Dawn Simulators Alarm Clocks," retrieved from http://www.allergybuyersclub.com/philips-wake-up-light-dawn-simulator-alarm-cloc ks.html, retrieved on Aug. 13, 2012, 2 pages.
Amendment, filed Jan. 25, 2018, for U.S. Appl. No. 15/421,046, Eisele et al., "LED Lighting System," 6 pages.
American Ultraviolet, "Handheld Germicidal Fixtures," retrieved from http://americanultraviolet.com/germicidal_solutions/commercial_products/handheld . . . , retrieved on Aug. 13, 2012, 1 page.
American Ultraviolet, "In Room Germicidal Solutions," HVAC MRS (0810/2.5M), retrieved from http://www.americanultraviolet.com, 2 pages.
Australian Examination report No. 1, dated Dec. 13, 2017, for Australian Application No. 2017200995, 6 pages.
Australian Patent Examination Report, dated Sep. 14, 2016, for Australian Application No. 2013308871, 5 pages.
Averett et al., "Titanium Dioxide Photocatalytic Compositions and Uses Thereof," U.S. Appl. No. 61/482,393, filed May 4, 2011, 25 pages.
Brookstone, "Tranquil Moments® Advanced Sleep Sounds," 2012, retrieved from http://www.brookstone.com/tranquil-moments-advanced-sleep-sound . . . , retrieved on Apr. 28, 2014, 3 pages.
Canadian Office Action, dated Jul. 18, 2017, for Canadian Application No. 2,946,367, 3 pages.
Canadian Office Action, dated Jul. 25, 2017, for Canadian Application No. 2,940,766, 6 pages.
Chinese Office Action, dated May 5, 2016, for Chinese Application No. 201380051774.0, 10 pages.
Communication pursuant to Article 94(3) EPC, dated Mar. 15, 2018, for European Application No. 15 754 628.4-1222, 9 pages.
Communication pursuant to Article 94(3) EPC, dated Nov. 23, 2016, for European Application No. 13833105.3, 8 pages.
Communication pursuant to Rule 164(1) EPC, dated Mar. 30, 2016, for European Application No. 13833105.3-1853/2891019, 9 pages.
Corrected Notice of Allowance, dated Jun. 26, 2017, for U.S. Appl. No. 14/012,444, Pillai et al., "Systems, Methods and Articles for Enhancing Wellness Associated With Habitable Environments," 2 pages.
Corrected Notice of Allowance, dated Jun. 6, 2017, for U.S. Appl. No. 14/012,444, Pillai et al., "Systems, Methods and Articles for Enhancing Wellness Associated With Habitable Environments," 2 pages.
Delos, "Delos and MGM Grand Las Vegas Introduce First-Ever Stay Well Rooms," Sep. 20, 2012, retrieved from http://delosliving.com/staywell/delos-mgm-grand-las-vegas-introduce-first-ever-stay-well- . . . retrieved on May 14, 2014, 4 pages.
Delos, "Delos Announces First-Ever Well™ Certified Office at CBRE Headquarters In Los Angeles," Nov. 19, 2013, retrieved from http://delosliving.com/press-release/delos-the-pioneer-of-wellness-real-estate-a nnounces-fi . . . , retrieved on May 14, 2014, 4 pages.
Delos, "MGM Grand and Delos Complete Expansion of Stay Well Experience and Introduce New Stay Well Lounge," Feb. 26, 2014, retrieved from http://delosliving.com/press-release/mgm-grand-and-delos-complete-expansion-of-s tay-we . . . , retrieved on May 14, 2014, 4 pages.
Delos, "World's First Well® Certified Restaurants Introduced by Delos and Lyfe Kitchen," Dec. 4, 2013, retrieved from http://delosliving.com/press-release/worlds-first-well-certified-restaurants-int roduced-by-d . . . retrieved on May 14, 2014, 4 pages.
Delos, "World's First Wellness-Infused Student Housing Model in Philadelphia for St. Joseph's University Introduced by Delos and Cross Properties," Nov. 25, 2013, retrieved from http://delosliving.com/press-release/delos-the-pioneer-of-wellness-real-estate-a nd-cross-pr . . . , retrieved on May 14, 2014, 4 pages.
Delos, "Introducing Wellness Real Estate—Can Your Home Actually Improve Your Health?," May 1, 2012, retrieved from http://delosliving.com/press-release/can-your-home-actually-improve-your-health/ , retrieved on May 14, 2014, 3 pages.
Eisele et al., "LED Lighting System," Notice of Allowance, dated Apr. 21, 2015, for U.S. Appl. No. 14/486,753, 9 pages.
Eisele et al, "LED Lighting System," Notice of Allowance, dated Mar. 14, 2016, for U.S. Appl. No. 14/805,243, 6 pages.
Eisele et al, "LED Lighting System," Notice of Allowance, dated May 13, 2014, for U.S. Appl. No. 13/863,589, 6 pages.
Eisele et al, "LED Lighting System," Office Action, dated Feb. 4, 2015, for U.S. Appl. No. 14/486,753, 7 pages.
Eisele et al, "LED Lighting System," Office Action, dated Jul. 26, 2012, for U.S. Appl. No. 12/900,158, 13 pages.

(56) References Cited

OTHER PUBLICATIONS

Eisele et al, "LED Lighting System," Office Action, dated Jun. 5, 2013, for U.S. Appl. No. 13/863,589, 6 pages.
Eisele et al, "LED Lighting System," Office Action, dated Nov. 1, 2013, for U.S. Appl. No. 13/863,589, 7 pages.
Eisele et al, "LED Lighting System," Office Action, dated Oct. 22, 2015, for U.S. Appl. No. 14/805,243, 18 pages.
Eisele et al, "LED Lighting System," Preliminary Amendment, filed Dec. 30, 2014, for U.S. Appl. No. 14/486,753.
Eisele et al, "LED Lighting System," Preliminary Amendment, filed Sep. 15, 2015, for U.S. Appl. No. 14/805,243, 9 pages.
Eisele et al, "LED Lighting System," Preliminary Amendment, filed Sep. 8, 2016, for U.S. Appl. No. 15/187,317, 9 pages.
Eisele et al, "LED Lighting System," Response, filed Jan. 27, 2014, for U.S. Appl. No. 13/863,589, 3 pages.
Eisele et al, "LED Lighting System," Response, filed Jan. 5, 2016, for U.S. Appl. No. 14/805,243, 3 pages.
Eisele et al, "LED Lighting System," Response, filed Mar. 6, 2015, for U.S. Appl. No. 14/486,753, 3 pages.
Eisele et al, "LED Lighting System," Response, filed Sep. 4, 2013, for U.S. Appl. No. 13/863,589, 3 pages.
Eisele et al., "LED Lighting System," Amendment, filed Oct. 24, 2012, for U.S. Appl. No. 12/900,158, 12 pages.
Eisele et al., "LED Lighting System," U.S. Appl. No. 61/249,858, filed Oct. 8, 2009, 58 pages.
Eisele et al., "LED Lighting System," Notice of Allowance dated Jan. 9, 2013, for U.S. Appl. No. 12/900,158, 9 pages.
European Search Report for EP Application No. 15160578.9, dated Aug. 11, 2015, 8 pages.
Examiner's Report issued in CA Application No. 2,940,766 dated Jan. 11, 2019.
Extended European Search Report and Lack of Unity of Invention Sheet B, dated Jul. 28, 2016, for European Application No. 13833105.3, 17 pages.
Extended European Search Report issued in EP Application No. 17844397.4 dated Jun. 17, 2020 (8 pages).
Extended European Search Report, dated Feb. 1, 2018, for European Application No. 17167920.2-1213, 10 pages.
Extended European Search Report, dated Jul. 12, 2017, for European Application No. 15754628.4-1958, 11 pages.
Extended European Search Report, dated May 28, 2018, for European Application No. 16737803.3-1222/3245631, 7 pages.
Extended European Search Report, dated Nov. 5, 2014, for European Application No. 12779504.5-1352, 6 pages.
Fabrictech International, "PureCare™ Antibacterial Silver," retrieved from http://www.fabrictech.com/shop/purecaresilver.html, retrieved on Aug. 13, 2012, 1 page.
Fabrictech International, "Total Health & Wellness Protection Package—Save 25%," retrieved from http://www.fabrictech.com/shop/custom-package/total-healthawellness-protection.h tml, retrieved on Aug. 13, 2012, 3 pages.
Goodman, "Green Wall Frame," Amendment After Allowance, filed May 11, 2016, for U.S. Appl. No. 29/528,147, 8 pages.
Goodman, "Green Wall Frame," Notice of Allowance, dated Feb. 11, 2016, for U.S. Appl. No. 29/528,147, 11 pages.
GSky Plant Systems, Inc., "Smart Wall Cabinet," 2012, retrieved from http://gsky.com/green-walls/smartwall/, retrieved on Apr. 29, 2015, 3 pages.
International Search Report and the Written Opinion of the International Searching Authority, dated Jun. 8, 2015, for International Application No. PCT/US2015/017528, 20 pages.
International Search Report and Written Opinion of the International Searching Authority, dated Aug. 29, 2016, for International Application No. PCT/US2016/034416, 22 pages.
International Search Report, dated Apr. 28, 2016, for International Application No. PCT/US2016/013215, 5 pages.
International Search Report, dated Dec. 26, 2013, for International Application No. PCT/US2013/057070, 4 pages.
International Search Report, dated Feb. 4, 2011, for International Application No. PCT/US2010/051791, 2 pages.

Japanese Office Action dated Apr. 25, 2017 for JP Application No. 2015-529995, with English summary, 14 pages.
Jernigan, "Light studies focus on circadian rhythms," BioPhotonics, Jul. 2009, retrieved from http://www.photonics.com/Article.aspx?PID=I&VID=43&IID=396&AID=38995, retrieved on Nov. 3, 2014, 2 pages.
Jernigan, R., "Light Studies Focus on Circadian Rhythms," Photonics Showcase, Nov. 2009, p. 12.
Jones, "Chapter 4—Acoustical Treatment for Indoor Areas," in Handbook for Sound Engineers, Ballou (ed.), Burlington, MA, Focal Press, 2008, 65-94.
Land, "Using Vitamin C to Neutralize Chlorine in Water Systems," Recreation Management Tech Tips, Apr. 2005, retrieved from http://www.fs.fed.us/t-d/pubs/html/05231301/05231301.html, retrieved on Mar. 1, 2016, 6 pages.
Macary et al., "Systems, Methods and Articles for Monitoring and Enhancing Human Wellness," U.S. Appl. No. 15/543,114, filed Jul. 12, 2017, 113 pages.
Mold Inspection California, "Killing Mold With Ozone & Thermal Heat," retrieved from http://moldinspectioncalifornia.com/kill_mold_with_ozone.html, 3 pages.
NaturVention, "Science," URL=https://www.naturvention.com/technology-and-science/science/, download date Apr. 5, 2016, 4 pages.
NaturVention, "Technology," URL=https://www.naturvention.com/technology-and-science/, download date Apr. 5, 2016, 6 pages.
Office Action issued in CN Application No. 201580021358.5 dated Feb. 2, 2019.
Office Action, dated May 21, 2018, for U.S. Appl. No. 15/121,953, Pillai et al., "Systems and Articles for Enhancing Wellness Associated With Habitable Environments," 38 pages.
Office Action, dated May 31, 2018, for U.S. Appl. No. 15/421,046, Eisele et al., "LED Lighting System," 9 pages.
Office Action, dated Oct. 27, 2017, for U.S. Appl. No. 15/421,046, Eisele et al., "LED Lighting System," 8 pages.
OxiTitan, "Light Powered Protection," retrieved from http://www.oxititan.com, retrieved on Aug. 13, 2012, 2 pages.
Pervez et al., "Photonic Crystal Spectrometer," U.S. Appl. No. 61/278,773, filed Oct. 12, 2009, 78 pages.
Pervez et al., "Photonic Crystal Spectrometer," U.S. Appl. No. 61/349,570, filed May 28, 2010, 52 pages.
Pillai et al., "Systems, Methods and Articles for Enhancing Wellness Associated With Habitable Environments," Amendment, filed Jul. 21, 2016, for U.S. Appl. No. 14/012,444, 25 pages.
Pillai et al., "Systems, Methods and Articles for Enhancing Wellness Associated With Habitable Environments," Office Action, dated Mar. 22, 2016, for U.S. Appl. No. 14/012,444, 29 pages.
Pillai et al., "Systems, Methods and Articles for Enhancing Wellness Associated With Habitable Environments," Preliminary Amendment, filed Mar. 25, 2015, for U.S. Appl. No. 14/012,444, 149 pages.
Pillai et al., "Systems, Methods and Articles for Enhancing Wellness Associated With Habitable Environments," U.S. Appl. No. 15/409,233, filed Jan. 18, 2017, 84 pages.
Pillai et al., "Systems, Methods and Articles for Enhancing Wellness Associated With Habitable Environments," U.S. Appl. No. 15/421,022, filed Jan. 31, 2017, 84 pages.
Preliminary Amendment, filed Jul. 12, 2017, for U.S. Appl. No. 15/543,114, Macary et al., "Systems, Methods and Articles for Monitoring and Enhancing Human Wellness," 10 pages.
Summons to attend oral proceedings issued in EP Application No. 15754628.4 dated Sep. 10, 2018.
Babyak, Richard J., "Ready to roll," Appliance Manufacturer, 2000, vol. 48, No. 9, pp. 40-42.
Bohn, Hendrik et al., "SIRENA—Service Infrastructure for Real-time Embedded Networked Devices: A service oriented framework for different domains," 2006 (7 pages).
Bourcier, Johann et al., "A Dynamic-SOA Home Control Gateway," 2006 (9 pages).
Chen, Chun-Yuan, "A MOM-based Home Automation Platform in Heterogeneous Environments," A Thesis Submitted to Institute of Computer Science and Engineering College of Computer Science National Chiao Tung University, 2006 (93 pages).

(56) References Cited

OTHER PUBLICATIONS

Dueñas, Juan C. et al., "An End-to-End Service Provisioning Scenario for the Residential Environment," IEEE Communications Magazine, 2005, pp. 94-100.

Jammes, François et al., "Service-Oriented Device Communications Using the Devices Profile for Web Services," 2005 (8 pages).

Kastner, Wolfgang et al., "Communication Systems for Building Automation and Control," Proceedings of the IEEE, 2005, vol. 93, No. 6, pp. 1178-1203.

Messer, Alan et al., "InterPlay: A Middleware for Seamless Device Integration and Task Orchestration in a Networked Home," Proceedings of the Fourth Annual IEEE International Conference on Pervasive Computing and Communications, 2006 (10 pages).

Mingkhwan, A. et al., "Dynamic service composition in home appliance networks," Multimedia Tools and Applications, 2006, vol. 29, pp. 257-284.

Obiltschnig, Günter, "Automatic Configuration and Service Discovery for Networked Smart Devices," Electronica Embedded Conference Munich, 2006 (8 pages).

Rabbie, Harold M., "Distributed Processing Using Local Operating Networks," Assembly Automation, 1992, vol. 12, No. 1 (7 pages).

Saif, Umar, "Architectures for ubiquitous systems," University of Cambridge Computer Laboratory Technical Report No. 527, 2002 (271 pages).

"Proceedings: vol. 1—Indoor Air Quality (IAQ), building related diseases and human response," Healthy Buildings, 2006 (361 pages).

Abt et al., "Characterization of Indoor Particle Sources: A Study Conducted in the Metropolitan Boston Area," Environmental Health Perspectives, 2000, vol. 108, No. 1, pp. 35-44.

Advances in Building Energy Research, 2007, vol. 1 (263 pages).

Ahn, "Synthesis and Characterization of Nanostructured ZnO and SnOx for VOC Sensor Devices," 2011 (204 pages)>.

Amaral et al., "An Overview of Particulate Matter Measurement Instruments," Atmosphere, 2015, vol. 6, pp. 1327-1345.

American Society of Heating, Refrigerating and Air-Conditioning Engineers, Inc., ASHRAE Standard 55-2010: Thermal Environmental Conditions for Human Occupancy (44 pages).

Anderson et al., "Clearing the Air: A Review of the Effects of Particulate Matter Air Pollution on Human Health," Journal of Medical Toxicology, 2012, vol. 8, pp. 166-175.

Arundel et al., "Indirect Health Effects of Relative Humidity in Indoor Environments," Environmental Health Perspectives, 1986, vol. 65, pp. 351-361.

Astolfi et al., "Subjective and objective assessment of acoustical and overall environmental quality in secondary school classrooms," The Journal of the Acoustical Society of America, 2008, vol. 123, No. 1, pp. 163-173.

Atmaca et al., "Effects of radiant temperature on thermal comfort," Building and Environment, 2007, vol. 42, pp. 3210-3220.

Atmaca et al., "Predicting the effect of relative humidity on skin temperature and skin wettedness," Journal of Thermal Biology, 2006, vol. 31, pp. 442-452.

Bekö et al., Ventilation rates in the bedrooms of 500 Danish children, Building and Environment, 2010, vol. 45, pp. 2289-2295.

Bell et al., "The Exposure—Response Curve for Ozone and Risk of Mortality and the Adequacy of Current Ozone Regulations," Environmental Health Perspectives, 2006, vol. 114, No. 4, pp. 532-536.

Braniš et al., "The effect of outdoor air and indoor human activity on mass concentrations of PM10, PM2.5, and PM1 in a classroom," Environmental Research, 2005, vol. 99, pp. 143-149.

Brook et al., "Particulate Matter Air Pollution and Cardiovascular Disease: An Update to the Scientific Statement From the American Heart Association," Circulation: Journal of the American Heart Association, 2010, vol. 121, pp. 2331-2378.

Buchanan et al., "Air filter materials, outdoor ozone and building-related symptoms in the BASE study," Indoor Air, 2008, vol. 18, pp. 144-155.

Carrer et al., "Assessment through Environmental and Biological Measurements of Total Daily Exposure to Volatile Organic Compounds of Office Workers in Milan, Italy," Indoor Air, 2000, vol. 10, pp. 258-268.

Chou, "A Practical Guide to Hazardous Gas Monitors" Occupational Hazards, 2000, vol. 62, No. 9, pp. 61-66.

Chun et al., "Thermal diary: Connecting temperature history to indoor comfort," Building and Environment, 2008, vol. 43, pp. 877-885.

Clements-Croome, "Work performance, productivity and indoor air," Scandinavian Journal of Work Environment & Health, 2008, pp. 69-78.

d'Ambrosio Alfano et al., "On the measurement of the mean radiant temperature and its influence on the indoor thermal environment assessment," Building and Environment, 2013, vol. 63, pp. 79-88.

de Dear et al., "Developing an Adaptive Model of Thermal Comfort and Preference," ASHRAE Transactions, 1998, vol. 104, part 1 (19 pages).

Destaillats et al., "Indoor pollutants emitted by office equipment: A review of reported data and information needs," Atmospheric Environment, 2008, vol. 42, pp. 1371-1388.

Dingle et al., "Formaldehyde Levels and the Factors Affecting These Levels in Homes in Perth, Western Australia," Indoor Built Environment, 2002, vol. 11, pp. 111-116.

Domanico et al., "Documenting the NICU design dilemma: comparative patient progress in open-ward and single family room units," Journal of Perinatology, 2011, vol. 31, pp. 281-288.

Dounis et al., "Design of a fuzzy system for living space thermal-comfort regulation," Applied Energy, 2001, vol. 69, pp. 119-144.

Engvall et al., "Sick building syndrome in relation to building dampness in multi-family residential buildings in Stockholm," International Archives of Occupational and Environmental Health, 2001, vol. 74, pp. 270-278.

Epstein et al., "Thermal Comfort and the Heat Stress Indices," Industrial Health, 2006, vol. 44, pp. 388-398.

Farzaneh et al., "Controlling automobile thermal comfort using optimized fuzzy controller," Applied Thermal Engineering, 2008, vol. 28, pp. 1906-1917.

Fisk, "Estimates Of Potential Nationwide Productivity And Health Benefits From Better Indoor Environments: An Update," Indoor Air Quality Handbook, 1999 (38 pages).

Földváry et al., "Effect of energy renovation on indoor air quality in multifamily residential buildings in Slovakia," Building and Environment, 2017, vol. 122, pp. 363-372.

Frontczak et al., "Literature survey on how different factors influence human comfort in indoor environments," Building and Environment, 2011, vol. 46, pp. 922-937.

GBD 2013 Risk Factors Collaborators, "Global, regional, and national comparative risk assessment of 79 behavioural, environmental and occupational, and metabolic risks or clusters of risks in 188 countries, 1990-2013: a systematic analysis for the Global Burden of Disease Study 2013," The Lancet, 2015, vol. 386, pp. 2287-2323.

Hasan et al., "Sensitivity study for the PMV thermal comfort model and the use of wearable devices biometric data for metabolic rate estimation," Building and Environment, 2016, vol. 110, pp. 173-183.

Hensen, "Literature Review on Thermal Comfort in Transient Conditions," Building and Environment, 1990, vol. 25, No. 4, pp. 309-316.

Howieson et al., "Building tight—ventilating right? How are new air tightness standards affecting indoor air quality in dwellings?" Journal of Building Services Engineering Research & Technology, 2014, vol. 35, No. 5, pp. 475-487.

Huang et al., "A study about the demand for air movement in warm environment," Building and Environment, 2013, vol. 61, pp. 27-33.

Huizenga et al., "Air Quality and Thermal Comfort in Office Buildings: Results of a Large Indoor Environmental Quality Survey," Proceedings of Healthy Buildings, 2006, vol. 3, pp. 393-397.

Humphreys, "Quantifying occupant comfort: are combined indices of the indoor environment practicable?" Building Research & Information, 2005, vol. 33, No. 4, pp. 317-325.

(56) References Cited

OTHER PUBLICATIONS

International Organization for Standardization, "Ergonomics of the thermal environment—Instruments for measuring physical quantities," BS EN ISO 7726, 2nd Edition, 2001 (62 pages).
International Organization for Standardization, "Ergonomics of the thermal environment—Analytical determination and interpretation of thermal comfort using calculation of the PMV and PPD indices and local thermal comfort criteria," ISO 7730, 3rd Edition, 2005 (11 pages).
International Search Report for International Application No. PCT/US2019/050339, dated Nov. 27, 2019 (2 pages).
International Search Report issued in International Application No. PCT/US2019/50416, dated Nov. 27, 2019, 1 p.
Karjalainen et al., "User problems with individual temperature control in offices," Building and Environment, 2007, vol. 42, pp. 2880-2887.
Karjalainen, "Thermal comfort and gender: a literature review," Indoor Air, 2012, vol. 22, pp. 96-109.
Kinney, "Climate Change, Air Quality, and Human Health," American Journal of Preventive Medicine, 2008, vol. 35, No. 5, pp. 459-467.
Klepeis et al., "The National Human Activity Pattern Survey (NHAPS): a resource for assessing exposure to environmental pollutants," Journal of Exposure Analysis and Environmental Epidemiology, 2001, vol. 11, No. 3, pp. 231-252.
Knudsen et al., "Sensory and chemical characterization of VOC emissions from building products: impact of concentration and air velocity," Atmospheric Environment, 1999, vol. 33, pp. 1217-1230.
Korotcenkov et al., "In2O3- and SnO2-Based Thin Film Ozone Sensors: Fundamentals," Journal of Sensors, 2016, vol. 2016 (32 pages).
Lai et al., "An evaluation model for indoor environmental quality (IEQ) acceptance in residential buildings," Energy and Buildings, 2009, vol. 41, pp. 930-936.
Lai et al., "Perceived Importance of the Quality of the Indoor Environment in Commercial Buildings," Indoor and Built Environment, 2007, vol. 16, No. 4, pp. 311-321.
Lai et al., "Perception of importance and performance of the indoor environmental quality of high-rise residential buildings," Building and Environment, 2009, vol. 44, pp. 352-360.
Leidinger et al., "Selective detection of hazardous VOCs for indoor air quality applications using a virtual gas sensor array," Journal of Sensors and Sensor Systems, 2014, vol. 3, pp. 253-263.
Levy et al., "Ozone Exposure and Mortality: An Empiric Bayes Metaregression Analysis," Epidemiology, 2005, vol. 16, No. 4, pp. 458-468.
Lewtas, "Air pollution combustion emissions: Characterization of causative agents and mechanisms associated with cancer, reproductive, and cardiovascular effects," Reviews in Mutation Research, 2007, vol. 636, pp. 95-133.
Licina et al., "Concentrations and Sources of Airborne Particles in a Neonatal Intensive Care Unit," PLOS One, 2016 (17 pages).
Licina et al., "Emission rates and the personal cloud effect associated with particle release from the perihuman environment," Indoor Air, 2017, vol. 27, pp. 791-802.
Liu et al.," Human thermal adaptive behaviour in naturally ventilated offices for different outdoor air temperatures: A case study in Changsha China," Building and Environment, 2012, vol. 50, pp. 76-89.
Liu et al., "A Survey on Gas Sensing Technology," Sensors, 2012, vol. 12, pp. 9635-9665.
Löndahl et al., "A set-up for field studies of respiratory tract deposition of fine and ultrafine particles in humans," Journal of Aerosol Science, 2006, vol. 37, pp. 1152-1163.
Mahyuddin et al., "The spatial distribution of carbon dioxide in rooms with particular application to classrooms," Indoor and Built Environment, 2014, vol. 23, No. 3, pp. 433-448.
Massey et al., "Emission and Formation of Fine Particles from Hardcopy Devices: the Cause of Indoor Air Pollution," Monitoring, Control and Effects of Air Pollution, 2001, pp. 121-134.

McCullough et al., "Determining temperature ratings for children's cold weather clothing," Applied Ergonomics, 2009, vol. 40, pp. 870-877.
McIntyre, "Response to Atmospheric Humidity at Comfortable Air Temperature: A Comparison of Three Experiments," Annals of Occupational Hygiene, 1978, vol. 21, pp. 177-190.
Mendell et al., "Improving the Health of Workers in Indoor Environments: Priority Research Needs for a National Occupational Research Agenda," American Journal of Public Health, 2002, vol. 92, No. 9, pp. 1430-1440.
Newsham, "Clothing as a thermal comfort moderator and the effect on energy consumption," Energy and Buildings, 1997, vol. 26, pp. 283-291.
Nicol et al., "A critique of European Standard EN 15251: strengths, weaknesses and lessons for future standards," Building Research & Information, 2011, vol. 39, No. 2, pp. 183-193.
Novoselac et al., "A critical review on the performance and design of combined cooled ceiling and displacement ventilation systems," Energy and Buildings, 2002, vol. 34, pp. 497-509.
Ormandy et al., "Health and thermal comfort: From WHO guidance to housing strategies," Energy Policy, 2012, vol. 49, pp. 116-121.
Painter et al., "Practical application of a sensor overlay system for building monitoring and commissioning," Energy and Buildings, 2012, vol. 48, pp. 29-39.
Park et al., "Variations of formaldehyde and VOC levels during 3 years in new and older homes," Indoor Air, 2006, vol. 16, pp. 129-135.
Persily, "Evaluating Building IAQ and Ventilation with Indoor Carbon Dioxide," ASHRAE Transactions, 1997, vol. 103 (12 pages).
Revel et al., "Integration of real-time metabolic rate measurement in a low-cost tool for the thermal comfort monitoring in AAL environments," Ambient Assisted Living, 2015 (11 pages).
Salthammer et al. "Formaldehyde in the Indoor Environment," Chemical Reviews, 2010, vol. 110, No. 4, pp. 2536-2572.
Sandberg et al., "Experimental Methods in Ventilation," Advances in Building Energy Research, 2008, vol. 2, No. 1, pp. 159-210.
Satish et al., "Is CO2 an Indoor Pollutant? Direct Effects of Low-to-Moderate CO2 Concentrations on Human Decision-Making Performance," Environmental Health Perspectives, 2012, vol. 120, No. 12, pp. 1671-1677.
Schellen et al., "Differences between young adults and elderly in thermal comfort, productivity, and thermal physiology in response to a moderate temperature drift and a steady-state condition," Indoor Air, 2010, vol. 20, pp. 273-283.
Schlegel, "The Relative Effects of Convection And Radiation Heat Transfer on the Thermal Sensations of Sedentary Subjects," 1968 (73 pages).
Seppänen et al., "Association of Ventilation Rates and CO2 Concentrations with Health and Other Responses in Commercial and Institutional Buildings," Indoor Air, 1999, vol. 9, pp. 226-252.
Seppänen et al., "Summary of human responses to ventilation," Indoor Air, 2004, vol. 14, pp. 102-118.
Siemens, "Demand-controlled ventilation: Control strategy and applications for energy-efficient operation," publicly available at least as early as May 21, 2018 (72 pages).
Song, "Could sperm quality be affected by a building environment? A literature review," Building and Environment, 2010, vol. 45, pp. 936-943.
Spinellis, "The information furnace: consolidated home control," Personal and Ubiquitous Computing, 2003, vol. 7, pp. 53-69.
Strauss et al., "Influence of Heat and Humidity on the Airway Obstruction Induced by Exercise in Asthma," The Journal of Clinical Investigation, 1978, vol. 61, pp. 433-440.
Szigeti et al., "Spatial and temporal variation of particulate matter characteristics within office buildings—The OFFICAIR study," Science of the Total Environment, 2017, vol. 587-588, pp. 59-67.
Uğursal et al., "The effect of temperature, metabolic rate and dynamic localized airflow on thermal comfort," Applied Energy, 2013, vol. 111, pp. 64-73.
Vastamäki et al., "A behavioural model of temperature controller usage and energy saving," Personal and Ubiquitous Computing, 2005, vol. 9, pp. 250-259.

(56) References Cited

OTHER PUBLICATIONS

Wargocki et al., "Ten questions concerning thermal and indoor air quality effects on the performance of office work and schoolwork," Building and Environment, 2017, vol. 112, pp. 359-366.
Wargocki et al., "The Effects of Outdoor Air Supply Rate in an Office on Perceived Air Quality, Sick Building Syndrome (SBS) Symptoms and Productivity," Indoor Air, 2000, vol. 10, pp. 222-236.
Weschler, "Ozone in Indoor Environments: Concentration and Chemistry," Indoor Air, 2000, vol. 10, pp. 269-288.
Weschler, "Ozone's Impact on Public Health: Contributions from Indoor Exposures to Ozone and Products of Ozone-Initiated Chemistry," Environmental Health Perspectives, 2006, vol. 114, No. 10, pp. 1489-1496.
Williams et al., Next Generation Air Monitor (NGAM) VOC Sensor Evaluation Report, EPA/600/R-15/122, 2015(71 pages).
Wisthaler et al., "Reactions of ozone with human skin lipids: Sources of carbonyls, dicarbonyls, and hydroxycarbonyls in indoor air," Proceedings of the National Academy of Sciences, 2010, vol. 107, No. 15, pp. 6568-6575.
Wolkoff, "Impact of Air Velocity, Temperature, Humidity, and Air On Long-Term VOC Emissions From Building Products," Atmospheric Environment, 1998, vol. 32, No. 14/15, pp. 2659-2668.
Won et al., "The State-of-the-Art in Sensor Technology for Demand-Controlled Ventilation, PERD S5-42: Final Report," IRC-RR-243, NRC Publications Archive, 2005 (89 pages).
Wong et al., "A multivariate-logistic model for acceptance of indoor environmental quality (IEQ) in offices," Building and Environment, 2008, vol. 48, pp. 1-6.
Xiong et al., "Potential indicators for the effect of temperature steps on human health and thermal comfort," Energy and Buildings, 2016, vol. 113, pp. 87-98.
Yu et al., "People who live in a cold climate: thermal adaptation differences based on availability of heating," Indoor Air, 2013, vol. 23, pp. 303-310.
Zhang et al., "Study on TVOCs concentration distribution and evaluation of inhaled air quality under a re-circulated ventilation system," Building and Environment, 2007, vol. 42, pp. 1110-1118.
Zhang et al., "Thermal comfort in naturally ventilated buildings in hot-humid area of China," Building and Environment, 2010, vol. 45, pp. 2562-2570.
Zhao et al., "Effect of particle spatial distribution on particle deposition in ventilation rooms," Journal of Hazardous Materials, 2009, vol. 170, pp. 449-456.
Zhou et al., "Experimental study of the influence of anticipated control on human thermal sensation and thermal comfort," Indoor Air, 2014, vol. 24, pp. 171-177.
Akacem et al., "Bedtime and evening light exposure influence circadian timing in preschoolage children: A field study," Neurobiology of Sleep and Circadian Rhythms, 2016, vol. 1, pp. 27-31.
Akacem et al., "Sensitivity of the circadian system to evening bright light in preschool-age children," Physiological Reports, 2018, vol. 6, No. 5, pp. 1-10.
Cho et al., "Effects of artificial light at night on human health: A literature review of observational and experimental studies applied to exposure assessment," Chronobiology International: The Journal of Biological and Medical Rhythm Research, 2015, pp. 1-17.
Dijk et al., "Light, Sleep, and Circadian Rhythms: Together Again," PLoS Biology, 2009, vol. 7, No. 6, pp. 1-4.
Exelmans et al., "Bedtime mobile phone use and sleep in adults," Social Science & Medicine, 2016, vol. 148, pp. 93-101.
Fonken et al., "Dim Light at Night Disrupts Molecular Circadian Rhythms and Affects Metabolism," Journal of Biological Rhythms, Author Manuscript, 2013, vol. 28, No. 4 (15 pages).
Fossum et al., "The Association Between Use of Electronic Media in Bed Before Going to Sleep and Insomnia Symptoms, Daytime Sleepiness, Morningness, and Chronotype," Behavioral Sleep Medicine, 2014, vol. 12, pp. 343-357.
Grønli et al., "Reading from an iPad or from a book in bed: the impact on human sleep. A randomized controlled crossover trial," Sleep Medicine, 2016, vol. 21, pp. 86-92.
Hafner et al., Why sleep matters—the economic costs of insufficient sleep: A cross-country comparative analysis, 2016 (101 pages).
Hysing et al., "Sleep and use of electronic devices in adolescence: results from a large population-based study," BMJ Open, 2015, vol. 5, pp. 1-7.
Joshi et al., "The importance of temperature and thermoregulation for optimal human sleep," Energy and Buildings, 2016, vol. 131, pp. 153-157.
Lan et al., "Ten questions concerning thermal environment and sleep quality," Building and Environment, 2016, vol. 99, pp. 252-259.
Marinelli et al., "Hours of Television Viewing and Sleep Duration in Children: A Multicenter Birth Cohort Study," JAMA Pediatrics, 2014, vol. 168, No. 5, pp. 458-464.
Peuhkuri et al., "Diet promotes sleep duration and quality," Nutrition Research, 2012, vol. 32, pp. 309-319.
Potter et al., "Circadian Rhythm and Sleep Disruption: Causes, Metabolic Consequences, and Countermeasures," Endocrine Reviews, 2016, vol. 37, No. 6, pp. 584-608.
Strøm-Tejsen et al., "The effects of bedroom air quality on sleep and next-day performance," Indoor Air, 2016, vol. 26, pp. 679-686.
Watson et al., "Recommended Amount of Sleep for a Healthy Adult: A Joint Consensus Statement of the American Academy of Sleep Medicine and Sleep Research Society," Sleep, 2015, vol. 38, No. 6, pp. 843-844.
Yadlapalli et al., "Circadian clock neurons constantly monitor environmental temperature to set sleep timing," Nature, 2018, vol. 555 (21 pages).
Yetish et al., "Natural sleep and its seasonal variations in three pre-industrial societies," Current Biology, Author Manuscript, 2015, vol. 25, No. 21 (19 pages).

* cited by examiner

500 ⇢

| Provide signals to vary illumination passed by pane(s) of electrochromatic material | ⌐ 502 |

| Provide signals to control electrical motor drivingly coupled to move shade(s)/curtain(s) | ⌐ 602 |

FIG. 6

SYSTEMS, METHODS AND ARTICLES FOR ENHANCING WELLNESS ASSOCIATED WITH HABITABLE ENVIRONMENTS

CROSS-REFERENCE TO RELATED APPLICATIONS

This application is a U.S. national phase application filed under 35 U.S.C. § 371 of International Application PCT/US2017/048382, filed Aug. 24, 2017, designating the United States, which claims the benefit of U.S. Provisional Application No. 62/379,079, filed Aug. 24, 2016, and claims the benefit of U.S. Provisional Application No. 62/379,086, filed Aug. 24, 2016, which are hereby incorporated by reference herein in their entirety.

FIELD

This disclosure generally relates to habitable environments, for instance homes, hotel or motels, offices and hospitals, and particularly to techniques for enhancing human habitation in such environments.

BACKGROUND

Most people spend significant amounts of time in habitable environments such as enclosed spaces associated with homes, apartments, condominium units, hotel suites or rooms, motel suites or rooms, spas, hospital, and other public and private facilities. Sometimes these enclosed spaces are controlled, or even owned by, the principal occupants, such as homes, apartments or condominium units. Other times these enclosed spaces are controlled by others, for example a facility owner or operator who may own and/or operate a hotel, motel, spa, hospital.

Significant time in these spaces exposes the occupant to a wide range of environmental factors, any of which may have either adverse or beneficial effects on the occupant's health, well-being or sense of well-being. Minimizing exposure to environmental factors that tend to have an adverse effect is desirable, as is increasing exposure to environmental factors that tend to have a beneficial effect.

New approaches that enhance habitable environments are desirable.

BRIEF SUMMARY

Products, methods and systems may be usable for controlling lighting color temperature, lighting intensity, illuminance, light source direction, humidity, air temperature, air temperature distribution, air pressure, air flow, air quality, aroma, air particle count, sound level, water quality, scent or aroma, and other environment conditions or other parameters within a particular space or other habitable environment. Such spaces may include, for example, an office building, school, apartment building, dormitory, single family home, multi-family dwelling or building, townhouse, theatre, train or bus station, library, public lounge, store or market, bakery, restaurant, tavern, pub, resort, bar, hostel, lodge, hotel, motel, inn, guest house, mall, art gallery, art studio, craft studio, ship, boat, gym, spa, fitness center, sports facility, gas station, airplane, airport, automobile, train, bus, kiosk, hospital, doctor's office, dentist's office, police station, fire station, light house, bank, coffee shop, dry cleaner, department store, pharmacy, hardware store, drug store, grocery store, institution, music studio, recording studio, concert hall, radio station or studio, television station or studio, post office, church, mosque, synagogue, chapel, mobile home, barn, farm house, silo, residence, assisted living center, hospice, dwelling, laundromat, museum, hair salon, parking structure or facility, green house, nursery, nail salon, barbershop, trailer, warehouse, storage facility, rest home, day care facility, laboratory, military facility, and any other place or facility where one or more people may congregate, live, work, spend time, etc. Within such spaces, there may be one or more sub-spaces or habitable environments that may be used for single or multiple purposes, such as home or other offices, kitchens, galleys, pantries, cooking areas, eating areas, home or office libraries or studies, conference rooms, dining rooms, bathrooms, toilets, powder rooms, play rooms, bedrooms, foyers, reception areas, file rooms, pods, pet rooms, storage rooms, junk rooms, carports, dens, basements, attics, garages, closets, classrooms, cabins, cabooses, train cars, bunk rooms, media rooms, baths, auditoriums, locker rooms, changing rooms, engine rooms, cockpits, work rooms, stairwells, exhibition rooms, platforms, elevators, walk ways, hallways, pools, stock rooms, exercise rooms, break rooms, snack rooms, living or family rooms, dressing rooms, lumber rooms, meeting rooms, conference rooms, game rooms, porches, patios, seating areas, clean rooms, common rooms, lunch rooms, sky boxes, stages, prop rooms, make up rooms, safes, vaults, reception areas, check-in areas, compartments, drafting rooms, drawing rooms, computer or information technology rooms, waiting rooms, operating rooms, examination rooms, therapy rooms, emergency rooms, recovery rooms, machine rooms, equipment rooms, control rooms, laboratory rooms, monitoring rooms, and enclosed or partially enclosed areas, among others.

Various approaches described herein employ combinations of passive and active techniques for enhancing environmental characteristics of inhabitable environments, to reduce or ameliorate adverse effects and to increase beneficial effects. These approaches may have application in occupational environments, for instance offices, retail locations, factories or warehouses. These approaches may have application in residential settings, for instance homes, apartments, porches, condominiums or other residences. These approaches may have application in other settings, for instance hospitals or clinics, waiting areas associated with transportation such as airports and train stations, and/or public areas such as theaters, arenas, stadiums, museums and other venues. The various combinations may advantageously produce synergistic results, which may not be otherwise achievable on an individual basis.

Occupants or other users of such spaces or sub-spaces may want to control or influence the environmental conditions or other parameters within a given space or sub-space, which may be or be part of a habitable environment or other habitable, usable or occupiable area. This may include establishing, transitioning to, changing, starting or ending a scene for the space or sub-space. For example, a user may want to enhance, facilitate or improve the user's and/or one or more other person's ability or likelihood to relax, get energized, fall asleep, improve sleep, overcome jet lag, focus, play, exercise, wake up, reduce stress, reduce fatigue, change current habit or pattern, build or create a healthy habit, change current routine or mood, improve health or wellness, etc. within a space or sub-space.

For example, a user in a home may want environmental parameters or a scene to be set or adjusted within the user's bedroom so that the user falls asleep faster or wakes up faster, within the user's home or work office so that the user can focus on work tasks, within the user's classroom to encourage focus by students therein, within the user's gym so that the user is more energized.

In one illustrative approach, a system to control environmental characteristics in an enclosed space may be summarized as including a control subsystem that includes at least one processor and at least one nontransitory processor-readable medium that stores at least one of processor-executable instructions or data; an illumination subsystem operable to control illumination characteristics of illumination provided in at least a portion of the enclosed spaced, the illumination subsystem including: a plurality of illumination sources selectively operable to emit illumination at a number of levels and a number of wavelengths; at least one actuator operable to control an amount of illumination received into the enclosed space via one or more windows from an external source of illumination; and at least one user actuatable input device located in the enclosed space and communicatively coupled to the control subsystem and selectively actuatable by a user to switch between a circadian setting and at least one override setting, wherein: the control subsystem is communicatively coupled to control the plurality of illumination sources and the at least one actuator, and when in the circadian setting the control subsystem provides signals to the illumination sources and the at least one actuator to cause the illumination sources and the at least one actuator to provide illumination according to a defined circadian pattern over a period of time, the circadian pattern at least approximately matching changes in illumination level and color temperature of naturally occurring illumination of at least one defined latitude over the period of time.

In some embodiments, the control subsystem includes sensors to measure lux levels and color temperature at different areas of the home to understand what effect outdoor light has on the desired outcome for the indoor space. Based on data from the artificial light setting and the sensor data from the indoor conditions, the artificial light changes to match the desired lux levels and color temperature. If there is significant natural light during the day near the window, the lights in that area may turn off since the desired setting is achieved fully through natural light.

Exposure to light at night during sleep time—even in minute quantities—can have dramatic impacts on the circadian rhythm. Especially in urban settings, light pollution at night has become a major concern for human health. While indoor lighting can be easily controlled by occupants, it is also important to provide means for occupants to minimize light from outdoors through fenestrations.

Blackout shades are typically used to help minimize outdoor light intrusions during night time, including but not limited to roller shades, cellular shades and drapery shades. At least one actuator may include electrochromatic glass in the at least one window. At least one actuator may include an electric motor physically coupled to a transmission that selectively positions at least one blackout shade across the at least one window. In a night portion of the circadian pattern, the control subsystem may provide signals to at least a subset of the illumination sources which are, for example solid-state illumination sources or small incandescent lights to produce a low level of illumination proximate at least one path to a door of the enclosed space. When in a first override setting of the at least one override setting the control subsystem may provide signals to the illumination sources and the at least one actuator to cause the illumination sources and the at least one actuator to provide illumination that does not follow the defined circadian pattern. When in a second override setting of the at least one override setting the control subsystem may provide signals to the illumination sources and the at least one actuator to cause the illumination sources and the at least one actuator to provide illumination to the enclosed space based at least in part on a geographic location from where an occupant of the enclosed spaced originated to accommodate a change in circadian rhythm due to travel by the occupant. When in a third override setting of the at least one override setting the control subsystem may provide signals to the illumination sources and the at least one actuator to cause the illumination sources and the at least one actuator to provide illumination to the enclosed space based at least in part on a time of year to accommodate a change in circadian rhythm due to seasonal variation at a geographic location of the enclosed space. When in yet another override setting of the at least one override setting the control subsystem may provide signals to the illumination sources and the at least one actuator to cause the illumination sources and the at least one actuator to provide illumination to the enclosed space to produce a therapeutic effect in an occupant of the enclosed space. The system may further include at least one sensor positioned to detect presence of an occupant in the enclosed spaced and communicatively coupled to the control subsystem to provide signals indicative of a current occupancy condition of the enclosed space. The system may further include at least one user actuatable input device located remotely from the enclosed space and communicatively coupled to the control subsystem and selectively actuatable to switch between a plurality of settings for the system. The system may further include an air handling subsystem to control air characteristics of air in the enclosed space, the air handling system including at least one of: an air filter, a heater, an air conditioner, a humidifier, a dehumidifier, a vent, a fan, or a compressor, and the air handling system including at least one of: a temperature sensor or a humidity sensor positioned to detect a temperature or a humidity proximate at least one portion of the enclosed space. The control subsystem may provide signals to at least one portion of the air handling subsystem to control at least one of the temperature or the humidity of air in the enclosed space. The control subsystem may provide signals to adjust at least the temperature of the air in the enclosed space based at least in part on the circadian pattern over the period of time. The at least one air filter may include at least one of: a HEPA mechanical air filter, an electrostatic particle air filter, or an ultraviolet air filter. The air handling subsystem may further include a number of inlets for selectively introducing scents into the air in the enclosed space from a number of reservoirs and the control subsystem may provide signals to at least one portion of the air handling subsystem to control the introduction of the scents into the air in the enclosed space. The control subsystem may provide signals to at least one portion of the air handling subsystem to control the introduction of the scents into the air in the enclosed space based on a defined schedule. The control subsystem may provide signals to at least one portion of the air handling subsystem to control the introduction of the scents into the air in the enclosed space on demand in response to a user input. The system may further include a water supply subsystem including a sediment filter and an activated charcoal filter that filters water that is to be supplied to the enclosed space via a faucet or a showerhead. The water supply subsystem may further include an ultraviolet water sanitizer that illuminates water that is to be supplied to the enclosed space via a faucet or a showerhead with ultraviolet illumination. The water supply subsystem may further include an inlet to supply vitamin C to water that is to be supplied to the enclosed space via a showerhead. The system may further include an ambient sound subsystem, that may include at least one piece of acoustic insulation positioned to acoustically insulate at least some of a number of plumbing components; at least one acoustic damping door that acoustically insulates the enclosed space from an exterior thereof when the at least one acoustic damping door is in a closed position; at least one acoustic damping window that acoustically insulates the enclosed space from the exterior thereof when the at least one acoustic damping window is in a closed position; at least one acoustic damping walling component that acoustically insulates the enclosed space from the exterior thereof; and at least one acoustic damping flooring component that acoustically insulates the enclosed space from the exterior thereof. An ambient sound level in the enclosed space may be less than 45 dB when active source of sound is operating in the enclosed space. The system may further include at least one speaker communicatively coupled to be controlled by the control subsystem to play sound in the enclosed space at a sound level that changes in synchronization with a change in a level of illumination emitted by the illumination sources. The control subsystem may provide signals to gradually increase both the sound and illumination levels in response to an occurrence of a pre-set time. The system may further include a cushioned low volatile organic compound emitting flooring in the enclosed space. The system may further include a textured reflexology flooring path in the enclosed space. The system may further include at least one electromagnetic field shield positioned relative to wiring to reduce a level of electromagnetic field introduced into the enclosed space by the wiring.

In addition to vision, light may influence the human body in a number of ways to which people respond subconsciously, including mood, alertness, and cognitive ability. Humans and animals have an internal clock that keeps the body on a roughly 24-hour cycle, in what is called the circadian rhythm. Multiple bodily processes, including sleep and digestion are regulated in part by the daily hormonal fluctuations of the circadian rhythm. These hormones are released by an area in the brain called the hypothalamus. The hypothalamus times its hormonal outputs based on the timing of light exposure, which it receives via specialized cells in the eye, called ipRGCs. Daily, regularly-timed light exposure is required to maintain a healthy and robust circadian rhythm, called "entrainment".

A method of controlling environmental characteristics in an enclosed space may be summarized as including receiving at a first time a first input indicative of a selection of a circadian setting; in response to the first input indicative of the selection of the circadian setting, providing signals by a control subsystem to cause a plurality of illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination varies over a first period of time according to a circadian pattern; receiving at a second time a second input indicative of a selection of a first non-circadian setting; and in response to the second input indicative of the selection of the first non-circadian setting, providing signals by the control subsystem to cause a plurality of illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination does not vary over a second period of time according to the circadian pattern.

In response to the second input indicative of the selection of the first non-circadian setting, the control subsystem may provide signals to the plurality of illumination sources and the at least one actuator such that the combination of the artificial and the natural illumination remains constant over the second period of time. The method may further include receiving at a third time a third input indicative of a selection of a second non-circadian setting that is a sleep time setting; and in response to the third input indicative of the second non-circadian setting that is the sleep time setting, providing signals by the control subsystem to cause a subset of the illumination sources proximate to a floor in the enclosed space to emit artificial illumination at a low illumination level along at least one path and to cause the at least one actuator to prevent natural illumination from being received into the enclosed space via the one or more windows. The method may further include receiving at a fourth time a fourth input indicative of a selection of a travel adjustment setting; in response to the fourth input indicative of the travel adjustment setting: determining a travel adjustment illumination pattern (also referred to as a scene) based at least in part on a geographic location from where an occupant of the enclosed spaced originated to accommodate a change in circadian rhythm due to travel by the occupant; and providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the determined travel adjustment illumination pattern or scene in the enclosed space. The method may further include receiving at a fourth time a fourth input indicative of a selection of a light therapy setting; and in response to the fourth input indicative of the light setting, providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the defined light therapy illumination pattern or scene in the enclosed space over a therapeutic period of time. Providing signals by the control subsystem to cause the at least one actuator to control at least the level of natural illumination received into the enclosed space via the one or more windows may include providing signals to vary an amount of illumination passed by at least one pane of electrochromatic material. Providing signals by the control subsystem to cause the at least one actuator to control at least the level of natural illumination received into the enclosed space via the one or more windows may include providing signals to control an electrical motor drivingly coupled to move at least one of a shade or a curtain relative to the at least one window. The method may further include detecting by at least one sensor whether the enclosed spaced is occupied; and providing signals to the control subsystem indicative of whether the enclosed space is occupied. The method may further include receiving input by at least one user actuatable input device located remotely from the enclosed space; and providing signals to the control subsystem indicative of the received input. The method may further include providing signals by the control subsystem to at least one component of an air handling subsystem to control air characteristics of air in the enclosed space. Providing signals to at least one component of the air handling subsystem may include providing signals to at least one of an air filter, a heater, an air conditioner, a humidifier, a dehumidifier, a vent, a fan, or a compressor to control at least one of the temperature or the humidity of air in the enclosed space. The method may further include receiving signals by the control subsystem from at least one of: a temperature sensor or a humidity sensor positioned to detect a temperature or a humidity proximate at least one portion of the enclosed space. Providing signals to at least one component of the air handling subsystem may include providing signals to adjust at least a temperature of the air in the enclosed space based at least in part on the circadian pattern or scene over the period of time. The method may further include filtering air for the enclosed space with at least one of: a HEPA mechanical air filter, an electrostatic particle air filter, or an ultraviolet air filter. The method may further include providing signals by the control subsystem to selectively introduce scents into the air in the enclosed space from a number of reservoirs. Providing signals by the control subsystem to selectively introduce scents into the air in the enclosed space may include providing signals based on a defined schedule. Providing signals by the control subsystem to selectively introduce scents into the air in the enclosed space may include providing signals based on demand in response to a user input. The method may further include filtering a supply of water to a faucet or a showerhead of the enclosed space via a water supply subsystem including at least one of a sediment filter or an activated charcoal filter, and exposing the water to ultraviolet illumination to sanitize the water. The method may further include introducing vitamin C into water that is to be supplied to the showerhead of the enclosed space. The method may further include supplying signals by the controller subsystem to at least one speaker to play sound in the enclosed space at a sound level that changes in synchronization with a change in a level of illumination emitted by the illumination sources.

In another illustrative approach, a system to enhance environmental characteristics in a habitable environment may be summarized as including at least one acoustic damping window that acoustically insulates the habitable environment from the exterior thereof when the at least one acoustic damping window is in a closed position; at least one acoustic damping walling component that acoustically insulates the habitable environment from the exterior thereof; at least one acoustic damping flooring component that acoustically insulates the habitable environment from the exterior thereof; and at least one speaker selectively operable to play sound in the habitable environment. The American Academy of Sleep Medicine and the Sleep Research Society recommend at least seven hours of sleep per night for adults aged 18-60 years old to promote optimal health and well-being. Sleep is one of the body's most critical activities and there are wide ranges of environmental factors that can impact it. For example, noise at night can make it difficult to fall asleep and can create short disturbances of natural sleep patterns by causing shifts from deep to lighter stages. Since most people get the majority of their sleep in their home, a bedroom conducive to healthy and restorative rest requires the creation of a quiet environment. In the bedroom, utilizing materials with a high sound transmission class and high sound reduction index can minimize noise intrusion from outside the bedroom and outside the home.

The system may further include a plurality of illumination sources selectively operable to emit artificial illumination at a number of levels and a number of wavelengths in the habitable environment; at least one actuator operable to control an amount of illumination received into the habitable environment via one or more windows from an external source of natural illumination. The system may further include a control subsystem communicatively coupled to control the plurality of illumination sources, the at least one actuator, and the at least one speaker. The system may further include at least one acoustic damping door that acoustically insulates the habitable environment from an exterior thereof when the at least one acoustic damping door is in a closed position. The system may further include a photocatalyst antimicrobial agent on at least one surface in the habitable environment.

By one approach, a method of controlling environmental characteristics in a habitable environment may be summarized as including distributing an antimicrobial agent in the habitable environment prior to occupancy of the habitable environment by a first occupant; subjecting surfaces in the habitable environment to ultraviolet illumination prior to occupancy of the habitable environment by the first occupant; applying antimicrobial bedding to a bed in the habitable environment prior to occupancy of the habitable environment by the first occupant; and setting an illumination pattern (also referred to as a scene) that controls both artificial and natural illumination provided in the habitable environment based on at least one characteristic of the first occupant.

The method may further include setting a sound pattern or scene that controls artificial sound provided in the habitable environment based on at least one characteristic of the first occupant. Setting a sound pattern or scene may include setting a sound pattern that is synchronized at least in part to the illumination pattern or scene that controls both artificial and natural illumination provided in the habitable environment based on at least one characteristic of the first occupant. The method may further include removing the antimicrobial agent from the habitable environment prior to occupancy of the habitable environment by the first occupant. Distributing an antimicrobial agent in the habitable environment may include distributing a photocatalytic antimicrobial agent; and may further include exposing the antimicrobial agent to a defined wavelength of illumination for a defined time prior to occupancy of the habitable environment by the first occupant. The method may further include providing treated water to the habitable environment.

By one approach, an environment control system may include sensor(s) or other transducer devices configured to monitor environmental condition(s) of a space (or portion thereof), controllable device(s) configured to adjust the environmental condition(s) of the space, a scene database with a plurality of scenes therein, each of the scenes having environmental parameter settings associated therewith, the environmental parameter settings being adjusted via the one or more controllable devices, and a control circuit in communication with the one or more sensors, the one or more controllable devices, and the scene database. In one illustrative approach, the control circuit is configured to receive measurement(s) of the environmental condition(s) from the sensor(s) or other transducer devices, receive notice of or detect a particular condition prompting adjustment of the monitored environmental condition(s) or a request to transition to a particular scene, and instruct the controllable device(s) to adjust the environmental condition(s) of the space (or portion thereof) to render the environmental condition(s) within the environmental parameter settings associated with the particular scene. As used herein, the environmental conditions may include at least one of: air conditions, temperature conditions, water conditions, lighting conditions, aroma conditions, and sound conditions. In one exemplary approach, the scene database further includes scene transition data for transitioning the controllable device(s) and the environmental condition(s) of the space (or portion or sub-space thereof) from a first active scene to a second scene. In one form, the controllable device controls two of the environmental conditions listed above, or two parameters related to the same condition, such as two parameters both related to lighting conditions, water conditions, aroma conditions, or noise conditions. Alternatively, the controllable device controls two parameters related to different conditions, such as one parameter relating to lighting condition and a second parameter related to air condition, water condition, aroma condition, or noise condition. Or another combination of the two conditions listed above.

By another approach, the environment control system may further include an electronic user device configured to receive inputs from a user regarding a particular one of the scenes. In this manner, the control circuit may receive a scene request form the electronic user device and instruct the controllable device(s) to adjust the environmental condition(s) of the space (or portion thereof) to render the environmental condition(s) within the environmental parameter settings associated with the particular requested scene.

In yet another approach, the adjustment of the scenes may occur in response to detection of a particular condition such as, for example, a time of day, a change of a number of occupants, space configuration, device setting, a user input, external environment factors, specific internal condition, and automatic or other input received from a wearable sensor.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 5 is a flow diagram that shows a low level method of operating one or more components of a habitable environment enhancement system to adjust an amount of natural light received in the habitable environment using electrochromatic panes, according to one illustrated embodiment, which may be useful in performing at least a portion of the method illustrated in FIG. 4.

FIG. 6 is a flow diagram that shows a low level method of operating one or more components of a habitable environment enhancement system to adjust an amount of natural light received in the habitable environment using drapes, shades or curtains, according to one illustrated embodiment, which may be useful in performing at least a portion of the method illustrated in FIG. 4.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with environmental control such as fans, blowers, heaters, coolers such as air conditioners or swamp coolers, compressors, and control systems such as computing systems, as well as networks and other communications channels have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Environment Overview

Figure 1:
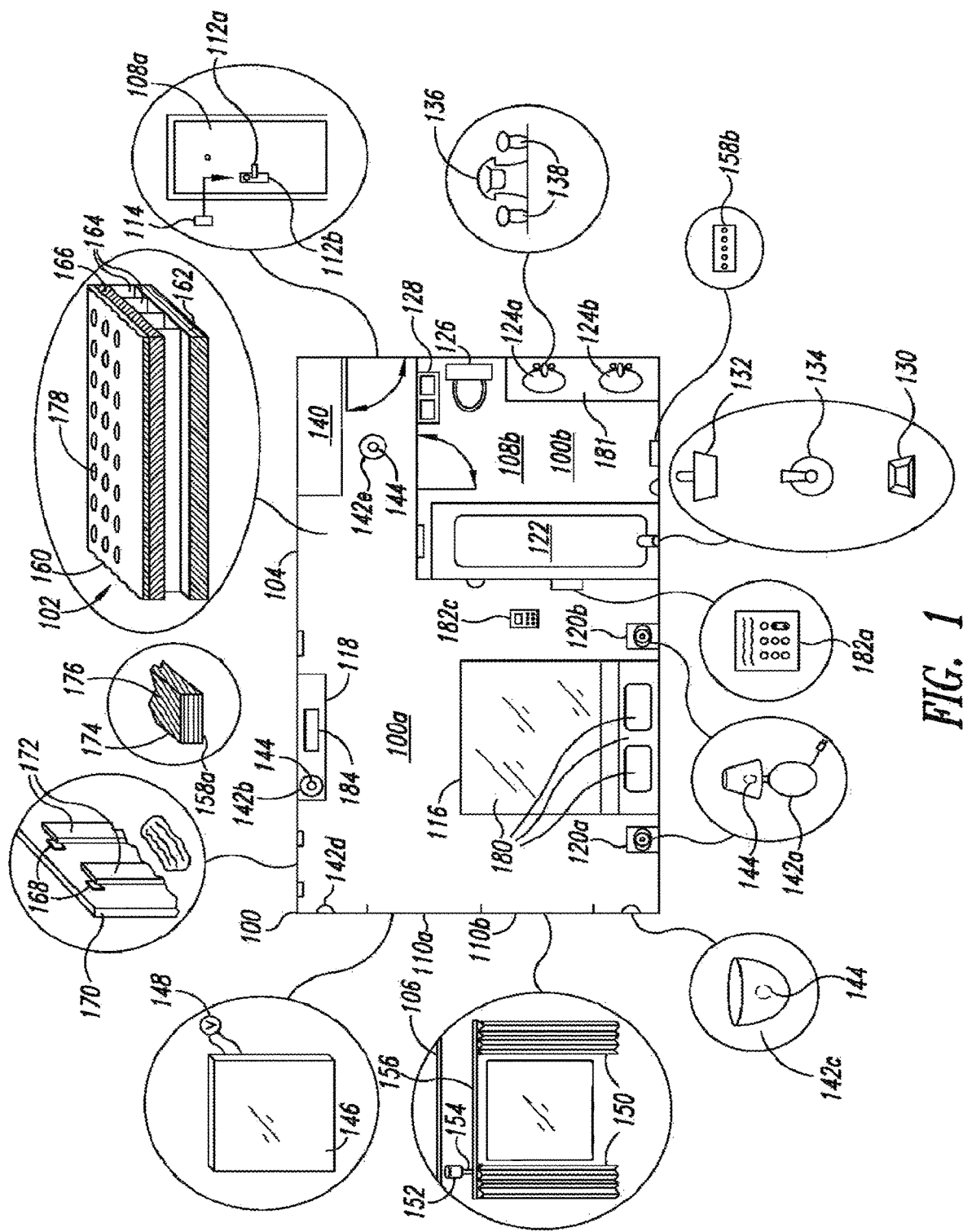
FIG. 1 is a schematic diagram of a habitable environment according to one illustrated embodiment, including enlarged views of various elements or components of the habitable environment.

FIG. 1 shows a habitable environment 100, according to one illustrated embodiment in which various apparatus, methods and articles described herein may operate.

The habitable environment 100 may take the form of one or more enclosed spaces, such as one or more rooms, for instance in a house, hotel, spa, condominium unit, apartment, office, hospital, or other accommodation which people typically inhabit, and other areas such as those described below in regards to spaces and sub-spaces. As used herein, the terms "spaces" and "sub-spaces" may be the habitable space 100, may include some or all of the habitable environment 100, or may be other areas where one or more people or living things may congregate, live, work, play, eat, exercise, occupy, etc.

The habitable environment 100 includes a floor system 102, wall system 104, and ceiling system 106, and may include one or more doors 108a, 108b (collectively 108) and/or windows 110a, 110b (collectively 110). The doors 108 may provide ingress and egress to an exterior environment, or may provide ingress and egress to other enclosed spaces within the habitable environment 100. For instance, one door 108a may provide passage between the habitable environment 100 and a hallway (not called out) outside of the habitable environment 100. Another door 108b may provide passage between one portion and another portion of the habitable environment 100, such as between a bedroom or living area 100a and a bathroom 100b.

The door 108a to the exterior may have a handle 112a with associated lock, for instance a cardkey entry lock 112b. Card key entry lock 112b reads an identifier either encoded in a magnetic stripe or in a wireless transponder (e.g., radio frequency identification or RFID transponder or smartcard) of a cardkey 114. The identifier may be logically associated with an inhabitant or occupant of the habitable environment 100. For example, a hotel guest may be assigned to a given suite, and issued a cardkey 114 that provides access to the suite. The identity of the guest may be stored in a database or other data structure with a logical relationship (e.g., key, pointer) to the suite. Likewise, various attributes of the guest may be stored in the database or other data structure, logically associated with the identity of the guest. As explained below, this may allow various aspects of the environment of the habitable environment 100 to be customized for the particular occupant.

As illustrated, the habitable environment 100 may be a suite, with a combined sleeping and living area 100a, and a separate bathroom 100b. The habitable environment 100 may include various pieces of furniture or fixtures. For example, the habitable environment 100 may include a bed 116, dresser 118, end tables 120a, 120b (collectively 120). Also for example, the habitable environment 100 include a bathtub or shower 122, sinks 124a, 124b (collectively 124), commode 126 and optionally towel racks 128 in the bathroom portion 100b. The bath or shower 122 may have a faucet 130, showerhead 132 and control handle 134. The control handle 134 is operable to control a flow of water via the faucet 130 and/or showerhead 132, from a supply of water (not shown in FIG. 1). The sink(s) may have a faucet 136 and control handle(s) 138. The control handle(s) 138 is operable to control a flow of water via the faucet 136 from a supply of water (not shown in FIG. 1). The habitable environment 100 may additionally include one or more closets 140.

The habitable environment 100 may include a number of components (e.g., devices, articles, structures) which contribute to a wellness or sense of wellness of the occupant of the habitable environment 100. Some of these components are active components, driven in response to commands or signals, while other components are passive components. These components are brought together as a system, in order to provide synergistic results, thereby enhancing a health, wellness or sense of wellbeing of an inhabitant or occupant of a habitable environment or enclosed space. The various components are discussed below with reference to FIGS. 1 and 2, and exemplary operation of such are discussed below with reference to FIGS. 3-10.

The habitable environment 100 may include a number of active components operable to achieve desired environmental characteristics or scenes, for example related to illumination, heating, ventilation and air conditioning (HVAC), water treatment, and acoustics.

Controlled lighting or illumination is one aspect of achieving the desired environmental characteristics or scenes in or of the habitable environment 100. Thus, the habitable environment 100 may include a number of artificial luminaires 142a-142e (collectively 142), which are controlled to produce desired output, for example by varying intensity and/or composition of wavelengths or color. Luminaires 142 may take a variety of forms, for example lamps (e.g., tabletop, floor standing) 142a, 142b, sconces 142c, 142d, and/or overhead lighting 142e. The luminaires 142 may employ a variety of illumination sources 144, for example incandescent lights, florescent lights, compact florescent lights, and light emitting diode (LED) lighting. The luminaires 142 may optionally include ballasts (e.g., electronic ballasts) and/or other electrical or electronic components required for operation. The luminaires 142 may also include various passive and/or active thermal management components to remove heat, thereby prolonging the operational life of the luminaires 142. Each luminaire 142 may include a plurality of individual illumination or light sources 144, respective ones or sets of the illumination sources 144 operable to emit light in a respective range of wavelengths. Some of the ranges may overlap, while other ranges may or may not overlap. The ones or sets of the illumination sources 144 may be individually operable to achieve any desired distribution of wavelengths at any given time. Each luminaire 142 may include one or more intensity adjustment circuits (e.g., dimmer circuits), which may take a large variety of forms depending on the type of illumination sources 144 employed. For example, an adjustable resistance type dimmer switch may be employed with incandescent sources, while a more sophisticated pulse width modulation technique may be used to control intensity of LED sources.

The habitable environment 100 may additionally or alternatively include a number of components which are controlled to adjust natural light being received in the habitable environment 100 via one or more windows 110 from an exterior thereof for example from a natural source of light (e.g., the Sun). These may include electrochromatic panes 146 in the window 110a and associated actuator, for instance a voltage source 148 coupled to control a transmissivity of the electrochromatic panes 146. Electrochromatic panes 146 may commonly be referred to as electrochromatic glass, but the embodiments herein are not intended to be limited to glass. These may include one or more drapes, shades or curtains or other window coverings (collectively window covering 150) and an actuator such as an electric motor 152 coupled by a transmission 154 to drive the window covering along a track 156 relative to the window(s) 110b.

Various approaches to illumination and components to provide illumination are discussed below, with reference to FIGS. 2 and 4-6.

HVAC is another aspect by which the desired environmental characteristics or scenes of the habitable environment 100 may be achieved. Thus, the habitable environment 100 may include a number of vents 158a-158b (only three shown, collectively 158) that provide air to the habitable environment 100 or portions thereof having desired air temperature, humidity, and/or air quality. At least one of the vents 158 may selectively supply scent(s) to the habitable environment 100 or portion thereof. Various air treatments and components for treating air are discussed below, with reference to FIGS. 2 and 7. In some embodiments the HVAC system includes regional controls such that the air temperature, humidity, and/or air quality may vary in different rooms or regions of the house. In this embodiment, each user in the home inputs their preferences generally and for their specific bedrooms. Based on the individual preferences, their bedroom 24-hour schedule is set and an average calculation is completed to determine how temperature should change Likewise, water is yet another aspect by which the desired environmental characteristics or scenes of the habitable environment 100 may be achieved. Thus, the habitable environment 100 may include a number of faucets 130, 136 and/or showerheads 132 which supply water which has been treated in a variety of ways to enhance wellness. Various water treatments and components for treating water are discussed below, with reference to FIGS. 2 and 9.

The habitable environment 100 may include a number of passive components to achieve desired environmental characteristics or scenes, for example related to flooring system 102, wall system 104, ceiling system 106, acoustics, air quality (e.g., zero or low VOC emitting), and hygiene or sanitation (e.g., anti-pathogen). Many of these are discussed below.

The habitable environment 100 may include flooring system 102, wall system 104 and/or ceiling system 106 designed to achieve a variety of benefits. For example, the flooring system 102, wall system 104 and/or ceiling system 106 designed to reduce exposure to noise.

Loud environments have become a part of modern life. Fans, overhead planes, passing traffic, and loud neighbors all contribute to ambient noise conditions in the home. About half of Americans live in areas where background noise is above 55 decibels (dB)—a level that most consider bothersome. On the logarithmic decibel scale, 0 dB is the point where sounds become discernible to the human ear, and every increase of 10 dB increases the sound pressure level by a factor of 10. Regular exposure to 85 dB for over eight hours at a time can lead to permanent hearing loss. In outdoor urban spaces not immediately adjacent to any sound generators the background noise is often close to 40 db. The World Health Organization recommends an ambient sound level of under 45 dB inside homes and 30 dB for bedrooms.

Thus, the habitable environment 100 may include various passive approaches to achieve the benefit of reduced noise.

Much of the bothersome noise in homes originates from the outside, so acoustic barriers are an important part of overall sound balance. Many of the same technologies that provide effective thermal insulation in walls and windows concurrently block noise. This allows for acoustic protection solutions, while incurring little additional cost. In addition, floor lining reduces sound transmission between apartments and improves perceptions of privacy.

For example, the habitable environment 100 may include a flooring system 102 designed to achieve a variety of benefits. The flooring system 102 may include floor covering 160, subflooring 162, and optionally acoustically damping floor mounts 164 coupling the flooring 160 to the subflooring 162. The flooring system 102 may include one or more additional layers of flooring 166, which provides a resilient member or layer(s) (e.g., cork), as discussed below. The flooring system 102 may include baffle material or insulation (not illustrated), for instance between the additional layer of flooring 166 and the subflooring 162. The flooring system 102 may additionally or alternatively include pads or sheets of material (not shown) that acoustically isolate sources of vibration (e.g., vibrating appliances such as washing machines).

The flooring system 102 uses non-toxic, natural materials that are intended to absorb the sound of footfalls and other vibrations, and provide isolation from exterior or interior sound.

In addition to dampening sound, the flooring can also dampen impact on a user's joints. Whether standing all day or working in the kitchen, the air contained between the millions of cork cells provides a supported feel underfoot. It does not feel spongy since it layers under the floor tiles, but it does act as a shock absorber and provides sufficient comfort to people standing on their feet for long periods of time.

Also for example, the habitable environment 100 may include a wall system 104 designed to achieve acoustic damping. The wall system 104 may include specially constructed walls which incorporate resilient channels 168, double-wallboard or sheetrock 170, double-studs 172, and acoustic insulation designed to decrease sound transmission. The resilient channels 168 resilient couple the double-wallboard or sheetrock 170 to the double-studs 172 to reduce transmission of vibration.

As another example, the habitable environment 100 may employ acoustically damping doors 108. For instance, solid oak doors that tightly seal to a door frame, may achieve sound reduction on par with well-constructed walls.

As a further example, the habitable environment 100 may employ acoustic damping windows 110. For instance, triple glazed windows 110 with vacuum or rare earth gases trapped therebetween may minimize sound transmission from the exterior.

As yet a further example, the habitable environment 100 may employ acoustically damping plumbing insulation 174. For instance, non-toxic blankets of acoustically damping material 174 may be wrapped around water pipes (not shown) and air ducts 176 to reduce the sound transmitted by metal conduits.

The health effects of flooring have become the focus of a growing number of studies. Research shows that standing on surfaces without any give or cushioning for extended periods of time forces muscles into a constant state of flexion. This decreases circulation, promotes bad posture, causes lower back pain and can lead to orthopedic ailments. Cushioned mats decrease the impact on joints and promote muscle relaxation.

The habitable environment 100 may employ a cushion-lined flooring system 102 in order to realize a number of benefits, including increased circulation and promotion of healthy posture. The result may be fewer reports of joint pain, discomfort, and low energy. In addition, standing on softer surfaces decreases the risk of developing plantar fasciitis, and can alleviate symptoms for those already suffering from the condition. The flooring system 102 should be soft or resilient enough to allow for underfoot comfort, yet strong enough to improve lumbar support. The flooring system 102 consists of floating construction, for example with cork under layer(s) 166 to reduce forces generated from impacts by increased deflection.

Reflexology is a traditional practice of massage, which aims to reduce the symptoms of various ailments. Practitioners use stimulation of specific areas of the hands and feet to reduce tension and stress. Evidence has shown that the practice of reflexology has powerful anxiety reduction with reduced blood pressure and pulse rates. The habitable environment 100 may employ a custom-designed pathway (e.g., bathroom pathway), with textured floor covering 178, designed to improve blood circulation and general wellbeing by encouraging reflexology therapy.

Due to large surface area, floor finishing can often be a major source of VOCs. The habitable environment 100 uses natural flooring materials chosen to reduce the emissions of harmful indoor air pollutants and volatile organic compounds.

Electromagnetic fields (EMF) are created when charged particles are in motion. The movement of electrical charge through wires and appliances creates electromagnetic fields. The strength of the electric field depends on the voltage (e.g. typically 120 V for households) and is present near live wires, whether or not an electrical appliance is in use. Research suggests that long-term and significant occupational exposure to EMF may increase the risk of both Alzheimer's disease and breast cancer.

Thus, EMF shielding is incorporated into the habitable environment 100. The EMF shields are designed to block the spread of the field by creating a barrier composed of conductive or magnetic materials. EMF shields have traditionally been made out of solid metal, though this poses challenges regarding weight, corrosion, and malleability. Treated metal mesh or screens with openings smaller than the electromagnetic wavelength may provide a more practical solution.

Thus, for example the habitable environment 100 may include EMF shielding for wiring. In particular, wiring may be insulated with foil wraps designed to shield EMF from occupied parts of the habitable environment 100. Also for example, low EMF electrical wiring may be employed.

Another passive approach takes advantage of anti-bacterial or anti-pathogen (i.e., "treated") materials to reduce or eliminate the presence of bacteria or pathogens. The anti-bacterial or anti-pathogen materials may be incorporated into or deposited on bedding (e.g., sheets, bedspreads, throws, pillows, pillow covers) 180, window coverings (e.g., drapes, shades, curtains) 150 and/or surfaces (e.g., counters 181, tubs or shower stalls 122, table tops 120, walls 104). For example, various materials may be impregnated or coated with anti-bacterial or anti-pathogen materials. These materials may have opening or pore sizes on the order of 1 micron, providing an effective barrier against penetration by various undesirable particles. Any seams in the bedding should be sealed. At least in the case of bedding, these materials preferably completely encase or envelope mattress, box springs, pillows, and/or comforters. Such may provide protection against bedbugs, allergens, and/or dust mites.

Examples of suitable materials may contain or include, silver (Ag) in ionic form, which has proven effective against a variety of pathogens.

In order to reduce exposure to pathogens and toxins without excessive use of chemicals or cleaning, the amenities below lower the effort required in maintaining a healthy environment.

As a further example, titanium dioxide nanoparticles have emerged as an effective means of reducing air pollutants through photocatalyst which creates a self-cleaning surface powered by ambient light exposure. For example, the nanoparticles may catalyze a reaction converting VOCs to harmless carbon dioxide. Such may be incorporated into a photo-catalytic coating which may be used on walls to break down bacteria, virus, and VOCs when exposed to light.

The habitable environment 100 may include anti-bacterial or anti-pathogen materials as structural materials. For example, cedar may be employed in closets and/or used as baseboards. Certain species of cedar act as a natural pest control, repelling many insects. Oils present in cedar wood have been shown to repel fungi (such as mold), bacteria, insects, termites, and ticks.

An ability to control a function or operation of at least the active components may be useful in realizing the amenities and benefits offered in the habitable environment 100. Thus, a number of user operable input/output (I/O) devices, controls, panels or kiosks 182 may be supplied.

For example, an in-room user operable I/O panel 182a may include a display (e.g., LCD) to display information. The in-room user operable I/O panel 182a may include user actuatable controls (e.g., user selectable icons displayed on touch screen, keys, buttons) manipulation of which allows a user, for instance an occupant of the habitable environment 100, to select parameters or programs (also referred to as scenes) to execute to control one or more of the environmental characteristics or scenes in or of the habitable environment 100.

Also for example, a mobile or handheld device 182b may serve as an I/O device. The mobile or handheld device 182b may include a display (e.g., LCD) to display information and user actuatable controls (e.g., user selectable icons, keys, buttons) manipulation of which allows a user, for instance an occupant of the habitable environment 100 or facility personnel, to select parameters or programs or scenes to execute to control one or more of the environmental characteristics or scenes in or of the habitable environment 100. The mobile or handheld device 182*b* may be owned by the end user, for example the occupant. The mobile or handheld device 182*b* may execute a downloaded customized application or "APP" that communicatively interfaces via a wireless protocol (e.g., IEEE 802.11, BLUETOOTH®, WI-FI®).

Alternatively or additionally, a remote user operable I/O controls, panel or kiosk 182*c* (FIG. 2) may include a display (e.g., LCD) to display information. The remote user operable I/O controls, panel or kiosk 182*c* may include user actuatable controls (e.g., user selectable icons displayed on touch screen, keys, buttons) manipulation of which allows a user, for instance personnel of the facility in which the habitable environment 100 is located, to select parameters, scenes or programs to execute to control one or more of the environmental characteristics or scenes in or of the habitable environment 100.

Information about the amenities and benefits afforded by the wellness system in the habitable environment 100 may be useful in realizing the benefits of such. Information may be provided via a server and presented via a variety of devices. For instance, information may be presented via a television 184 for instance on a dedicated channel, via in-room or other display, panel or kiosk 182*a*, via handheld device 182*b*, etc.

System and Subsystems

Figure 2:
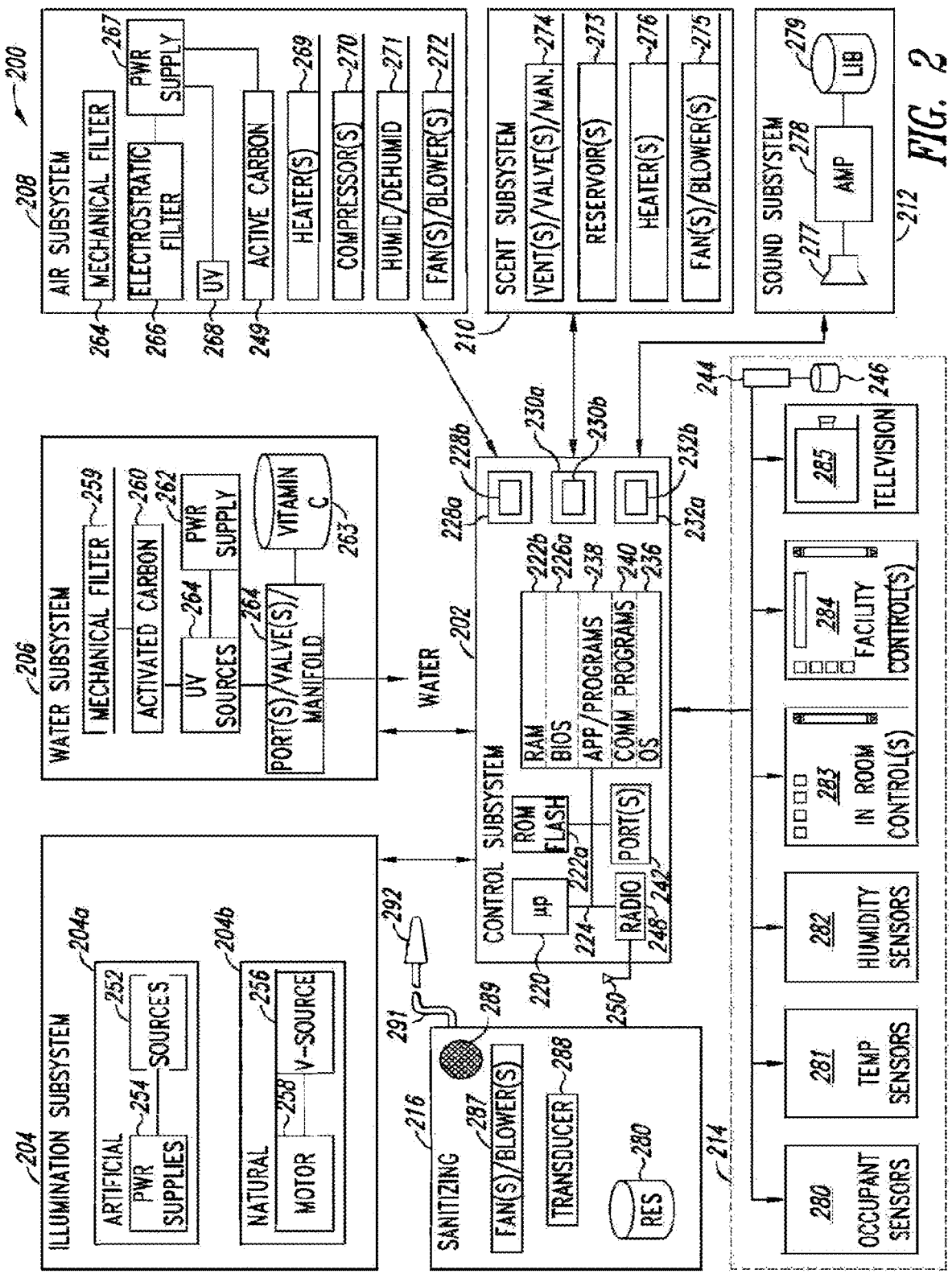
FIG. 2 is a block diagram that shows a portion of a habitable environment enhancement system to enhance a habitable environment, according to one illustrated embodiment.

FIG. 2 shows an active portion of an environmental control system 200 for controlling environmental characteristics scenes in or of a habitable environment 100 (FIG. 1), according to one illustrated embodiment. FIG. 2 provides a more detailed representation of some of the components of FIG. 1.

The active portion of an environmental control system 200 includes a number of subsystems. For example, the active portion may include a control subsystem 202, illumination subsystem 204, water treatment subsystem 206, air treatment subsystem 208, scent subsystem 210, sound subsystem 212 input/output (I/O) subsystem 214. The active portion may optionally include a sanitizing subsystem 216, which as described below may be either build in or a fixture of the habitable environment 100, or may be portable, being located in the habitable environment 100 only during use. Each of the subsystem 202-216 and/or components are discussed in turn below with reference to FIG. 2. Operation of many of these subsystems 202-216 and/or components are discussed with reference to FIGS. 3-10 below.

The control subsystem 202 may take the form of a programmed computer or other processor-based system or device. For example, the control subsystem 202 may take the form of a conventional mainframe computer, minicomputer, workstation computer, personal computer (desktop or laptop), or handheld computer.

The control subsystem 202 may include one or more processing units 220 (one illustrated), nontransitory system memories 22*a*-222*b* (collectively 222) and a system bus 224 that couples various system components including the system memory 222 to the processing unit(s) 220. The processing unit(s) 220 may be any logic processing unit, such as one or more central processing units (CPUs), digital signal processors (DSPs), application-specific integrated circuits (ASICs), field programmable gate arrays (FPGAs), programmable logic controllers (PLCs), etc. Non-limiting examples of commercially available computer systems include, but are not limited to, an 80×86, Pentium, or i7 series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation. The system bus 224 can employ any known bus structures or architectures, including a memory bus with memory controller, a peripheral bus, and a local bus. The system memory 222 includes nontransitory Flash or read-only memory ("ROM") 222*a* and nontransitory random access memory ("RAM") 222*b*. A basic input/output system ("BIOS") 226*a*, which can form part of the ROM 222*a* or RAM 222*b*, contains basic routines that help transfer information between elements within the control subsystem 202, such as during start-up.

The control subsystem 202 may include a hard disk drive 228*a* for reading from and writing to a hard disk 228*b*, an optical disk drive 230*a* for reading from and writing to removable optical disks 230*b*, and/or a magnetic disk drive 232*a* for reading from and writing to magnetic disks 232*b*. The optical disk 230*b* can be a CD/DVD-ROM, while the magnetic disk 232*b* can be a magnetic floppy disk or diskette. The hard disk drive 228*a*, optical disk drive 230*a* and magnetic disk drive 232*a* may communicate with the processing unit 220 via the system bus 224. The hard disk drive 230*a*, optical disk drive 230*a* and magnetic disk drive 232 a may include interfaces or controllers (not shown) coupled between such drives and the system bus 224, as is known by those skilled in the relevant art. The drives 228*a*, 230*a* and 232*a*, and their associated computer-readable storage media 228*b*, 230*b*, 232*b*, may provide nonvolatile and non-transitory storage of computer readable instructions, data structures, program engines and other data for the environmental control system 200. Although control subsystem 202 is illustrated employing a hard disk 228*a*, optical disk 230*a* and magnetic disk 232*a*, those skilled in the relevant art will appreciate that other types of computer- or processor-readable storage media that can store data accessible by a computer may be employed, such as magnetic cassettes, flash memory, digital video disks ("DVD"), Bernoulli cartridges, RAMs, ROMs, smart cards, etc. The hard disk 228*a* may, for example, store instructions and data for controlling the other subsystems, for example based on specific aspects or characteristics of an occupant of the habitable environment 100 (FIG. 1), to provide environmental characteristics or scenes that promote the wellness or wellbeing of the occupant(s). The hard disk 228*a* may, for example, store instructions and data for presenting information about the various attributes and benefits provided by the active and passive components or measures, and instructions on how to use the environmental control system 200 and the passive components to maximize enjoyment, comfort, and well-being.

Program engines can be stored in the system memory 222*b*, such as an operating system 236, one or more application programs 238, other programs or engines and program data. Application programs 238 may include instructions that cause the processor(s) 220 to automatically generate signals to control various of the other subsystems to achieve various environmental characteristics or scenes in the habitable environment 100 (FIG. 1), for example based on one or more aspects, characteristics or attributes of an occupant thereof. Application programs 238 may include instructions that cause the processor(s) 220 to automatically receive input and/or display output via various user operable input/output (I/O) devices, controls, panels or kiosks 182 or television 184.

Other program engines (not specifically shown) may include instructions for handling security such as password or other access protection and communications encryption. The system memory 220 may also include communications programs 240, for example, a server for permitting the control subsystem 202 to provide services and exchange data with other subsystems or computer systems or devices via the Internet, corporate intranets, extranets, or other networks (e.g., LANs, WANs), as well as other server applications on server computing systems such as those discussed further herein. The server in the depicted embodiment may be markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers are commercially available such as those from Microsoft, Oracle, IBM and Apple.

While shown in FIG. 2 as being stored in the system memory 222*b*, the operating system 236, application programs 238, other programs/engines, program data and communications applications (e.g., server, browser) 240 can be stored on the hard disk 228*b* of the hard disk drive 228*a*, the optical disk 230*b* of the optical disk drive 230*a* and/or the magnetic disk 232*b* of the magnetic disk drive 232*a*.

An operator can enter commands and information (e.g., configuration information, data or specifications) into the control subsystem 202 via various user operable input/output (I/O) devices, controls, panels or kiosks 182 or television 184, or through other input devices such as a dedicated touch screen or keyboard (not shown) and/or a pointing device such as a mouse (not shown), and/or via a graphical user interface. Other input devices can include a microphone, joystick, game pad, tablet, scanner, etc. These and other input devices are connected to one or more of the processing units 220 through an interface such as a serial port interface 242 that couples to the system bus 224, although other interfaces such as a parallel port, a game port or a wireless interface or a universal serial bus ("USB") can be used. A monitor or other display device is coupled to the system bus 224 via a video interface, such as a video adapter (not shown). The control subsystem 202 can include other output devices, such as speakers, printers, etc.

The control subsystem 202 can operate in a networked environment using logical connections to one or more remote computers and/or devices as described above with reference to FIG. 1. For example, the control subsystem 202 can operate in a networked environment using logical connections to one or more other subsystems 204-214, one or more server computer systems 244 and associated nontransitory data storage device 246. The server computer systems 244 and associated nontransitory data storage device 246 may, for example, be controlled and operated by a facility (e.g., hotel, spa, apartment building, condominium building, hospital) in which the habitable environment 100 (FIG. 1) is located. Communications may be via wired and/or wireless network architectures, for instance, wired and wireless enterprise-wide computer networks, intranets, extranets, and the Internet. Thus, the control subsystem 202 may include wireless communications components, for example one or more transceivers or radios 248 and associated antenna(s) 250 for wireless (e.g., radio or microwave frequency communications, collected referred to herein as RF communications). Other embodiments may include other types of communication networks including telecommunications networks, cellular networks, paging networks, and other mobile networks.

Illumination (e.g., electromagnetic radiation or energy with wavelengths in the visible, near infrared (NIR) and/or near ultraviolet (NUV or UVA) portions of the electromagnetic spectrum) can have a significant effect on human health. As used herein and in the claims, the terms illumination or light include energy in the portions of the electromagnetic spectrum which are visible to humans (e.g., approximately 400 nm-approximately 700 nm) and not visible to humans (e.g., NIR or UVA). Light influences the human body in a number of unconscious ways. Metabolism has been deeply linked to the daily solar cycle through melatonin and the endocrine system. This cycle in the human body is called the circadian rhythm. Humans and animals have an internal clock that keeps the body on an approximately 24-hour cycle which matches the Earth's daily solar cycle, even in continuous darkness. Multiple bodily processes, from periods of alertness and sleep to digestion efficiency, are partially regulated by the intensity and color of light received by the eyes. However, light adjusts this internal timing to align the person to the Earth's daily solar cycle. Exposure to light comparable to the intensity of direct sunlight light will aid in resetting the circadian rhythm if it has been upset by shift work or long distance travel.

The intensity and color of light impacts different systems of the body. For example, blue light impedes the body's production of melatonin, a chemical messenger used to induce sleep. High intensities in the evening delay sleep, while light in the morning aids in waking. The appropriate brightness and color also contribute to alertness and concentration throughout the day. Melatonin is a natural antioxidant and counteracts the cancer-causing tendencies of free radicals. As a result, melatonin depletion from inappropriate exposure to bright lights leads to an increased risk of cancer. Bright light during midday and dimmer light at dinnertime aid in the digestion of carbohydrates.

Additionally, many individuals suffer from light-related mood irregularities, such as Seasonal Affective Disorder (SAD). Proper exposure to specific types of light at specific times addresses these irregularities. Exposure in the morning to gradual light brightening through dawn simulation has been shown to reduce depression. Daylight aids in the healthy development of eyesight. Myopia in children has been linked with low exposure to daylight and conversely, high reliance on dim artificial light. Age related macular degeneration, or the deterioration of eyesight with age, particularly in seniors with blue eyes can be minimized by reducing the exposure to high color temperature.

The illumination subsystem 204 may also be controlled to deliver light therapy, with or without topical photoactive substances. Such may, for example be used to treat a variety of conditions, for instance Seasonal Affective Disorder (SAD). People who live in high latitudes often experience depression during the winter as a result of long periods of reduced sunlight, a condition identified as SAD. For those affected by SAD, measures of sleep efficiency in the winter are noticeably different than those in the summer. Light therapy may be especially effective at treating SAD, producing results comparable to treatment with medication.

Another condition or syndrome commonly referred to as "jet lag" results from the relative shift between the circadian rhythm and the daily solar cycle. The effects are a disruption of sleep and a significant deterioration in mood, concentration, and cognitive performance. Controlled light exposure to help match the solar and circadian light cycles can help alleviate these symptoms.

In some individuals, the body's production or interpretation of melatonin slightly varies relative to the solar cycle, resulting in a set of symptoms identified as Delayed Sleep-Phase Syndrome (DSPS). Approximately one tenth of all adolescents and some adults find themselves falling asleep two to six hours after conventional bedtime. If left undisturbed, these individuals will often sleep soundly for approximately eight hours before waking in the middle of the day. Controlled lighting may help treat DSPS.

Emerging research indicates that different brain activity occurs when the human body is exposed to different parts of the light spectrum. Color can subconsciously affect people's abilities to do different types of tasks. For example, in one study, participants performed analytical tasks better in red light, and were more creative in blue-colored environments.

Research into workplace environments has found that people in brightly colored offices had higher measured emotional status than those in subdued or neutral surroundings. On the other hand, studies have shown that intense colors may be irritating to certain individuals. Chromotherapy employs illumination of certain wavelengths or combinations of wavelengths as an effective manipulator of mood given individual preferences. Practitioners use this therapy to address issues such as meditation, intuition, speech, nervousness and anxiety.

The illumination subsystem 204 may be operated to provide dynamic custom coloring throughout the habitable environment 100 (FIG. 1) or portion thereof in order to provide chromotherapy. Additionally, the habitable environment 100 (FIG. 1) may optionally employ a chromotherapy wall wash in the form of a wall colored by light (e.g., via cover lights or sconces) that dynamically changes color to create a desired light spectrum for different settings and times of day. Additionally or alternatively, chromotherapy lighting can be added to specific areas where colored lights may be more desirable, such as meditation spaces and steam showers.

The illumination subsystem 204 discussed below is used to preserve and remediate the disruption of circadian rhythm, enhancing health, including the natural sleep cycle, the healthy development of the eyes among some attributes, and treating or alleviating the symptoms of various disorders, syndromes and/or afflictions. The illumination subsystem 204 may, for example, expose occupants or residents of a habitable environment 100 (FIG. 1) or portion thereof to short periods of intense artificial light for therapeutic effects while subjects are awake as part of delivering light therapy.

The illumination subsystem 204 includes an artificial illumination subsystem 204a and a natural illumination subsystem 204b, which are operated in tandem to provide desired illumination in the habitable environment 100 (FIG. 1). In particular, the illumination subsystem 204 provides lighting in the habitable environment 100 (FIG. 1) with gradually adjusted color temperature and intensity to, for example improve circadian rhythm. As discussed below, the illumination subsystem 204 may implement a dawn simulator to gradually increase light and sound levels, which are designed to awaken the body when it enters a light stage of sleep. Such may replace standard alarm clocks producing a more natural environment to slowly wake from. Such may be realized by slow opening blackout shades or slowly allowing more light to pass through an electrochromatic pane over a wakeup period. Active sound may also be slowly increased in volume. Sounds may be those found in the natural environment or may be other sounds, such as music. Such may be realized in an integral unit, or via a dedicated bedside unit, which may provide for sounds as well as artificial lighting.

Also as discussed below, the illumination subsystem 204 may implement nightlights, employing dim (e.g., low-wattage) long wavelength LED or incandescent luminaires that engage in response to motion or ambient light levels, and are designed to sufficiently illuminate rooms for safe navigation without disturbing melatonin levels.

The artificial illumination subsystem 204a includes a plurality of illumination sources 252, and optionally one or more power supplies 254. As previously noted, the illumination sources 252 may take a wide variety of forms, for instance incandescent, florescent, compact florescent, or LED lights. LED lighting may be preferable since such is extremely energy efficient and may have a long operating life. The illumination sources 252, either alone or in combination, should be capable of selectively providing a broad range of intensities and a broad range of wavelengths. Such allows the illumination sources 252 to be selectively controlled to produce a wide variety of artificial illumination conditions, for instance conditions or scenes that mimic natural light, diurnal light patterns, circadian light patterns, light therapy patterns, and/or light patterns to accommodate for changes in location (e.g., latitude and/or longitude) or changes in season (e.g., spring, summer, autumn, winter). A circadian light pattern may be a pattern of light during a defined period of time (e.g., solar day, approximately 24 hours) which mimics the intensity and/or color of naturally occurring light (e.g., sunlight and darkness) for a given location (e.g., latitude and/or longitude) and/or at a given time of year (e.g., season, month). A produced or generated or provided circadian light pattern may be produced by a combination of artificial and naturally occurring light, which may be controlled to produce a defined or desired circadian light pattern. The defined or desired circadian light pattern may itself be different from a naturally occurring circadian light pattern at a particular location and/or time of year, or may simply be shifted relative to the naturally occurring circadian light pattern at a particular location and/or time of year. The illumination sources 252 may take the form of arrays of LEDs, each LED capable of producing one or more ranges of wavelengths. Wavelength of emitted light may be adjusted by varying a drive current supplied to LEDs. Thus, desired wavelengths may be achieved by selectively operating certain sets of LEDs (e.g., LEDS that emit in a given range of wavelengths), and/or by varying a current level supplied to any given LEDs. Intensity may be adjusted by selectively operating more or less LEDS, or by controlling power supplied to one or more LEDs via the power supply or supplies 254. For example, a duty cycle of a pulse width modulated (PWM) drive signal may be varied to adjust intensity out the output.

The power supply or supplies 254 may take a wide variety of forms, mostly dependent on the source of power (e.g., AC line current, DC), and the illumination sources (e.g., LEDs). The power supply or supplies 254 may include a transformer to electrically isolate the rest of the circuit from the source of power, and/or step down or step up a voltage. The power supply or supplies 254 may include a switch mode converter, operable to step down and/or step up a voltage. The power supply or supplies 254 may include one or more rectifiers (e.g., passive diode bridge, active transistor bridge of MOSFETs or IGBTs) to rectify AC power to DC power. Less likely, the power supply or supplies 254 may include one or more inverters, to invert DC power to AC power. The power supply or supplies 254 may include one or more dedicated power supply controllers, for instance a microcontroller such as a microprocessor, DSP, ASIC, PGA, or PLC and/or associated nontransitory computer- or processor-readable media. The power supply or supplies 254 is or are communicatively coupled to control a supply of electrical power to the illumination sources.

The natural light subsystem 204b may include one or more actuators, which a drivingly coupled to control an amount of natural light received in the habitable environment 100 (FIG. 1) via one or more windows 110. As previously discussed, the actuators may, for example take the form of an electrical power source 256 coupled to control a transmissivity of one or more electrochromatic panes or panels 146 (FIG. 1). As also previously discussed, the actuators may, for example take the form of an electric motor 258, solenoid or other element drivingly coupled that control a position of one or more window coverings 150 (FIG. 1) relative to the window, and thereby adjusting an amount of illumination that passes. The window coverings 150 may take the form of "blackout shades", that are automatically operated to shield an occupant or resident of the habitable environment 100 (FIG. 1) from outdoor light. The actuator 256, 258 may receive electrical power from a voltage source, or may receive control signals form a microcontroller.

Electrochromatic panes or panels 146 (FIG. 1) may be capable of adjust (i.e., selectively substantially passing, selectively substantially blocking) ranges of wavelengths passed or block, as well as intensity of natural illumination passed or blocked. Thus, electrochromatic panes or panels 146 (FIG. 1) may be preferred over the window covering approach.

Controlling ingress of ambient light (e.g., sunlight, light from street lamps, buildings or signage, security lighting) from an exterior environment aids in management of exposure to levels of light in order to help maintain healthy circadian rhythms. This is particularly important during early summer mornings and long summer evenings, particular at high latitudes (e.g., above or greater than approximately 40 degrees North or South) and/or urban environments.

Municipal water systems use many methods to control the purity of water. Although these methods generally succeed in bringing contaminant levels within national and state limits, water quality occasionally becomes an issue. For example, the Las Vegas sodium and sulfate levels in water would fail NYC city standards. In New York, byproducts formed by chlorination are near the federal limit. In response to these concerns, habitable environments 100 may use supplemental treatment technologies to bring contaminant concentrations well within the safety limits set by American regulatory agencies, as well as international safety standards.

New York City water is currently unfiltered, but a filtration plant is under construction for water drawn from the Croton Reservoir. Additionally, a UV sanitization facility is under construction for germicidal irradiation for the remaining water sources (Catskill/Delaware system).

Sediments-Solids of sulfates and chlorides can be suspended in water and produce a cloudy opacity, or turbidity. Water with high turbidity is not inherently unhealthy but elevated levels may be indicative of problems in the filtration process, which may imply that other contaminants have not been adequately removed. The coarse filters 259 reduce suspended solids in water. This is often the first stage of treatment, which optimizes performance of subsequent filters in the system.

Municipal water systems often add chlorine-based disinfectants are added to the water supply to remove bacteria. This affects water odor and taste, and causes potential irritation of the eyes. The human body contains beneficial symbiotic bacteria, which are necessary for the proper function of the skin and digestive tract. These microbes on the skin are harmed by chlorine. When chlorinated water comes into extended contact with organic matter, byproducts such as tri-halomethanes and halo-acetic acids can form, which are carcinogenic.

Pharmaceuticals and Personal Care Products (PPCP) comprise a myriad of different chemicals used as active ingredients in medications, cleaning products, and health supplies. PPCP enter the water system through multiple pathways, such as incomplete metabolism of drugs in the body, improper disposal of pills or personal care and cleaning products. Potentially unsafe levels of PPCP have accumulated in lakes and rivers, where they can enter municipal water systems. PPCPs are the likely cause of hermaphroditism in fish and lake amphibians, as well as other reproductive harm. Further contamination of water supplies is expected and increases in the quantity of PPCPs in the water are the subject of numerous research programs. The activated carbon water filters 260 that reduce disinfectant byproducts, pesticides, dissolved gases, chlorine, chloramine, and some pharmaceutical and personal care products, resulting in cleaner and better-tasting water. "Activated" charcoal filters contain a maze of passageways and openings, giving activated carbon some 1000 square meters of surface per gram.

Numerous forms of micro-organisms may be damaging to health or an indicator of poor water quality.

For example, coliforms are common, rod-shaped bacteria that are harmless in and of themselves. Like turbidity and suspended solids, coliforms act as indicators: their presence suggests that other, more dangerous microorganisms could survive water treatment and may be present in the supply. The EPA goal for coliforms is zero trace, but the enforceable limit allows 5% of all samples within a single month to test positive. New York City tested positive for 46 of 9958 samples taken in 2010 (or 1.3% of samples in the highest month).

Also for example, *Escherichia coli* (*E. coli*) bacteria are also rod-shaped bacteria, and the majority of strains are harmless. Some strains, such as O157:H7, cause food poisoning by excreting toxic chemicals that can be life threatening for vulnerable individuals. *E. coli* is transmitted as a result of eating unwashed or undercooked food. Infectious *E. coli* can also be found in water contaminated with fecal matter, such as agricultural runoff.

As further examples, *Cryptosporidium* and *Giardia* are single-celled microbes often found in water systems contaminated by sewage. Much larger than bacteria, these protozoa cause digestive problems, especially in vulnerable populations.

The water treatment subsystem 206 ensures that a supply of clean, healthy water is supplied to the habitable environment 100 (Figure) for example via taps such as the faucets 130, 136 (FIG. 1) or showerhead 132 (FIG. 1). The water treatment subsystem 206 may use a multi-step approach.

The water treatment subsystem 206 may include one or more mechanical filters 259. The mechanical filters 259 may include one or more sediment or coarse filters to filter sediment or larger particulate matter from the water. The mechanical filters 259 may include one or more fine filters to filter fine particulate from the water. Various types of coarse filter and/or fine filter media may be employed, including wire mesh screens, diatomaceous earth, and/or ceramic water filter elements. Access to water that is without inorganic, organic and biological contaminants is essential for maintaining optimal human health. These contaminants, especially in high doses, can be toxic and impair health and overall quality of life. Removal of contaminants can be achieved by installing filters at the point-of-use (assuming the water is mostly potable), most commonly at sink and shower faucets. When selecting a water filter, strict performance criteria must be met to minimize the risks posed by contaminants.

The water treatment subsystem 206 may include one or more activated charcoal filters 260. The activated charcoal filters may remove particulate in the size range of approximately 0.5 micrometers to 50.0 micrometers.

As an alternative to adding chemical disinfectants, water can be disinfected by irradiation with UV light. The high-energy light damages the DNA of microorganisms, making it less possible for them to reproduce. UV treatment is highly effective in clear, sediment-free water. Thus, the water treatment subsystem 206 may employ Ultra-Violet Germicidal Irradiation (UVGI), in an attempt to eliminate microorganisms without using chemical-based filtering. In particular, the water treatment subsystem 206 may include one or more ultraviolet (UV) illumination sources 261 operable to expose the water to UV illumination of sufficient intensity and for sufficient time as to render pathogens in the water non-harmful. The UV illumination sources 261 may be supplied electrical power from one or more dedicated electrical power supplies 262.

As an alternative, a reverse osmosis system (not shown) preceded by a carbon filter may replace the sediment filter and ultraviolet irradiation for the removal of chlorine, PPCPS, disinfectant byproducts, heavy metals, microbes, and water hardeners.

The water treatment subsystem 206 may include one or more reservoirs of vitamin C 263 and one or more ports, valves, or manifolds 264 operable to release vitamin C into the water. The ports, valves, or manifolds 264 may be fluidly coupled to release vitamin C only in certain plumbing runs, for example supplying vitamin C only to water going to the showerhead 132 (FIG. 1) or optionally the faucet 130 associated with the tub or shower stall 122 (FIG. 1). An infusion of vitamin C into shower water may remove residual chlorine. In high concentrations, the skin can absorb vitamin C for example when applied as a topical cream. While these levels are significantly higher than those present in the showers, the shower water still provides the skin with small amounts of nutrients.

The air treatment subsystem 208 may include a variety of components to ensure that air supplied to the habitable environment 100 (FIG. 1) is healthy and comfortable for the occupant(s).

Good air quality is one of the most important features of a healthy environment. Stationary adults typically inhale 6 to 10 liters of air each minute. This amount doubles with moderate activity and doubles again with rigorous exercise. Approximately 15 cubic meters of air pass through the lungs of a moderately active adult each day.

Minute quantities of gaseous pollutants and particulates are present in the air from both natural and anthropogenic sources, which can cause serious health problems. Reducing the sources of gases and particulates in the home will decrease their negative effects. Airborne contaminants generated by materials, and the presence of individuals in the home, require expulsion through ventilation to the outdoors, and filtration to ensure that they do not return to the indoor air supply.

The major health effects of poor air quality are lung cancer and cardio-pulmonary disease. A significantly greater number of deaths from these ailments are attributable to periods of higher levels of particulate matter. Other effects of air quality are asthma attacks, emphysema, and interference with the immune system.

At the microscopic scale, natural laws concerning fluid dynamics and gravity work differently, allowing solids and liquids to float in the air almost indefinitely. Put broadly, this microscopic particulate matter is divided into two categories: fine particles, smaller than 2.5 μm (PM2.5); and coarse particles larger than 2.5 μm and smaller than 10 μm (PM10-2.5). Fine particles are inhalable particles that can lead to a number of health issues. Due to physical processes that govern their formation, fine particles are inherently more acidic and mutagenic than their larger counterparts. Fine particles are drawn deep into the lungs, maximizing damage. Most cases of mortality from inhalation of coarse particulate matter and larger contaminants arise from toxic chemicals they contain rather than the particles themselves.

Coarse particles do not penetrate as deeply into the lungs as fine particles, and therefore are the less dangerous of the two. However, many coarse particles are allergens. For example, dust mites are microscopic arachnids that feed on pet dander, dead human skin cells, and other biological matter. They thrive in carpets, mattresses, and curtains, and tend to dwell in synthetic fibers rather than natural materials. Mites are not inherently dangerous, but their droppings contain chemicals that trigger an immune response in some individuals. The resulting symptoms often include itchy eyes, runny nose, and wheezing, a reaction that can be particularly debilitating for asthmatics. Nearly one quarter of American homes have dust mite levels associated with symptomatic asthma, and almost half contain enough dust mites to cause allergic reactions in susceptible individuals.

Air constantly flows into homes and is subject to a wide range of pollutants both from outdoor air pollution and source contaminants within the home. Indoor air pollution is among the top five environmental health risks and has been shown to be 2-5 times higher than the pollution of outdoor spaces—up to 100 times higher in extreme cases. Therefore, effectively managing indoor air quality through the filtration of air drawn from outdoors and the circulation of indoor air can help reduce the concentration of contaminants in the home. The air treatment subsystem 208 may include one or more mechanical air filters (e.g., mesh, screen, woven, or piled material) 265, through which air passes to remove larger particulate. Suitable mechanical air filters may include an activated carbon air filter, high efficiency particulate (HEPA) air filter (i.e., MERV equivalent 17+), MERV 13-16 air filter, a quantity of Zeolite, or a porous material.

The air treatment subsystem 208 may include one or more electrostatic filters or precipitators 266 to remove fine particulate. In particular, electrostatic filter(s) 266 trap particles that could contain allergens, toxins, and pathogens. In addition, the electrostatic filter(s) 266 are installed to reduce dust mites, pollen, carpet fibers, mold spores, bacteria, smoke, and diesel particulate matter from the air. The electrostatic filter(s) 266 attracts particles using an electrostatic charge and extracts them from the air into a wire mesh.

The electrostatic filters 266 may take a variety of forms, for instance ones which place a charge on particles and an opposite charge on a screen or other electrode element to attract the charged particles. An example of such is a corona discharge type of electrostatic filter. The electrostatic filter 266 may be supplied charge via an electrical power supply 267.

Various airborne pathogens may present problems, particular in enclosed spaces or habitable environments. This may be of particular concern with newer construction techniques which are employed to reduce the exchange of air with the exterior environment, for instance to reduce heat loss and thereby increase thermal efficiency. Although most airborne microbes are pervasive and generally harmless, some can be dangerous pathogens easily spread throughout a home's ventilation system.

Mold spores can induce skin, nose, throat, and eye irritation, and trigger asthma attacks. These fungi release volatile organic compounds that produce the characteristic "moldy" odor and have been linked to dizziness and nausea. Humidity control has been proven effective in reducing mold, and insulated windows reduce condensation so as to prevent mold from growing in nearby joints.

Individual microbes are very small and can evade some filters if not attached to other particles. In order to reduce the probability of airborne pathogens from traveling through the enclosed space or habitable environment 100 (FIG. 1), UVGI can be used to provide additional protection. UVGI is based on a specific frequency of UV light that specifically targets the DNA of microbes and viruses passing through the ventilation system. The growth and spread of health-threatening biotic agents is a primary concern for moisture buildup in HVAC systems. The use of ultraviolet germicidal irradiation (UVGI) lights installed on the upstream side of the coil in HVAC systems has been associated with a significant reduction in microorganism concentrations on irradiated cooling coils and drip pans. According to a study conducted on office workers, significantly fewer work-related respiratory, mucosal, and overall health symptoms were reported when a UVGI system was used; the use of UVGI also resulted in a 99% reduction in the concentrations of bacteria, fungi, and endotoxins on irradiated surfaces in the HVAC system.

The air treatment subsystem 208 may include a UV air sanitizer designed to disinfect air via UV light within one or more components (e.g., ducts) of a ventilation system. The aim is to sterilize airborne bacteria, viruses, dust mites, and mold spores that may have escaped filtration.

Thus, the air treatment subsystem 208 may include one or more UV illumination sources 268. The UV illumination source(s) 268 is positioned to illuminate air with UV illumination of a sufficient intensity for a sufficient time as to render pathogens non-harmful.

Various gaseous pollutants may produce harmful effects in humans, particularly where allowed to accumulate in habitable enclosed spaces. Volatile Organic Compounds (VOCs) are carbon-based chemicals that evaporate into gases at room temperature. Many paints, cleaning products, and pest control chemicals emit VOCs, whose presence in buildings is 2 to 5 times as high as outside levels. Some furniture and building materials also slowly release some kinds of VOC, such as formaldehyde. In the short term, exposure can cause dizziness, nausea, headaches, throat irritation, and fatigue, while chronic effects include damage to the liver, kidneys, and central nervous system.

Nitrogen dioxide is a product of combustion and mainly found near burning sources. Indoor areas that contain gas stoves, fireplaces, and cigarette smoke often have a much higher concentration of nitrogen dioxide. Epidemiological studies suggest that excessive nitrogen dioxide inhalation may decrease lung function, particularly in children. In the short term, it can also trigger allergic responses from the immune system, resulting in irritation of the eyes, nose, and throat.

Ozone is created by reactions between molecular oxygen, nitrogen oxides, and sunlight. It is the major catalyst in the formation of smog. Ozone impedes cellular respiration, resulting in reduced cell activity. High concentrations of inhaled ozone can result in an itchy throat and chest tightness; chronic exposure scars the lung tissue, which can lead to emphysema. In addition, ozone interferes with the body's immune system, which compounds the danger from air or water-borne pathogens. Under current standards, the E.P.A. expects ozone to cause more than 110,000 lost work days and 1,100,000 lost school days between 2008 and 2020.

The design of the habitable environment 100 (FIG. 1) avoids or at least reduces the use of materials which emit VOCs, for example omitting or avoiding products or materials containing certain glues or resins (e.g., particle board). In day-to-day use, materials which emit VOCs are also avoided. For instance, the care or maintenance of the habitable environment 100 (FIG. 1), avoids the use of cleaning compounds which are known to result in VOC emission.

Nevertheless, some VOCs and other gaseous pollutants may appear in the habitable environment. Thus, the air treatment subsystem 208 may include one or more activated carbon air filters 249 in the flow path to reduce VOC, nitrogen dioxide, and ozone that pass through activated carbon media filters designed to intercept gas molecules. Activated carbon air filters 249 are most useful in areas with sources of fumes or odors.

Additionally or alternatively, the electrostatic filter 266 or some other element may optionally include one or more catalysts selected to catalyze certain impurities in the air. For instance, the electrostatic filter 266 may include one or more catalysts (e.g., non-metal catalysts for instance: titanium dioxide, chromium oxide or aluminum oxide, or metal catalysts for instance: Fe, Co, Ni, Cu, Ru, Rh, Pd, Ag, Ir, Pt and Au, as well as combinations or alloys thereof, such as an alloy of Pt and Rh) to catalyze species of VOCs into more acceptable or less harmful forms.

The air treatment subsystem 208 may include one or more heaters 269 to heat air. The heaters 269 may take any of a large variety of forms. Heaters 269 may take the form of various electric heaters, which employ a resistive radiant element to heat air. Heaters 269 may take the form of forced air heaters which typically include burners that burn a fuel such as natural gas or propane. Heaters 269 may alternatively take the form of oil furnaces, or the like.

The air treatment subsystem 208 may include one or more compressors 270 which may form part of an air conditioner cooling unit. The compressors 270 may be fluidly coupled to control pressure of a fluid, coupled with one or more coils or other heat exchangers, and may operate in a similar fashion to standard air conditioner units to remove heat from the air.

Relative humidity is the measure of water vapor in the air compared to the total amount that can be held at a given temperature. In the spring and summer months, humidity levels can be high enough to cause discomfort. When cool air flows through central air systems, humidity in the air is reduced, since cooler air holds less water vapor. However, as dry air is drawn in and heated within a building in the winter, relative humidity falls, so the air feels dry.

To maintain comfort, and prevent the establishment and growth of mold, dust mites, and bacteria, relative humidity in the habitable environment 100 should be kept between 30% and 50%. Using high-temperature water within the ventilation system of the home suppresses bacteria growth. Humidity towards the bottom of this range is better in terms of air quality, but extremely low moisture levels may lead to dry skin and respiratory irritation.

Thus, the air treatment subsystem 208 may include a humidifier and/or dehumidifier 271 which controls humidity throughout the enclosed habitable environment 100 (FIG. 1). This is particularly important when moisture levels in the air fall in winter, thus the air treatment subsystem 208 must increase the moisture (i.e., humidify) during dry periods. Conversely, the air treatment subsystem 208 lowers moisture (i.e., dehumidifies) during humid periods. The humidifier and/or dehumidifier 271 may include a reservoir (not shown) that retains water to either be added to the air in a humidification mode or removed from the air in a dehumidification mode. The humidifier and/or dehumidifier 271 may include a compressor (not shown) used to, for example cool air as part of removing moisture. The humidifier and/or dehumidifier 271 may optionally include a heating element to heat air as part of adding moisture.

To control relative humidity, the air treatment subsystem 208 may additionally employ exhaust vents 158a (FIG. 1), particularly in the bathroom 100b (FIG. 1), to increase the ventilation rate in that portion of the habitable environment in order to rapidly lower humidity generated therein, for example from showers 122, 132 (FIG. 1).

The air treatment subsystem 208 may include one or more fans and/or blowers 272 coupled to one or more ducts (FIG. 1) and/or vents (FIG. 1). The fans and/or blowers 272 may circulate air within the air treatment subsystem 208 and/or within the habitable environment 100 (FIG. 1). The fans and/or blowers 272 may expel air to an exterior environment and/or draw fresh air from the exterior environment, prior to treating the fresh air. In particular, a high flow ventilation system expels indoor air to reduce the buildup of internally generated air impurities such as volatile organic compounds, dust mites, and pet dander. A heat exchanger may advantageously be employed to recover energy from the outgoing air.

As an alternative for humidity control, a waterfall (not shown) in the enclosed space can both increase and decrease the relative humidity. When chilled water is circulated in the waterfall, the system absorbs water vapor from the air. When room temperature or warm water is circulated in the waterfall, the system releases water vapor into the air. The waterfall may also provide a soothing background sound in the habitable environment 100.

The air treatment subsystem 208 may include indoor air quality sensors that are connected to the HVAC system. Further, ventilation rates may increase if indoor air quality hits a particular threshold that would result in poor air quality. The indoor air quality sensors can detect the pollutants discussed above, such as mold, dust mites, bacteria, or VOCs. When certain thresholds of these pollutants are detected an alert can be transmitted to the user notifying that the filters in the system need to be changed or that some other action needs to be taken. Indoor relative humidity sensors are also connected to the HVAC system and air is humidified or dehumidified to stay within 30-50% relative humidity at all times.

Derived from traditional remedies, aromatherapy is the use of essential oils from herbs, flowers and trees to support emotional and spiritual well-being. Aromatherapy must be delivered through cool diffusion to avoid changing the natural properties of the essential oils. Some benefits of aromatherapy include alleviating anxious behaviors and aiding in relaxation. The practice of aromatherapy employs a wide variety of oils and extracts, with differing effects on mood and emotion. Supporters of contemporary aromatherapy practices suggest that various fruit and plant-based aromas have the ability to positively affect mood, behavior, and perceptions of wellness. Examples of plant-based scents and their corresponding benefits include:

Lavender effects include restful sleep during exposure at night increased vigor the morning after night time exposure enhanced mood, decreased heart rate and increased positive mood. Jasmine effects include relaxation, decreased heart rate and increased positive mood. Orange scent has been used to reduce anxiety and help maintain better mood in stressful circumstances. Rosemary has been shown to enhance memory and increases reaction times.

The scent subsystem 210 is operable to selectively dispense or disperse one or more scents into the air in the habitable environment 100 (FIG. 1) or portion thereof. The scent subsystem 210 may include a number of reservoirs 273 which hold various scents (e.g., lavender, rosemary), typically in a liquid form. One or more vents, valves or manifolds 274 are selectively operable to fluidly communicably couple selected ones of the reservoirs to emit or disperse scent into the habitable environment 100 (FIG. 1) or portion thereof, for example via ducts or vents of the air treatment subsystem 208. The scent subsystem 210 may optionally include one or more fans and/or blowers 275 to assist in dispersing the scent(s) into the habitable environment 100 (FIG. 1) or portion thereof. The scent subsystem 210 may optionally include one or more heaters 276, thermally (e.g., conductively, radiantly, convectively) coupled to the reservoirs 273 or an output of the reservoirs 273 to heat and thereby vaporize liquid forms of the scent(s) into a gaseous form more easily dispersible into the habitable environment 100 (FIG. 1) or portion thereof.

Additionally, or alternatively, one or more passive components may be employed to diffuse scents into the habitable environment 100. For example, various items or objects may be impregnated with specific scents. Such items or objects may include various fabrics, such as curtains, linens or bedding (e.g., pillow cases, pillows, sheets, blankets, comforters, duvets), carpets, towels, etc. Such items may include a pouch, sack or other breathable encasement or enclosure, which may be positioned at various locations about the habitable environment 100, for instance in a flow path of a vent or within a pillow case. The pouch or sack may be distributed in an air-tight packet, container or envelope which is opened immediately prior to use. Such may advantageously maintain the scent emitting materials fresh between manufacture and use, and may prevent undesired scents from being emitted into the habitable environment. Thus, certain packets may be opened to customize the scent to a specific occupant or occupants of the habitable environment 100, and the scent(s) allowed to disburse or disperse through the habitable environment 100.

Thus, active or passive components of a scent subsystem 210 deliver room-specific aromatherapy based on the room's function and aroma benefit. A wide variety of essential oils and crafted aromas are available for use in the dispenser with the option to tailor to individual specifications.

The sound subsystem 212 provides sound into the habitable environment 100 (FIG. 1) or portion thereof. In particular, the sound system may, for example, provide soothing sounds (e.g., running water, forest sounds, waves, "white" noise, "pink" noise, music). The sound subsystem 212 may include one or more speakers 277, which may be positioned throughout the habitable environment 100 (FIG. 1) or portion thereof. Sounds may be selected to produce relaxation or to allow an occupant to focus more intently then the occupant would focus without the sounds, for example while reading or working. The sound subsystem 212 may include one or more amplifiers 278 electrically, optically or wirelessly coupled to provide signals to the speakers 277 (e.g., typically analog or digital electrical signals) that cause the speakers 277 to reproduce the sounds represented by the signals. The sound subsystem 212 may optionally include a nontransitory computer- or processor-readable storage media 279 that stores digital versions of the sounds, for example in a library. The amplifier 278 may include one or more CODECs and/or microcontrollers to convert the digital versions of the sounds into signals for controlling the speakers 277. The sound subsystem 212 may include one or more microphones (not shown) to detect noise in the habitable space. The sound subsystem 212 may provide masking sound to offset or cancel the noise.

The input/output (I/O) subsystem 214 is communicatively coupled to the control subsystem 202 to supply input thereto and/or to provide output therefrom. The input/output (I/O) subsystem 214 may include various sensors 280-282, user operable input/output (I/O) devices, controls, panels or kiosks 283, 284, and other devices or components such as televisions 285.

For example, one or more occupant sensors or detectors 280 may be positioned in, or proximate the habitable environment 100 (FIG. 1) or portions thereof. The occupant sensor(s) or detector(s) 280 sense or detect a presence, or conversely an absence, of an occupant in the habitable environment 100 (FIG. 1). The occupant sensors or detectors 280 may take any of a large variety of forms. For example, the occupant sensor(s) or detector(s) 280 may take the form of various motion detectors, for instance passive infrared based motion detectors, proximity (RF) based motion detectors, microwave or radar based motion detectors, ultrasonic based motion detectors, vibration based motion detectors, and/or video based motion detectors. The occupant sensor(s) or detector(s) 280 may include simple contact switches which detect movement or operation of a fixture or some other element (e.g., turning on a radio, television, stereo, appliance) by an occupant. The occupant sensor(s) or detector(s) 280 may take the form of simple cameras (e.g., digital camera) which may capture images, from which changes from frame to frame may indicate a presence or absence of an occupant. The occupant sensor(s) or detector(s) 280 may detect a presence or absence of an object associated with the occupant, for instance a smartcard or keycard, or a handheld or mobile device.

Also for example, one or more temperature sensors or detectors 281 may be positioned in, or proximate the habitable environment 100 (FIG. 1) or portions thereof. The temperature sensor(s) or detector(s) 281 sense or detect a temperature proximate the temperature sensor or detector and provides signals to the control subsystem 202 and/or air treatment subsystem 208 indicative of the sensed or detected temperature. The temperature sensor(s) or detector(s) 281 may employ various components, for example thermocouples or thermally responsive resistors.

Also for example, one or more humidity sensors or detectors 282 may be positioned in, or proximate the habitable environment 100 (FIG. 1) or portions thereof. The humidity sensor(s) or detector(s) 282 sense or detect humidity or relative humidity proximate the humidity sensor or detector 282 and provides signals to the control subsystem 202 and/or air treatment subsystem 208 indicative of the sensed or detected humidity. The humidity sensor(s) or detector(s) 282 may employ various components.

One or more in-room user operable input/output (I/O) controls, panels or kiosks 283 may allow an occupant or facility personnel (e.g., cleaner, maintenance) to interact with the environmental control system 200. The in-room I/O control(s), panel(s) or kiosk(s) 283 may include a touch-sensitive or touch-responsive display, which allows presentation of information and a graphical user interface (GUI). The information may include information about the current settings of the environmental control system 200 and different settings which may be selected by the user. The GUI will include one or more user selectable icons (e.g., scroll bars, tool bars, pull down menus, dialog boxes, keys, text) displayed for selection by the user. Selection may allow the user to adjust illumination, temperature, humidity, sound, or other aspects of the environment. The GUI may present the user with a set of defined programs or scenes to select from The programs or scenes may be presented in a simple fashion with simple labels or names, yet may have fairly complicated sets of settings for various combinations of the subsystems 202-214.

The in-room user operable I/O control(s), panel(s) or kiosk(s) 283 may also allow collection of information from an occupant which is indicative of the occupant's impressions and overall satisfaction with the habitable environment 100, and particularly the health and wellness amenities, available scenes, scene adjustment capabilities, etc. Such may be captured with an automated survey, which includes various questions and possible ratings, presented for instance via a graphical user interface (GUI).

One or more facility user operable I/O controls, panels or kiosks 284 may allow facility personnel (e.g., clerk, concierge, cleaner, maintenance personnel) to interact with the environmental control system 200. The facility I/O control(s), panel(s) or kiosk(s) 284 may include a touch-sensitive or touch-responsive display, which allows presentation of information and a GUI. The information may include information about the current settings of the environmental control system 200 and different settings which may be selected by the user. The GUI will include one or more user selectable icons (e.g., scroll bars, tool bars, pull down menus, dialog boxes, keys, text) displayed for selection by the user. Selection may allow the user to adjust illumination, temperature, humidity, sound, or other aspects of the environment or otherwise control or set a scene in the environment. The GUI may present the user with a set of defined programs or scenes to select from. The programs or scenes may be presented in a simple fashion with simple labels or names, yet may have fairly complicated sets of settings for various combinations of the subsystems 202-214. The GUI may optionally allow facility personnel to define new programs or scenes, delete old programs or scenes, and/or modify existing programs or scenes.

The GUI may, for example, allow facility personnel to enter information about a specific guest or other occupant that will occupy a respective habitable environment. Information may, for example, include a location from which the occupant originated. The location may be specified in a variety of forms including name (e.g., city, state, country), geographic coordinates (e.g., latitude and/or longitude). Such may allow the environmental control system 200 to determine a control program or scene that accommodates for changes experienced by the occupant due to travel to a new location. Thus, the environmental control system 200 may adjust for changes in the diurnal cycle and/or circadian cycle. Information may include an age or approximate age of the occupant, which may affect or be related to circadian cycle and the ability to adjust for travel (e.g., "jet lag"). Such may allow accommodation or treatment for other issues, for instance seasonal effect disorder, or providing light therapy to treat certain aliments or symptoms.

As noted previously, one or more televisions 285 may be used to at least present information to an occupant. In some implementations, a control such as a remote control, may be used by the occupant to interact with the television 285 to make selection of various user selectable options for controlling one or more components of the environmental control system 200. As also previously noted, an occupant may use a handheld or mobile device 182c (FIG. 1), such as a smart phone, tablet computer, etc. to interact with environmental control system 200.

The server 244 and nontransitory computer- or processor-readable medium 246 may store and provide information to other components of the environmental control system 200. Such may, for instance, include a schedule that specifies which occupants will occupy which habitable environments 100 (FIG. 1) of the facility, and at what times. This information may also specify, or be mapped to, information which specifies desired environmental characteristics or scenes for the respective occupants. Thus, the environmental control system 200 may automatically adjust environmental characteristics or scenes in a variety of habitable environments 100, customized for the particular occupant.

A sanitizing subsystem 216 may be an integral part of the habitable environment 100, or may be selectively provided thereto or therein, for example when preparing for another occupant or guest. For instance, the sanitizing subsystem 216 may be provided as a cart 293 with wheels 294, as illustrated in FIG. 2, for selectively being wheeled into the habitable environment 100. While illustrated as a cart, the sanitizing subsystem 216 may be provided as a portable unit which may be hung from a pole mounted approximately centrally in the habitable environment, or wall or less preferably hung from a wall or other structure in the habitable environment 100. Such may advantageously allow the sanitizing subsystem 216 or portion thereof to be positioned at a higher point than might otherwise be achieved via a cart 293.

The sanitizing subsystem 216 may provide a sanitizing agent into the habitable environment 100 to destroy or render non-harmful various pests or pathogens. The sanitizing subsystem 216 may optionally evacuate the sanitizing agent from the habitable environment 100 (FIG. 1), after a sufficient time has passed for the sanitizing agent to destroy or render non-harmful the pests or pathogens.

The sanitizing agent may take a variety of forms. The sanitizing agent may be in a gaseous form, or may be a vapor or "dry vapor" (i.e., non-wetting) form. Suitable sanitizing agents may, for example, include forms chlorine dioxide, peracetic acid, hydrogen peroxide and electrochemically activated solutions (e.g., electrolyzed water). Suitable sanitizing agents may, for example, include photocatalytic antimicrobial materials (e.g., composite photocatalyst, nanoparticle sized zinc metal in a matrix of nano-crystalline titanium dioxide available under the trademark OXITITAN™ from EcoActive Surfaces, Inc. of Pompano Beach, Fla.). Such may provide an antimicrobial surface, reduce odor and VOCs, provide for hydrophilic or hydrophobic self-cleaning, and/or UV or corrosion protection. The UV protection may be particularly advantageous where UV illumination is also utilized in sanitizing the habitable environment 100.

Alternatively, or additionally, the sanitizing agent may be in the form of electromagnetic energy or radiation, for example specific ranges of wavelengths such as UV of electromagnetic energy.

A sanitizing subsystem 216 may include one or more reservoirs of sanitizing agent(s) or materials 286 which when combined produce a sanitizing agent. The sanitizing subsystem 216 may include one or more fans or blowers 287 to assist in dispersing the sanitizing agent into the habitable environment 100 (FIG. 1). In some implementations, the fan(s) or blower(s) 287 also assist in removing or evacuating the sanitizing agent into the habitable environment 100 (FIG. 1). The sanitizing subsystem 216 may optionally include one or more transducers 288 operable to place the sanitizing agent in a form more amenable to dispersion. The transducer(s) 288 may take the form of a heater, for example to vaporize sanitizing agent. Additionally, or alternatively, the transducer(s) 288 may take the form of one or more a high frequency vibration elements (e.g., piezoelectric element) to pulverize or otherwise particalize either dry sanitizing agent into a very fine particulate form or to break up droplets of liquid sanitizing agent into a very fine form, for instance that does not wet surfaces. Other types of transducers 288 may be employed.

The sanitizing subsystem 216 may include one or more ports or vents 289 for dispersing the sanitizing agent. Ports or vents 289 may be built into a housing 290 of the sanitizing subsystem 216. Additionally, or alternatively, the sanitizing subsystem 216 may include one or more hoses 291 with nozzles 292 or other openings for dispersing the sanitizing agent.

The sanitizing subsystem 216 may include one or more wands 295 selectively operable to emit electromagnetic energy or radiation, for example specific ranges of wavelengths such as UV of electromagnetic energy. The wand(s) 295 may include one or more illumination sources, for instance UV illumination sources 296 and may be electrically coupled to a power source 297 carried by the cart 293 via one or more cables 298. Alternatively, illumination sources 296 may be located in the cart 293, and the wand(s) 295 optically coupled thereto via one or more cables 298.

The sanitizing subsystem 216 may include one or more illumination sources 299 positioned so as to be exposed to the ambient environment in order to provide illumination into the habitable environment 100 directly from a housing of the sanitizing subsystem 216. The illumination sources 299 positioned on an exterior of the cart 293 or within the exterior of the cart 293 and optically communicatively coupled to the exterior via one or more optical ports (not shown). This may allow the general habitable environment 100 to be optically treated, for instance with UV illumination. The wand(s) 295 may, for instance, be used to treat areas or spaces that would not otherwise be treated via direct illumination from the illumination sources 299, for instance areas or spaces that are not in a direct line of sight of the illumination sources 299. In some implementations, the illumination sources 299 may provide the illumination which is optically coupled to the wand(s) 295 via the cable 298.

Sanitizing may require as little as three hours of exposure to UV illumination, dependent of a variety of factors such as type of pathogens, distance, and intensity (e.g., incident energies). Targeted pathogens may take a variety of forms, for example mold spores, and organisms such as various *bacillus*, protozoa, virus, yeast. Mold spores may include, for instance: *Aspergillius flavis, Aspergillius glaucus, Aspergillius niger, Mucor racemosus* A, *Mucor racemosus* B,

*Oospora lactis, Penicillium expansum, Penicillium roqueforti, Penicillium digitatum, Rhisopus nigricans.* Illumination may occur before, after, during, or before and after application of a photocatalytic antimicrobial agent or coating. Operation may require that the habitable space by vacant during the entire period of treatment. Thus a remote control (e.g., wireless handheld transmitter and wireless receiver in the cart 203) or a delay start timer may be advantageously employed.

Data, Data Structures, and Nontransitory Storage Media

Various nontransitory media discussed above may store information such as data including configuration information in one or more data structures. Data structures may take a variety of forms, for example records associated with relational databases, a database itself, lookup tables, etc. The data structures may store a variety of different information or data.

Operation

Figure 3:
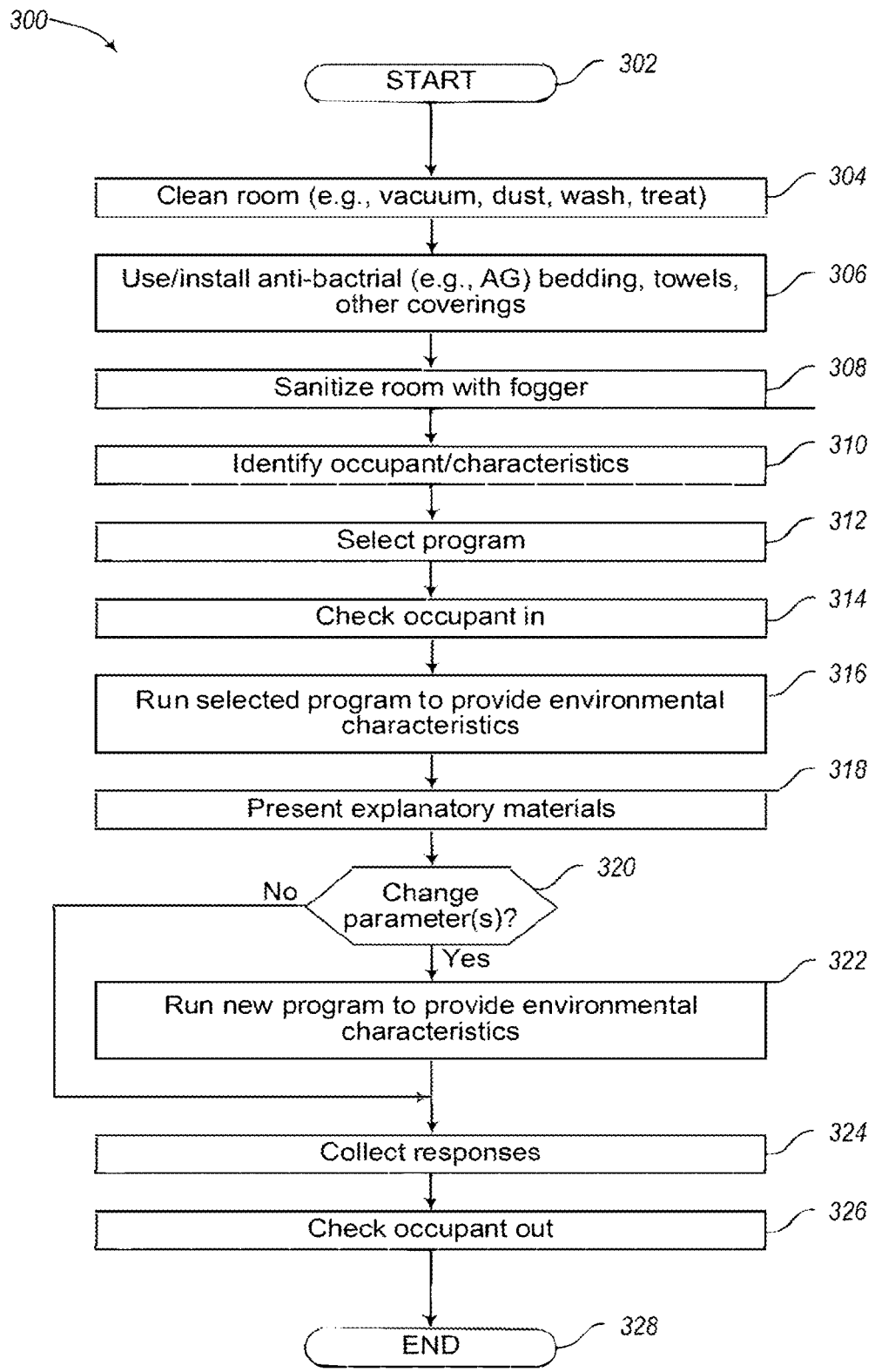
FIG. 3 is a flow diagram that shows a high level method of providing an enhanced environment in a habitable environment, according to one illustrated embodiment.

FIG. 3 shows a high level method 300 of providing an enhanced environment in a habitable environment 100, according to one illustrated embodiment. While often discussed in terms of a hotel, motel, spa or other hospitality environment, the habitable environment 100 may take the form of a home, office, hospital or any other inhabitable environment.

The method 300 starts at 302. The method 300 may, for example start on a periodic basis, for instance a daily, weekly, monthly. Alternatively, or additionally, the method 300 may start on demand, for instance in response to a checking in of a guest, or expected check in of a guest, or an entry of a guest or occupant into the habitable environment 100 (FIG. 1), for instance in response to reading an identifier from a smartcard or cardkey 114.

At 304, cleaning personnel clean the habitable environment 100. Such may include emptying waste receptacles, dusting, washing, vacuuming, cleaning and/or treating surfaces with disinfectants, and/or collecting soiled or used laundry (e.g., towels).

At 306, cleaning personnel use or install anti-bacterial bedding, towels, other coverings (e.g., drapes) in the habitable environment 100. The anti-bacterial bedding, towels, other coverings may for example be impregnated or coated with one or more an anti-bacterial or anti-pathogen agents.

At 308, cleaning personnel optionally sanitize the habitable environment 100 or portion thereof, for instance with a sanitizing subsystem 216. As previously explained, the sanitizing subsystem 216 may take a variety of forms, at least one of which is a fogger or "dry fogger" which disperses a fog or "dry fog" of a sanitizing agent into the habitable environment 100 (FIG. 1). The sanitizing agent may deposit on various surfaces, and may be left in place sufficiently long to neutralize or render pathogens or other undesirable substance harmless. As previously noted, the sanitizing agent may not "wet" the surfaces, thereby protecting the surfaces from damage. The sanitizing system 216 may then, optionally evacuate or otherwise remove the sanitizing agent from the habitable environment 100, for instance collecting such in a reservoir for disposal or recycling.

Optionally at 310, the environmental control system 200 or portion thereof identifies one or more occupants or guests that will inhabit the habitable environment 100 (FIG. 1) and/or specific attributes, traits or characteristics of the occupant(s). For example, facility personnel may enter an occupant identifier via an input device, panel or kiosk 284. Also for example, the occupant(s) or guest(s) may enter an occupant identifier via an input device, panel or kiosk 283.

As a further example, an occupant identifier may be automatically read from some piece of media, for instance a smartcard or keycard. The occupant identifier may, for example, be encoded in a magnetic stripe, machine-readable symbol, or wireless transponder (e.g., RFID transponder) of the smartcard or keycard. The occupant identifier may consist of or include the occupant's name, however preferable is an alphanumeric string which does not include the occupant's actual name. The alphanumeric string may be logically associated with the occupant's name, for example in a secure database or other secure data structure. Such an approach may enhance security.

The specific attributes, traits or characteristics of the occupant(s) may likewise be stored in a secured database or other secure data structure, or less preferably could be stored in the smartcard or card key. The specific attributes, traits or characteristics of the occupant(s) may specify information that allows customization of the habitable environment to the needs or desires of the occupant. For example, the specific attributes, traits or characteristics of the occupant(s) may identify one or more air temperatures, for example air or room temperatures for different times throughout a daily cycle. Also for example, the specific attributes, traits or characteristics of the occupant(s) may identify one or more air relative humidities, for example relative humidity for different times throughout a daily cycle. As another example, the specific attributes, traits or characteristics of the occupant(s) may identify one or more locations from which the occupant has traveled from. Such may permit adjustment of, for example lighting, to accommodate for jet lag, SAD, etc. As a further example, the specific attributes, traits or characteristics of the occupant(s) may identify one or more syndromes, aliments or conditions for which environmental characteristics or scenes may be adjusted to alleviate or treat. These may include syndromes, aliments or conditions which may be addressed by delivery of illumination (e.g., timed delivery of different intensities and/or wavelengths). This may also include syndromes, aliments or conditions which may be addressed by delivery of humidity, for instance various skin disorders or problems. These syndromes, aliments or conditions may be specified by name or an assigned identifier. Alternatively, or additionally, specific instructions or patterns may be stored for providing the desired environmental characteristics or scenes. Such may help maintain privacy for individuals, and may address regulatory issues (e.g., HIPAA) related to the care, handling and management of health related information such as electronic medical records. Thus, for example, a pattern of illumination which specifies wavelengths and intensities at various times throughout the solar day may be stored. Patterns specifying air temperature, relative humidity, sound, scents, and other ambient environmental characteristics or scenes may likewise be stored for various times throughout the solar day. These patterns may be synchronized with one another. Thus, for example, illumination and sound may be synchronized to produce a gradual wakeup period in which light gradually increases in intensity as does soothing sounds. The wavelengths of light may likewise gradually change during this wake up period. Also for example, illumination and sound may be synchronized to produce a gradual relaxation period prior to a sleep time in which light gradually decreases in intensity as does soothing sounds. The wavelengths of light may likewise gradually change during this relaxation up period.

Optionally at 312, facility personnel, the occupant, or the environmental control system 200 or portion thereof selects a program to execute to provide the environmental characteristics, attributes or amenities, which may include or comprise a scene in a space or sub-space. Such may be done, for example, where no program has previously been specified or identified. Alternatively, such may be done where multiple programs are specified for a given occupant. As previously noted, the one or more programs may be stored for each perspective occupant, for example stored in a smartcard or keycard 114 or stored in a database in a nontransitory computer- or processor-readable media 246. These programs or identifiers representing these programs may be presented to the facility personal or occupant to select from, for instance via one or more an input device, panel or kiosk 283, 284. Alternatively, or additionally, the control subsystem 202 (FIG. 2) may select a program or scene, for example based on certain criteria about the occupant. For instance, the control subsystem 202 (FIG. 2) may determine that the occupant has recently traveled from a location with a significantly different natural light cycle from that of the location of the habitable environment 100 (FIG. 1). Thus, the control subsystem 202 (FIG. 1) may select a program or scene which provides specific illumination or other characteristics that alleviates or otherwise addresses symptoms or aliments associated with such changes in natural illumination due to the travel, such as jet lag or SAD.

A set of patterns or scenes may be defined which accommodate changes in total amount of natural light and/or the spectral components (e.g., wavelengths) of the natural light for a large numbers of pairs of origination and arrival locations, where the origination location is a location from which the occupant departs from (e.g., typically the occupant's home) and the arrival location is a location to which the occupant has traveled (e.g., a hotel, motel, spa). These patterns may, for example, relate each of 24 time zones (e.g., zones of longitudes) to the other 23 time zones throughout the World. These patterns may relate to various latitudes or zones of latitudes throughout the World. For instance, patterns or scenes may be established for each pair of latitude zones (e.g., 5 degree increments of latitude) north and south of the equator. Thus, each latitude zone may be related to each other latitude zone by a respective pattern. Patterns may likewise be defined for various pair of geographical locations (e.g., longitude or time zone, and latitude) to simultaneously accommodate for both time zone changes and changes in length of solar day. Patterns do not have be established for all possible pairs of geographic locations since most occupants will arrive from a relatively small number of geographic locations, and since the geographic location of the arrival location is presumably known for any given inhabitable environment 100 (FIG. 1). Likewise, grouping longitudes by, for instance time zone, and/or latitudes into bands (e.g., 5 degrees) will also limit the total number of stored patterns. While described as being stored, in some implementations, patterns or other scenes may be generated dynamically or "on the fly" via one or more algorithms or equations using geographic locations as input.

Optionally at 314, facility personnel may check in or register one or more occupants, for use of the habitable environment 100 (FIG. 1), in a similar or identical manner as that performed at most hotels, motels, spas or hospitals. The identification of the occupant or guest at 310 and/or the selection of the program at 312 may be performed as part of this check or registration. Alternatively, identification of the occupant or guest at 310 and/or the selection of the program at 312 may be performed prior to this check in or registration 314, for example as part of booking or reserving the habitable environment 100 (FIG. 1) as an accommodation.

At 316, the control subsystem 202 (FIG. 2) runs the selected program to cause the various subsystems 202-214 to provide the environmental characteristics, scenes or amenities in the habitable environment 100 (FIG. 1).

Optionally at 318, the control subsystem 202 or a portion of the environmental control system 200 present explanatory materials which explanation the operation and benefits of the habitable space including the various active and passive components. Such may include presentation of a tutorial, for instance in a video form, explaining how a user may operate or otherwise interact with the environmental control system 200.

At 320, from time-to-time the control subsystem 202 or a portion of the environmental control system 200 determines whether a change has been made to any of the operational parameters for a scene. Changes may, for example, be made by occupant(s) and/or facility personnel, or via sensed or detected conditions in the habitable environment 100 (FIG. 1). For example, the occupant(s) or facility personnel may change a setting for air temperature, relative humidity, illumination, scent dispersal, or other parameter. The change(s) may be temporary or one time changes, or may be more permanent changes that will be stored for use on another occasion or for use with another habitable environment 100 (FIG. 1). Thus, the control subsystem 202 or a portion of the environmental control system 200 may generate a new program or scene, or execute an existing program or scene with new or modified parameters, hence in effect constituting a new program or scene.

If a change has been made, at 322 the control subsystem 202 or a portion of the environmental control system 200 runs the new program, scene or program with new parameters to provide environmental characteristics or scenes. Execution of the new program causes the various subsystems 202-214 to provide the environmental characteristics, scenes or amenities in the habitable environment 100 (FIG. 1) in accordance with the new parameters.

Optionally at 324, optionally the control subsystem 202 or a portion of the environmental control system 200 collects responses from the occupant(s) with respect to the habitable environment 100 (FIG. 1). In particular, the control subsystem 202 or a portion of the environmental control system 200 may provide an opinion survey and/or questions regarding the occupant(s) objective and/or subjective impressions of the effect of the accommodations on their overall health and/or wellness or sense of wellness. Such may also inquire regarding actual operation of the environmental control system 200, as well as the ease of use or interaction with the same. The survey or questions may provide a scale for rating the occupant's experience, and in particularly sense of wellbeing.

Optionally at 326, facility personnel check out the occupant or guest. The facility personnel preferably actively inquire about the occupant's or guest's sense of wellbeing and experience with the amenities of the habitable environment 100 (FIG. 1). At this time, the facility personnel may update patterns or scenes, store new patterns or scenes, and/or delete old patterns or scenes associated with the particular occupant or guest, providing a refined experience on the occupant's next visit or use of the habitable environment 100 (FIG. 1) or other inhabitable environment 100 (FIG. 1) for instance at another location.

The high level method 300 may terminate at 328 until started again, or may continually repeat. Alternatively, the high level method 300 may run concurrently with other methods or processes.

Figure 4:
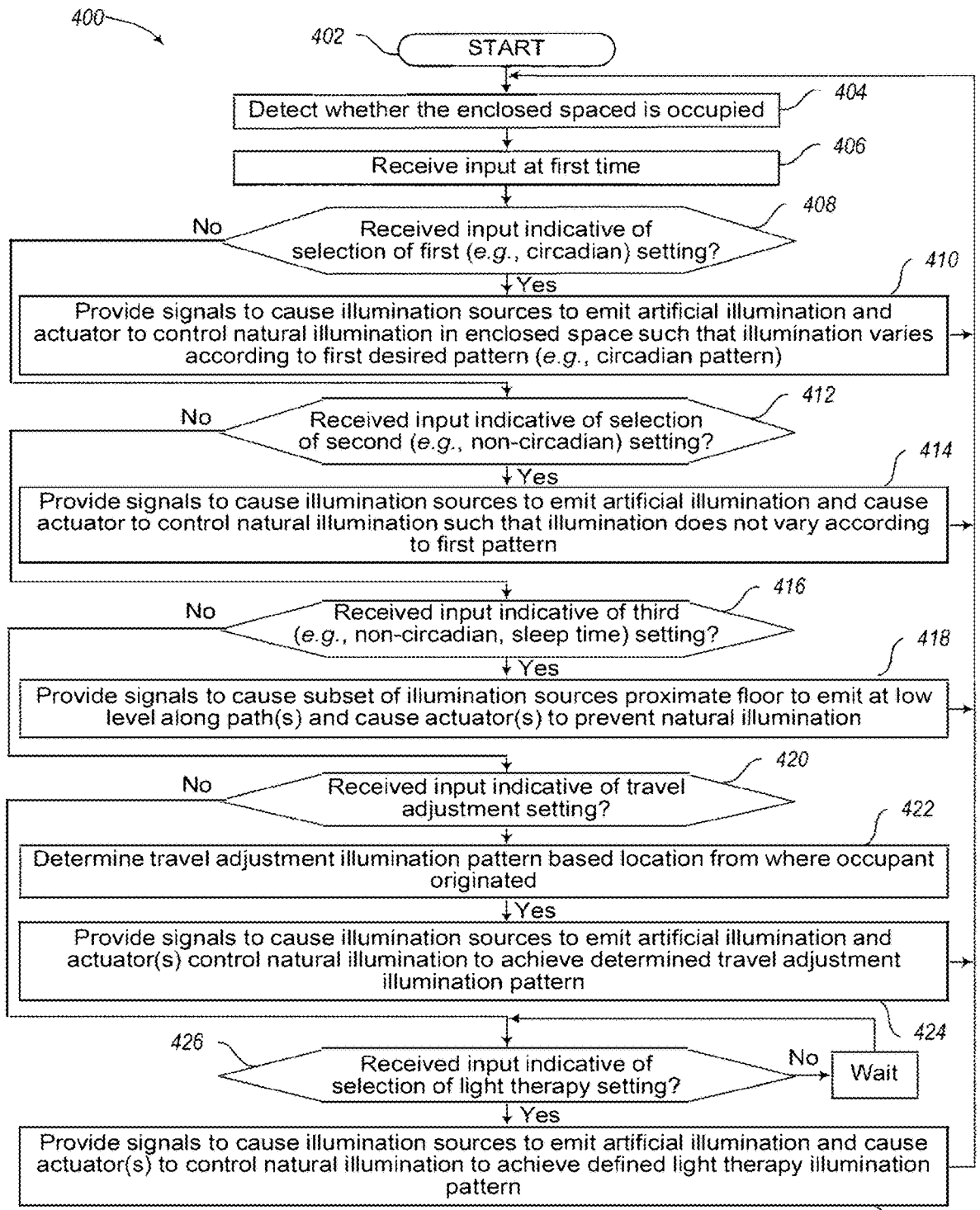
FIG. 4 is a flow diagram that shows a low level method of operating one or more components of a habitable environment enhancement system for providing illumination, according to one illustrated embodiment, which may be useful in performing at least a portion of the method illustrated in FIG. 3.

FIG. 4 shows a low level method 400 of operating one or more components of a habitable environment enhancement system for providing illumination, according to one illustrated embodiment, which may be useful in performing at least a portion of the method 300 illustrated in FIG. 3.

The low level method 400 starts at 402. The method 400 may, for example run continuously, or may start on a periodic basis, for instance a every few minutes, hourly, daily, weekly, monthly. Alternatively, or additionally, the method 400, or portions thereof, may start on demand, for instance in response to detection of an occupant of the habitable environment 100, or in response to a request by a guest or operator of a facility (e.g., hotel, spa, resort, hospital).

Optionally at 404, a sensor or detector senses or detects whether the enclosed spaced is occupied. The sensor(s) may, for example, provide signals to the control subsystem indicative of whether the enclosed space is occupied. One or more of the following acts may be selectively performed based in the signals. For example, it may be more energy efficient to avoid providing active illumination when the habitable environment is not occupied.

At 406, a control subsystem receives an input, for example at a first time. The input may be indicative of any of a number of settings, for instance settings related to illumination to be provided in an enclosed space. The input may be received via at least one user actuatable input device located within the enclosed space or at an entrance to the enclosed space. Additionally, or alternatively, input may be received via at least one user actuatable input device located remotely from the enclosed space. For example, located at a reception, concierge, building maintenance or other centralized location associated with the building.

At 408, the control subsystem determines whether the received input is indicative of a selection of a first setting. The first setting may, for example, be a circadian setting, that is a setting or pattern of illumination that is consistent with and establishes a natural circadian rhythm or cycle in a human. Such may, for example, mimic the intensity and chromatic makeup of natural sunlight and darkness over a solar day at some given location on the Earth.

At 410, in response determining the first input indicates a first setting, the control subsystem provide signals to cause at least some of the illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination varies over a first period of time according to a first pattern. The first pattern may, for example be a circadian pattern (e.g., pattern consistent with and which establishes a natural circadian rhythm or cycle in a human).

At 412, the control subsystem determines whether the received input is indicative of a selection of a second setting. The second setting may be a first non-circadian setting, that is any setting or pattern of illumination other than a setting or pattern of illumination that is consistent with and establishes a natural circadian rhythm or cycle in a human.

At 414, in response to the second input the control subsystem provides signals to cause the illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination does not vary over a second period of time according to a non-circadian pattern (e.g., any pattern other than a pattern consistent with and which establishes a natural circadian rhythm or cycle in a human). For example, in response to the second input, the control subsystem may provide signals to the illumination sources and the actuator(s) such that the combination of the artificial and the natural illumination remains constant over the second period of time.

At 416, the control subsystem determines whether the received input is indicative of a selection of a second non-circadian setting that is a sleep time setting at a third time.

At 418, in response to the third input the control subsystem provides signals to cause a subset of the illumination sources proximate to a floor in the enclosed space to emit artificial illumination at a low illumination level along at least one path. The signals may further cause the at least one actuator to prevent natural illumination from being received into the enclosed space via the one or more windows.

At 420, the control subsystem determines whether the received input is indicative of a selection of a travel adjustment setting.

At 422, in response to the fourth input the control subsystem determines a travel adjustment illumination pattern based at least in part on a geographic location from where an occupant of the enclosed spaced originated to accommodate a change in circadian rhythm due to travel by the occupant. At 424, also in response to the fourth input, the control subsystem provides signals to cause the illumination sources to emit artificial illumination at the levels and the wavelengths and to cause the at least one actuator to control at least the level of natural illumination received into the enclosed space via the one or more windows such that the combination of the artificial and the natural illumination achieves the determined travel adjustment illumination pattern in the enclosed space.

At 426, the control subsystem determines whether the received input is indicative of a selection of a light therapy setting at a fourth time.

At 428, in response to the fourth input indicative of the light setting, providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the defined light therapy illumination pattern in the enclosed space over a therapeutic period of time.

The method 400 may repeat as indicated by arrow 430. Alternatively, the method 400 may terminate until called again or otherwise restarted.

FIG. 5 shows a low level method 500 of operating one or more components of a habitable environment enhancement system to adjust an amount of natural light received in the habitable environment using electrochromatic panes, according to one illustrated embodiment, which may be useful in performing at least a portion of the method 400 illustrated in FIG. 4.

At 502, control subsystem provides signals to control an actuator (e.g., voltage or current supply) drivingly coupled to electrochromatic pane to adjust illumination passed thereby. For example, the signals may cause the drape(s)/shade(s)/curtain(s) (collectively window coverings) to move to a fully closed position which completely or substantially blocks natural light from entering the habitable environment 100 or portion thereof via the window(s). Alternatively, the signals may cause the drape(s)/shade(s)/curtain(s) to move to a fully open position which allows a maximum amount of natural light to enter the habitable environment 100 or portion thereof via the window(s). The signals may cause the drape(s)/shade(s)/curtain(s) to move to a variety of intermediate positions between the fully closed and fully open positions, which intermediate positions allow respective amounts of natural light to enter the habitable environment 100 or portion thereof via the window(s).

Since the intensity of natural light in the ambient environment varies throughout the day, and from day to day, control may be based at least in part to one information from one or more light sensors or detectors. The light sensors or detectors may sensor or detect natural light in the exterior ambient environment and provide the control subsystem with signals indicative of an intensity or spectral power distribution thereof. Additionally or alternatively, the light sensors or detectors may sensor or detect light in the habitable environment 100 or portion thereof and provide the control subsystem with signals indicative of an intensity thereof.

FIG. 6 shows a low level method 600 of operating one or more components of a habitable environment enhancement system to adjust an amount of natural light received in the habitable environment using drapes or shades or curtains or other window coverings, according to one illustrated embodiment, which may be useful in performing at least a portion of the method 400 illustrated in FIG. 4.

At 602, control subsystem provides signals to control an actuator (e.g., electrical motor, solenoid) drivingly coupled via a transmission to move drape(s)/shade(s)/curtain(s) relative to a window. For example, the signals may cause the drape(s)/shade(s)/curtain(s) to move to a fully closed position which completely or substantially blocks natural light from entering the habitable environment 100 or portion thereof via the window(s). Alternatively, the signals may cause the drape(s)/shade(s)/curtain(s) to move to a fully open position which allows a maximum amount of natural light to enter the habitable environment 100 or portion thereof via the window(s). The signals may cause the drape(s)/shade(s)/curtain(s) to move to a variety of intermediate positions between the fully closed and fully open positions, which intermediate positions allow respective amounts of natural light to enter the habitable environment 100 or portion thereof via the window(s).

Since the intensity of natural light in the ambient environment varies throughout the day, and from day to day, control may be based at least in part to one information from one or more light sensors or detectors. The light sensors or detectors may sensor or detect natural light in the exterior ambient environment and provide the control subsystem with signals indicative of an intensity thereof. Additionally, or alternatively, the light sensors or detectors may sensor or detect light in the habitable environment 100 or portion thereof and provide the control subsystem with signals indicative of an intensity thereof.

Figure 7:
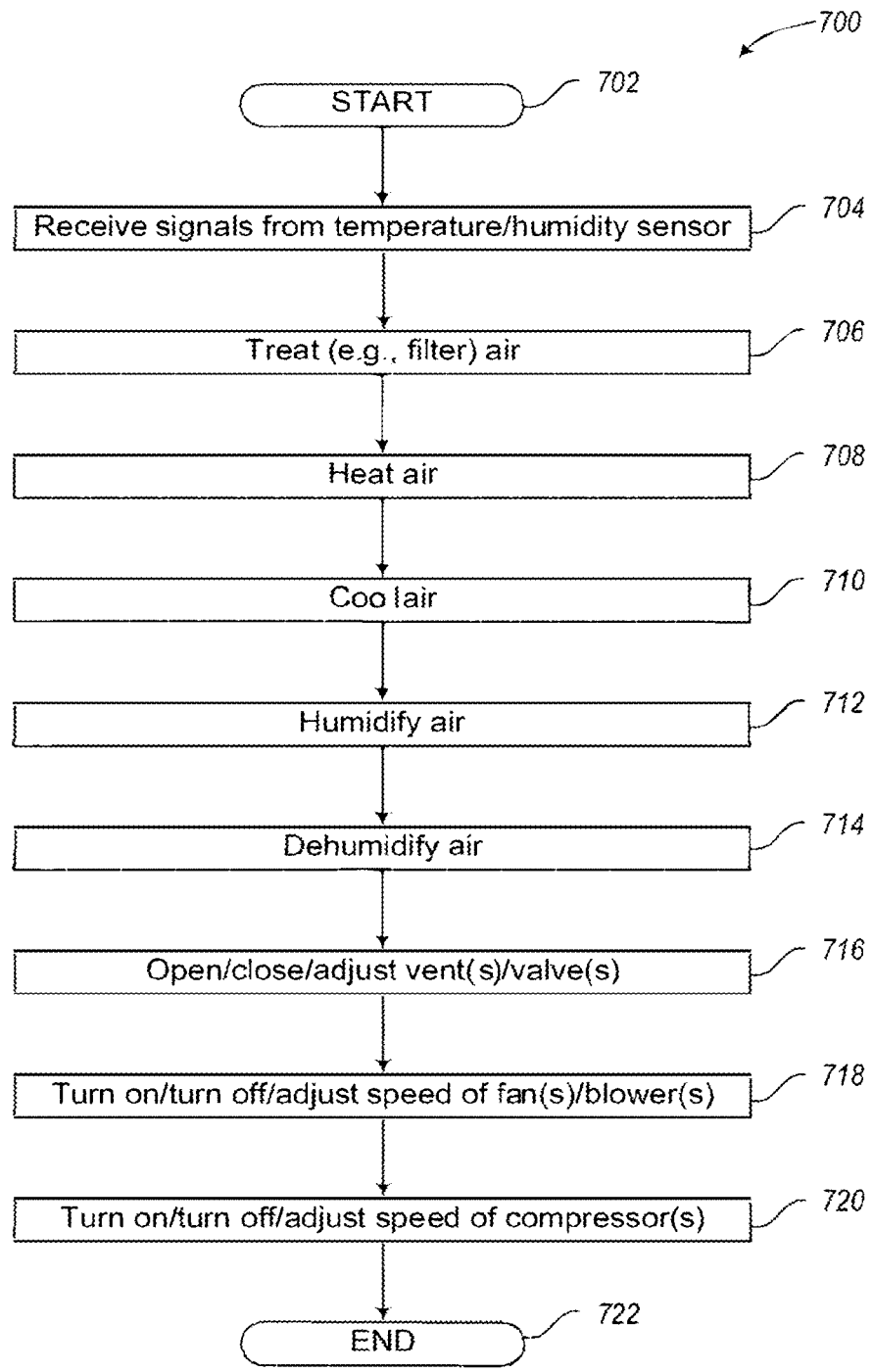
FIG. 7 is a flow diagram that shows a low level method of operating one or more components of a habitable environment enhancement system for providing heating, ventilation and cooling of a habitable environment, according to one illustrated embodiment, which may be useful in performing at least a portion of the method illustrated in FIG. 3.

FIG. 7 shows a low level method 700 of operating one or more components of a habitable environment enhancement system for providing heating, ventilation and cooling of a habitable environment 100, according to one illustrated embodiment, which may be useful in performing at least a portion of the method 300 illustrated in FIG. 3. Typically, only a few of the acts identified in method 700 will be performed in any single pass. For example, cooling of air is unlikely to be performed if the air has just been heated, or dehumidifying is unlikely to be performed in humidification was just performed. Thus, method 700 provides more of a comprehensive illustration of the acts that may be performed.

The low level method 700 starts at 702. The method 700 may, for example run continuously, or may start on a periodic basis, for instance every few minutes, hourly, or daily. Alternatively, or additionally, the method 700 may start on demand, for instance in response to an adjustment of a thermostat, entry into a user input device, or sensed or detected presence of an occupant in the habitable environment 100 or portion thereof.

At 704, the control subsystem receives signals from at least one of a temperature or humidity sensor or detector which signals are indicative of a sensed or detected temperature and/or humidity in habitable environment 100 or portion thereof. The signals may be used in order to adjust at least one or a temperature and/or humidity of the air in the habitable environment 100, for example based at least in part on a circadian pattern over a period of time.

At 706, the control subsystem provides signals that cause air to be treated. The signals may, for example, turn ON, turn OFF, and/or adjust a speed of one or more fans or blowers. The signals may additionally or alternatively, adjust a position of a vent, damper, valve or manifold. Such may circulate or otherwise cause air to be treated by filtering via one or more mechanical (NEPA) air filters. Such may circulate or otherwise cause air to be treated by filtering via one or more electrostatic particle air filters, a voltage being supplied according the signals. Such may circulate or otherwise cause air to be treated by exposure to ultraviolet illumination via an air ultraviolet sanitizer.

At 708, the control subsystem provides control signals which cause air to be heated. For example, the control subsystem may provide signals to a heater (e.g., forced air furnace, steam radiator) to heat air. Also for example, the control subsystem may provide signals to open, close or adjust an opening of a vent, damper, valve or manifold which routes warm air to the habitable environment 100 or portion thereof.

At 710, the control subsystem provides control signals which cause air to be cooled. For example, the control subsystem may provide signals to a cooler (e.g., air condition, swamp cooler) to cool (i.e., remove heat from) the air. Also for example, the control subsystem may provide signals to open, close or adjust an opening of a vent, damper, valve or manifold which routes cool air to the habitable environment 100 or portion thereof.

At 712, the control subsystem provides control signals which cause air to be humidified. For example, the control subsystem may provide signals to a humidifier to humidify (i.e., add moisture) to the air. Also for example, the control subsystem may provide signals to open, close or adjust an opening of a vent, damper, valve or manifold which routes humidified air to the habitable environment 100 or portion thereof.

At 714, the control subsystem provides control signals which cause air to be dehumidified. For example, the control subsystem may provide signals to a dehumidifier to dehumidify (i.e., remove moisture) from the air. Also for example, the control subsystem may provide signals to open, close or adjust an opening of a vent, damper, valve or manifold which routes dehumidified air to the habitable environment 100 or portion thereof.

At 716, the control subsystem opens, closes, or otherwise adjusts one or more vents or dampers or valves or manifolds. Operation of various vents, dampers, valves or manifolds may provide fresh air, conditioned air, and/or scents or aromas to the habitable environment 100 or a portion thereof. The vents or dampers or valves or manifolds may be operated via one or more actuators, for example electric motors or solenoids, or shape memory alloy actuators, spring loaded actuators and/or magnetic actuators.

At 718, the control subsystem provides control signals which cause air to be moved or circulated. For example, the control subsystem may provide signals to one or more fans or blowers to move or circulate the air. The signals may turn ON, turn OFF and/or adjust a speed of a fan or blower.

At 720, the control subsystem provides control signals which cause air to be compressed. For example, the control subsystem may provide signals to one or more compressors to compress air, for instance to remove moisture or as part of removing heat. The signals may turn ON, turn OFF, or otherwise adjusts a speed of a compressor.

The low level method 700 may terminate at 722 until called again, or may continually repeat. Alternatively, the low level method 700 may run concurrently with other methods or processes, for example, as one of multiple threads on a multi-threaded processor system.

Figure 8:
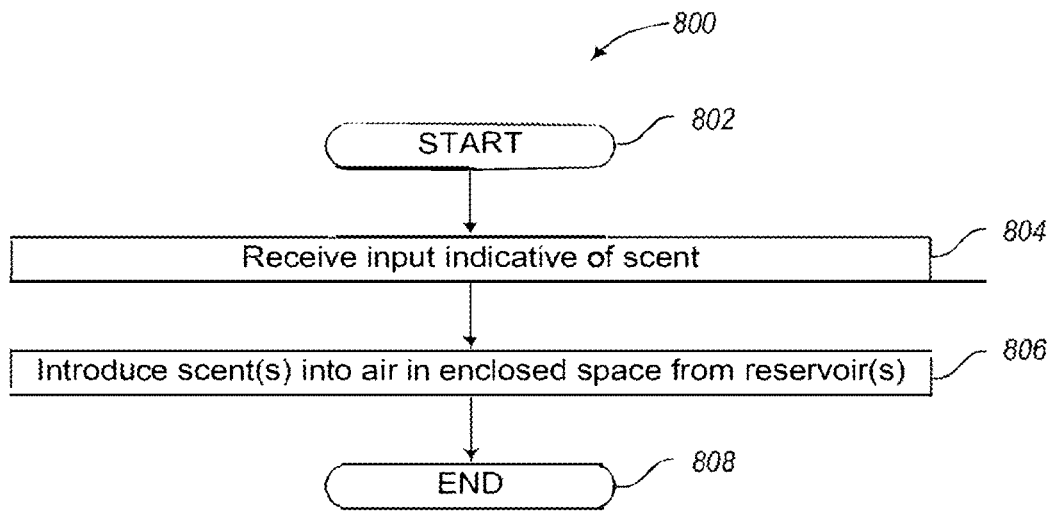
FIG. 8 is a flow diagram that shows a low level method of operating one or more components of a habitable environment enhancement system for introducing scents or aromas into a habitable environment, according to one illustrated embodiment, which may be useful in performing at least a portion of the method illustrated in FIG. 3.

FIG. 8 shows a low level method 800 of operating one or more components of a habitable environment enhancement system for introducing scents or aromas into a habitable environment, according to one illustrated embodiment, which may be useful in performing at least a portion of the method 300 illustrated in FIG. 3.

The low level method 800 starts at 802. The method 800 may, for example start on a periodic basis, for instance every few minutes, hourly, or daily. Alternatively, or additionally, the method 800 may start on demand, for instance in response to a request by a guest or operator of a facility (e.g., hotel, spa).

At 804, the control subsystem receives input indicative of a scent to be dispersed the habitable environment 100 or portion thereof. The input may come from an in room control panel, a remote control panel, a handheld device (e.g., smart phone, tablet computer, or personal digital assistant), or may be generated as part of execution of a program (also referred to as a scene) by a control subsystem.

At 806, the control subsystem provides signals which cause one or more scents to be introduce into air in the habitable environment 100 or portion thereof. The scent(s) may be delivered from one or more reservoirs. The signals may cause a vent, damper, valve, or manifold to open, or alternatively close, allow scent to enter the habitable environment 100 or portion thereof. The signals may additionally or alternatively cause one or more fans or blowers to cause the scent(s) to be delivered the habitable environment 100 or portion thereof or dispersed or circulated therein. Additionally, or alternatively, the signals may cause a heater to heat scented material, for instance to vaporize the material to cause the scent to be dispersed into air which is circulated into the habitable environment 100 or portion thereof.

The control subsystem may provide the signals to cause the scent(s) to be introduced according to or based on a defined schedule. Alternatively, or additionally, the control subsystem may provide the signals to cause the scent(s) to be introduced on demand, for example in response to a user input.

The low level method 800 may terminate at 808 until called again, or may continually repeat. Alternatively, the low level method 800 may run concurrently with other methods or processes, for example, as one of multiple threads on a multi-threaded processor system.

Figure 9:
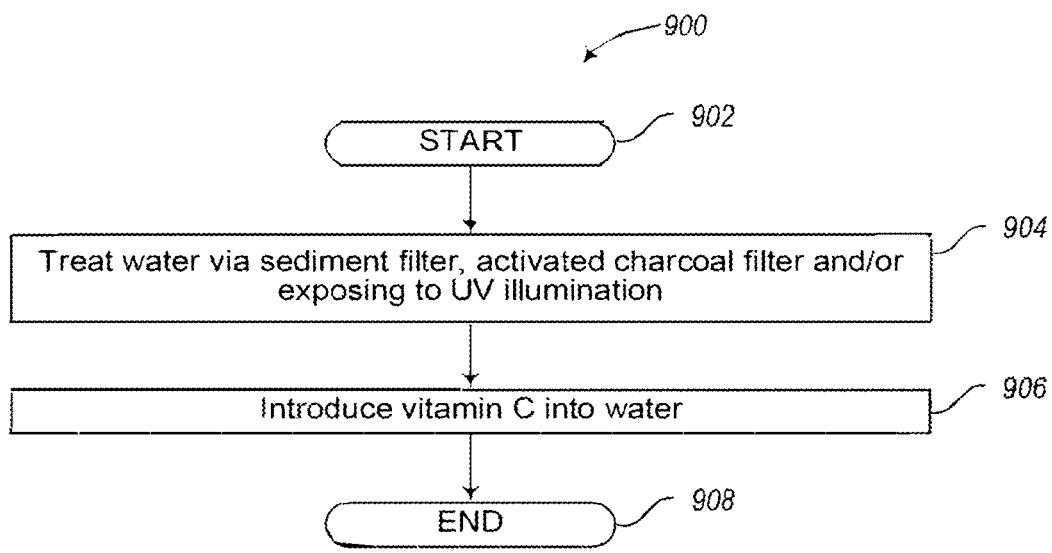
FIG. 9 is a flow diagram that shows a low level method of operating one or more components of a habitable environment enhancement system for treating water for use in a habitable environment, according to one illustrated embodiment, which may be useful in performing at least a portion of the method illustrated in FIG. 3.

FIG. 9 shows a low level method 900 of operating one or more components of a habitable environment enhancement system for treating water for use in a habitable environment, according to one illustrated embodiment, which may be useful in performing at least a portion of the method 300 illustrated in FIG. 3.

The low level method 900 starts at 902. The method 900 may, for example run continuously, or may start on a periodic basis, for instance every few minutes, hourly, or daily. Alternatively, or additionally, the method 900 may start on demand, for instance in response to use of water by an occupant of the habitable environment 100.

At 904, one or more water treatment components of a water supply subsystem treat a supply of water to a faucet or a showerhead of the habitable environment 100. Treating water may, for example include filtering water using one or more sediment or coarse particle filters. Treating water may additionally or alternatively include fine filtering of water, for example, using one or more activated charcoal filters. Treating water may additionally or alternatively include exposing the water to ultraviolet illumination of sufficient intensity and duration as to sanitize the water.

At 906, one or more water treatment components of the water supply subsystem introduce vitamin C into at least some of the water. For example, one or more valves or manifold may release vitamin C from a reservoir of vitamin C into water that is to be supplied the showerhead of the habitable environment 100.

The low level method 900 may terminate at 908 until called again, or may continually repeat. Alternatively, the low level method 900 may run concurrently with other methods or processes, for example, as one of multiple threads on a multi-threaded processor system.

Figure 10:
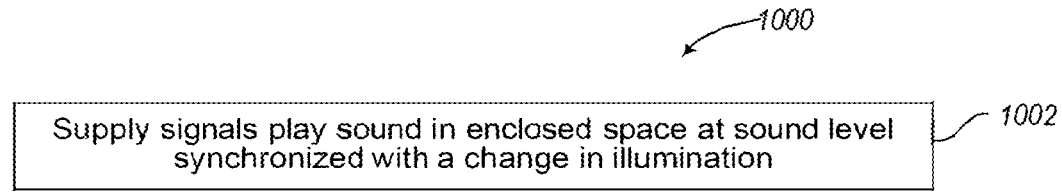
FIG. 10 is a flow diagram that shows a low level method of operating one or more components of a habitable environment enhancement system for adjusting an acoustical aspect of a habitable environment, according to one illustrated embodiment, which may be useful in performing at least a portion of the method illustrated in FIG. 3.

FIG. 10 shows a low level method 1000 of operating one or more components of a habitable environment enhancement system for adjusting an acoustical aspect of a habitable environment, according to one illustrated embodiment, which may be useful in performing at least a portion of the method 300 illustrated in FIG. 3.

The method 1000 may, for example start on a periodic basis, for instance every few minutes, hourly, or daily. Alternatively, or additionally, the method 1000 may start on demand, for instance in response to a request by a guest or operator of a facility (e.g., hotel, spa). Alternatively, or additionally, the method 1000 may start in response to a call or signal from a program executed by the control subsystem, for instance in synchronization with some other aspect of the environment. For instance, sound may be triggered by an alarm clock setting, which is synchronized with light levels and/or spectrum.

In particular, the control subsystem provides signals which cause at least one speaker to play sound in the enclosed space at a sound level that changes in synchronization with a change in a level of illumination emitted by the illumination sources at 1004.

The low level method 1000 may terminate at until called again, or may continually repeat. Alternatively, the method 1000 may run concurrently with other methods or processes, for example, as one of multiple threads on a multi-threaded processor system.

Modifications

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems, not necessarily the exemplary system generally described above.

The control subsystem or some other processor-based system such as a personal computer, may be programmed to evaluate a "wellness" of a given space. The system may assess various amenities provided in the environmental space, including type and effectiveness of the amenities. For instance, the system may assign points for particular types of amenities and/or effectiveness. For example, points may be assigned for having active lighting subsystem, which additional points for active lighting which can positively influence circadian patterns. Also for example, points may be assigned for air treatment, with a total number of points based on effectiveness of the air treatment. Also for example, points may be assigned for water treatment, with a total number of points based on effectiveness of the water treatment. Points may be required in each possible category (e.g., lighting, air, water, sound, reduced use of VOC leaching materials, use of sound absorbent or damping materials, use of materials that cushion or absorb shocks to protect the occupant). Alternatively, points may be required for a subset of categories. Additionally, or alternatively, a minimum number of points may be required in each of a number of categories, or a minimum cumulative score required to obtain a given rank or wellness rating. Ranks or wellness ratings may be certified and used in advertising. Wellness may be reassessed from time to time.

Wellness may be assessed based on self-reported scores or scores assigned by a reviewer or examiner. The scores may be reported via various user input devices, for instance a keyboard, keypad, or touch panel associated with a GUI. The scores may, for instance, be entered via a Webpage user interface, and communicated to the system for evaluation. The system may perform comparisons of a given facility from year to year, or between different facilities. The evaluation may be compared or scored against a defined set of wellness standards in each of a number of categories or pathways.

Wellness scores need not be dependent on self-reports, but may be inferred from environmental sensors and occupant-based biometrics. For example, data gathered passively or actively from devices in the built environment, furniture or other biometric-reading devices, can contribute to a personal wellness score that can be used to directly or indirectly control elements in the built environment including lighting, sound, HVAC or other categories previously discussed. Relevant biometrics may include any health or wellness-related measurements, including but not limited to heart rate, heart-rate variability, sleep phase, sleep length, or respiration rate, walking steps per day, body weight, or BMI.

The control system may cause a display of a dashboard which provides a concise representation of environmental information to occupants of the habitable environment 100 and/or to personnel of the facility (e.g., hotel) which houses the habitable environment 100 (e.g., room or suite). The dashboard may additionally present tips, suggestions, questionnaires, suggested settings, interventions, activities, health/wellness educational information, etc. The dashboard may be presented via a Website or Webpage and/or may be stored "in the cloud". The dashboard may be accessible via any type of processor-based device including mobile devices (e.g., smart phones, tablet computers) as a Webpage or a dedicated application. Such devices may include transducers that act based on the information and/or to control various environmental aspects of or scenes in the habitable environment via the control subsystem. For example, the Webpage or application may communicatively integrated the mobile device with the lighting subsystem and/or other environmental systems and controls.

For instance, a habitable environment may include any combination of one or more of the passive or active components. Some components may reside in, or be controlled as part of a different subsystems than illustrated.

Also for instance, while various methods and/or algorithms have been described, some or all of those methods and/or algorithms may omit some of the described acts or steps, include additional acts or steps, combine acts or steps, and/or may perform some acts or steps in a different order than described. Some of the method or algorithms may be implemented in software routines. Some of the software routines may be called from other software routines. Software routines may execute sequentially or concurrently, and may employ a multi-threaded approach.

Figure 11:
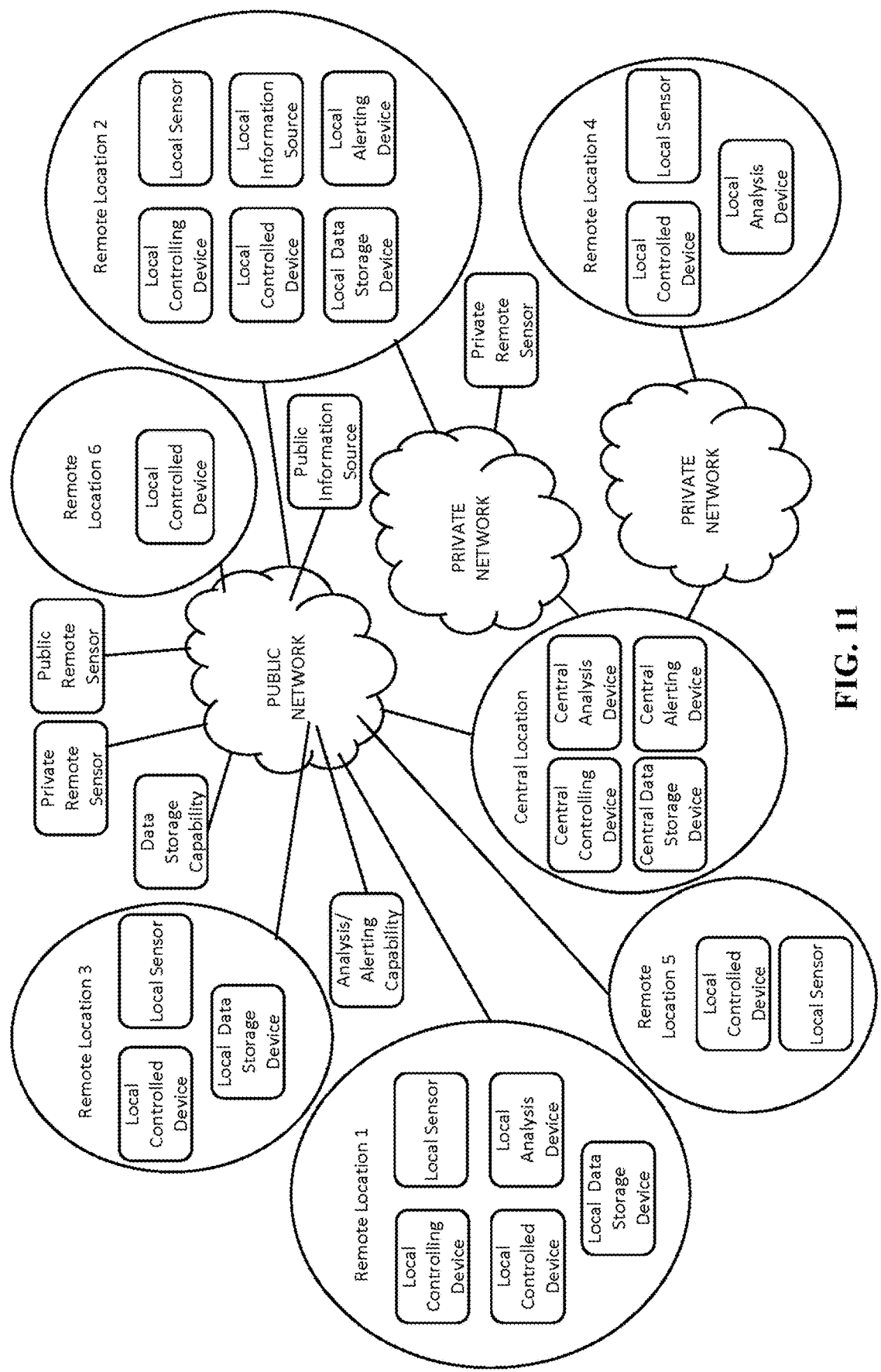
FIG. 11 illustrates a schematic drawing of a habitable environment enhancement system having a plurality of sub-spaces according to one illustrated embodiment.

Now referring to FIG. 11, in some embodiments, a space or sub-space (referred to as a remote location in FIG. 11) may include or have access to a system or one or more analysis or other devices (e.g., computers) for determining, assessing and setting environmental characteristics or scene of a space or sub-space and/or for determining, assessing and setting a path to change a current environmental state or scene within the space or sub-space to a desired environmental state or scene within the space or sub-space. A space or sub-space may be or be part of a habitable environment 100 or other habitable, usable or occupiable area, or include one or more devices, features, apparatus and articles described above regarding the habitable environment 100. For example, a space or sub-space may have a computer and/or other device for analyzing the current environmental conditions of a space or sub-space, and for controlling the environmental conditions or scenes. In some embodiments, some or all of the control system 200 may be used. By one approach, the system includes controllable devices or other devices in the space or sub-space that are configured to change the environmental conditions within the space or sub-space and devices that may receive inputs from one or more transducer devices internal or external to the space or sub-space and inputs from one or more users, among others. As another example, such a space or sub-space may include one or more controllable devices such as systems or devices to turn on, turn off, reposition, reprogram, reset, actuate, recalibrate, or otherwise change the one or more settings for lights, lighting systems, light sources, light suppressors, light generators, window blind position controllers, scent emitters or aroma dispensers, noise generators or suppressors, sound sources, water handling systems, air handling or control systems, air purifiers or filters, air flow control systems, flooring feature controllers, door position controllers, window position controllers, air conditioning systems, heating systems, transducer devices, input devices, humidifiers, dehumidifiers, vent controllers, dynamic custom coloring system, vents, dampeners, valves, etc. for controlling, transitioning, changing, or at least impacting or influencing how a user interacts with a scene, space or sub-space, or the environmental conditions or a scene within the space or sub-space and/or transitioning the environmental conditions within the space or sub-space to a desired state or scene and/or away from a current state or scene. Such controllable devices may include one or more of the artificial luminaires 142, illumination subsystem 204, electrochromatic panes 146, electric motors 152, vents 158, water treatment system 206, UV illumination source 260, humidifier/dehumidifier 271, sanitizing system 216, scent subsystem 210, blowers 275 or 287, heaters 269 or 276, sound subsystem 212, electrostatic filters 266, carbon air filter 249, fans or blowers 272, air treatment system 208, etc.

In some embodiments, an analysis device may be part of a controllable device, controlling device, information storage device (e.g., storage device 246), transducer device, and/or other device integrated along with a controllable device, controlling device, information storage device, and/or transducer device into a single or other device.

In some embodiments, the space or sub-space also may include one or more internal or external controlling devices (e.g., computer) that may connect to or be in communication with one or more controllable devices. Different spaces or sub-spaces may have different systems, environmental control or setting capabilities, different configuration or reconfiguration capabilities, power needs, features, etc. A space or sub-space may or may not be connected to, connectable to, or in communication with a central system, central location, controlling device, controllable device, input device, and/or any location, system or device. In some embodiments, a controlling device and a controllable device may be part of the same device, may be the same device, may be separate devices, may be located in the same space or sub-space, or may be located in different spaces or sub-spaces.

In some embodiments, a space, sub-space or system may include one or more input devices, such as, for example, a keypad, touch screen, smart phone, tablet, display device, computer, terminal, motion sensor, client side device, personal electronic device, microphone, mobile device, wearable device, watch, clickable device or other device. An input device may or may not be wearable, moveable, moving, stationary, part of another device, fixed in position, shared, sharable, interior to a space or sub-space, external to a space or sub-space, etc. Furthermore, an input device may or may not always be turned on, usable, in communication or communicable with other devices, accessible by user, other device or system, available in space or sub-space, associated or usable with a specific scene, shared or sharable, associated with one or more users, spaces, sub-spaces or systems, wearable, locatable, etc. In some embodiments, one or more input devices may be associated with or available in or to a specific user, scene, space or sub-space or collection or grouping of them. In some embodiments, the same or different input devices, alerting devices, storage devices, controlled devices, controlling devices, transducers, etc. may be associated with, used by, or used with two or more users, scenes, spaces or sub-spaces. Input devices may include or be part of devices, controls, panels, mobile or handheld devices, or kiosks 182 or television 184, input/output system 214, etc.

Scenes may be implemented in a space or sub-space based on user data from the input devices and/or environmental readings from sensors or other transducer devices in the space or sub-space. A scene is a combination of parameters implemented by the various systems and subsystems described above. For example, a scene could be a certain combination of air temperature, lighting effects, and ambient noise. By one approach, a scene may include programmed environment parameter settings governing a space or sub-space in a structure that may be used at particular times of day or for particular activities. Illustrative examples of scenes are described in greater detail below.

In some embodiments, a scene is implemented based on the wellness needs or wellness assessments of the user as described above. For example, if the user indicates through an input device that they are drowsy, the space or subspace can implement an energizing scene by decreasing the temperature, brightening the lights, and/or increasing oxygen levels. Energizing scenes are described in greater detail below. In an alternative example, when wearable sensors detect readings suggesting the user is stressed (e.g., elevated heartrate, increased blood pressure, increased temperature), the space or subspace implements a relaxation scene by dimming the lights or changing the lights to a soothing color and/or playing soothing sounds.

In some embodiments, a scene is implemented based on preprogrammed user preferences or needs. For example, a user can program a custom relaxation scene to play every day at the time they finish work. In another example, a user can customize some of the standard scenes described below (e.g., energize, ready for sleep, etc.) to better fit their personal preferences or needs.

In some embodiments, a scene is implemented based on usage occasions or other external factors. For example, if a usage occasion arises in which a large number of people are detected entering a space or subspace, a scene can be implemented in which the temperature and humidity are decreased and sound masking is increased to compensate for the crowd. If certain external factors, such as rapidly increasing external temperature and humidity, are detected a scene can be implemented to decrease the internal temperature, close blinds, reduce or change window transparency, decrease internal humidity, etc. in order to preemptively adapt the environment.

Spaces or subspaces can also have background scenes that promote health or wellness that run as a default when an overriding theme is not triggered by a user input, environmental changes, usage occasions, or external factors. One illustrative example is the dynamic scene described below, in which ambient lighting, temperature, and sound vary slightly over time to simulate a more natural, outdoor environment. This dynamic scene could be a background scene for an office space or sub-space that is overridden by a focus scene or energize scene triggered by a user input, or a crowd compensating scene triggered by a usage occasion as described above.

In some embodiments, a system, controlling device, other device, or user may determine, implement, and/or set a transition plan in a space or sub-space from one scene to another. A transition plan may include changing one or more controllable devices simultaneously, sequentially, in an over-lapping manner, etc. Similar a transition plan may change different environmental conditions within a space or sub-space an identical, similar or different transition rates based on need, user preferences, user history, scene use history, controllable device capabilities, configurations or locations, overall power needs or power availability for the space or sub-space, over power needs or power availability for one or more controlled devices that might implement the scenes or be involved in the transition from one scene to another scene, configuration, condition or design of a space or sub-space, needs or goals of a user, usage occasion, etc. For example, if a user has a limited period of time, if there are influencing external factors (e.g., excessive or unusual heat, humidity, sunlight, or air pollution), etc., the system may shorten or change the transition time or plan from one scene to another scene for one or more controlled devices for a space or sub-space. In some embodiments, a user may select, influence or indicate a desired transition time or plan from one scene to another scene for a space or sub-space.

In some embodiments, configuration or design of a space may contribute to how a scene is designed, implemented, changed, and set, among other factors. For example, a space's or sub-space's lighting design (e.g., number, installation, location, of photometrics of light bulbs and fixtures), fenestration design (e.g., number, size, location and layout of windows), interior design (e.g., interior wall color, ceiling color, floor color, furniture color, furniture layout, building materials), floor design, layout, and quality, the orientation of the space or sub-space, shade or blind design (e.g., optional positions, thickness, sound and temperature insulation, and transparency), door design (positions, thickness, sound and temperature insulation, and transparency), among other elements, may impact how a scene is established in a space or sub-space. These factors also may impact the effectiveness of the scene, how a transition to the scene or away from the scene in the space or sub-space is planned or conducted, how a user may react or benefit from a scene implemented in the space or sub-space, and how a default setting for the scene may be set or implemented for the space or sub-space, among others.

In some embodiments a system, controlling device, space or sub-space may include or have access to one or more internal or external transducer devices to determine the conditions or features within the space or sub-space, the availability, operating state and functionality of any controllable device or controlling device, the current state of multiple spaces or sub-spaces, the current scene operating within a space or sub-space, the number of users in a space or sub-space, the current state or desire of a user, the location of a user, etc. In some embodiments, transducer devices may include one or more sensors for measuring light intensity, light color temperature, light distribution, light source location or direction, illuminance, air temperature, air temperature distribution, air pressure, air quality, air movement, air flow source location or direction, air purity, water quality, humidity, sound level, sound distribution, sound source, sound quality, smell or aroma, aroma distribution, occupant number, occupant presence, occupant movement, occupant physical state, occupant clothing color, occupant position within space or sub-space, occupant attribute, orientation, design, shape, presence, color or position of furniture, decorations, ceilings, walls, floors and other features, equipment or materials in a space or sub-space, one or more specific environmental conditions or attributes, amount, presence or absence of one or more chemicals, gases (e.g., carbon monoxide, carbon dioxide), pollutants, pathogens, smoke, micro-organisms, volatile organic compounds (VOCs) or other specific or non-expected materials, operation and location of one or more controllable devices, power use of one or more controllable devices, current scene operating or established in space or sub-space, transition progress from one scene to another scene in a space or sub-space, variation from an scene operating in a space or sub-space, etc. In some embodiments, transducer devices may be or include occupant sensors or detectors 280, temperature sensors or detectors 281, humidity sensors or detectors 282, etc.

In some embodiments, one or more of transducer devices may be wearable by one or more users, immobile or in a fixed position within the space or sub-space, moveable or moving within the space or sub-space, etc. Different transducer devices may be used or available in different spaces or sub-spaces, with different scenes or users, with different controllable devices or other devices, etc.

In some embodiments, the transducer devices may provide or help provide one or more inputs to a system or one or more devices in the system, to a space or sub-space, etc. For example, such inputs may include one or more of the inputs described in the table below or one or more other inputs.

TABLE 1

| | INPUTS |
|---|---|
| User State | Actual, expected, perceived or believed mental condition |
| | Actual, expected, perceived or believed physical condition (e.g., age, health, gender, weight, body mass index, height) |
| | Actual, expected, perceived or believed state of wellness or well-being |
| User Goal | Pre-event preparation (e.g., upcoming travel, new work schedule, stress event upcoming, change of schedule or routine, change of daily habit) |
| | Post event recovery (e.g., jet lag, sleep deprivation, stressful work, climate change, need to relax, need to energize) |
| | Acclimation to new space or sub-space or other habitable environment |
| | Acclimate to change in current space or sub-space or other habitable environment |
| | Acclimate to external environmental condition |
| | Acclimate to new daily routine or schedule |
| | Desired scene or scene change |
| | Transition from one scene to another |
| Usage Occasion | User in ship, train, bus, apartment, camper, plane, hotel, home, trailer, office, school, restaurant, or other space or sub-space |
| | User in familiar space or sub-space or other habitable environment |
| | User in unfamiliar space or sub-space or other habitable environment |
| | User as part of group |
| | User alone |
| | User going to a specific space or sub-space or other habitable environment |
| | User allotted or available time for a scene or scene change |
| | User allotted or available time in a space or sub-space or other habitable environment |
| | User in situation requiring some sort of alert |
| | User in non-optimal or desired physical state |
| | User in non-optimal or desired mental state |
| | User suffers an injury, fall or medical condition |
| | User desiring a specific scene or environmental conditions in a space or sub-space or other habitable environment that the user is in |
| | User desiring a specific scene or environmental conditions in a space or sub-space or other habitable environment that the user is not in |
| | User needing a specific scene or environment conditions in a space or sub-space or other habitable environment that the user is in |
| | User needing a specific scene or environment conditions in a space or sub- |

TABLE 1-continued

INPUTS

| | |
|---|---|
| | space or other habitable environment that the user is not in |
| | User desires a specific scene, a change to a scene, a scene to start or end, a transition from one scene to another |
| | User wants to continue or enhance a scene |
| Technical Capabilities and Availability | Of sensor or other transducer device |
| | Of controlled device |
| | Of controlling device |
| | Of network |
| | Of analysis tools/device |
| | Of alerting device |
| | Of system |
| | Of space or sub-space or other habitable environment |
| | Of space or sub-space feature or component |
| | Of information storage device |
| | Of input device |
| | Of output device |
| | Of device associated with a user, space, sub-space, other habitable environment or system |
| | Of system |
| Potential uncontrollable factors | Climate |
| | Time |
| | Available time |
| | Season |
| | Date |
| | Day of week |
| | Month of year |
| Configuration | Location of sensor or other transducer device, controlled device, controlling device, space or space feature, sub-space or sub-space feature, analysis device, system, etc. |
| | Design, capability or configuration of controlled device, controlling device, transducer device, space feature, sub-space feature, alerting device, analysis device, system, etc. |
| | Of space, sub-space, other habitable environment, input device, controlled device, transducer device, controlling device, analysis device, system, information storage device, etc. |
| Signals, information or data | From analysis device, sensor or other transducer device, data storage device, information source, controlled device, controlling device, storage device, etc. |

In some embodiments, the space or sub-space may include one or more alerting devices to indicate that an environmental condition within the space or sub-space does not meet required or desired limits. For example, a visual or audible alarm may be triggered if the humidity, air quality, temperature, etc. within a space or sub-space exceeds or is out of range of requirements or desired limits.

In some embodiments, the system has a baseline or a background scene that is configured to optimize a baseline condition for health and wellness in a space that may be used throughout the day or during one or more different periods of time during the day, unless the user prompts the system for a particular scene or a "user goal" that is specific, such as, for example, energize, focus, or relax, among others, or another input, analysis result, usage occasion, default setting, etc. requires or establishes a different scene.

In some embodiments, a system also may include or have access to one or more private network based, public network based, cloud based, local area network based, World Wide Web-based, Internet-based or other data/information storage or information source devices for storing, collecting, providing and/or analyzing: (1) information related to one or more former, current or expected occupants or other users of the space or sub-space (e.g., age, weight, height, body mass index, allergies, biometrics, biomarkers, environmental condition or setting preferences, prior or current health or medical condition, recent exercise or other physical activity, exercise schedule, recent food intake, current or prior diet, medical history, current or previous prescriptions, occupation, occupational history, hobbies, education, area of residence, current or prior location, family medical history, recent sleep schedule, gender, scene default preferences or changes, recent travel schedule, goals, usage occasions, scene preferences, scene changes, location, recent or current activity, nationality, race, ethnicity, blood cholesterol level, social status, marital status, relationship status, family members); (2) information regarding one or more input, controllable or controlling devices in the space or sub-space or external to the space or sub-space such as the capability, performance range, transition capabilities, current or potential operational state, location, features, design, power use, power needs, reliability, durability, etc. of a controlling or controllable device; (3) information regarding one or more transducer devices in the space or sub-space or external to the space or sub-space (e.g., setting, capability, operation state, sensor type, sensitivity, configuration, configuration options, features, operating limits, reliability, durability, power use, power needs, condition, location, etc.); (4) algorithms or other information for setting, determining or analyzing environmental or other conditions within the space or sub-space; (5) information related to conditions or environmental parameters (e.g., temperature, air pressure, humidity, lighting, sunshine, radiation levels, oxygen, wind, altitude, location, air quality, radon exposure or levels, pollen count, smell, smell distribution, noise level, source, distribution or content, presence of pollutants or pollution level, crowd density, traffic density, arsenic levels, ozone level, presence of volatile organic compounds (VOCs), presence of other gases, particulates or materials) external to the space or sub-space, (6) information related to the use, configuration, operation, design, occupancy, environmental conditions, adjustable features, capabilities, location, intended use, current use, potential use, condition, wellness score, wellness assessment, available devices or equipment, color, furniture design and location, etc., of or in a space or sub-space; (7) information regarding one or more information sources within a space or sub-space or external to the space or sub-space; (8) information regarding one or more alerting devices within a space or sub-space or external to the space or sub-space (e.g., setting, capability, operation state, configuration, age, features, operating limits, reliability, durability, power use, power needs, condition, location, etc.); and/or (9) information regarding one or more pre-set or default scenes which may be settable, resettable, changeable or configurable within the space or sub-space using one or more of the controlling and/or controllable devices. The system, space or sub-space also may include or have access to one or more analysis devices to process, evaluate, collect, make decisions based on, share or provide, etc. this or other information.

In some embodiments, a scene may be adjustable automatically, by request or on an ad-hoc basis by a user, a system or device within the space or sub-space, one or more users, a system or device external to or remote from the space or sub-space, etc.

In some embodiments, a scene may be triggered or set for only one sub-space within a bigger space such as a bedroom, home office or kitchen within a home, a single apartment within an apartment complex, a single classroom within a school, a single meeting room within an office, a single patient room at a hospital, a single dining room within a home, a single room at a hotel, a single cabin on a cruise ship, etc. Alternatively, a scene may be triggered across multiple sub-spaces within a space, such as a home office and a dining room within an apartment, a bedroom and a living room within a single family home, a bathroom and a bedroom within a hotel suite, multiple apartments within an apartment complex, multiple classrooms within a school, multiple offices within a broader work location, multiple cabins on a ship, multiple meeting or conference rooms within a work environment, multiple recovery rooms within a hospital, multiple reception areas within a hospital, etc.

In some embodiments, a system or one or more devices within a space or sub-space may be connected or in communication physically or wirelessly via a private network, public network, the Internet or World Wide Web, a wireless network, secured or unsecured network, hard-wired network, Bluetooth communication, cellular communication, radio communication, line-of-sight communication, etc. Different devices, systems, locations, spaces or sub-spaces also may be in communication with each other in multiple or different ways.

In some embodiments, a user or system may desire to create environmental conditions or scenes within a space or sub-space that promotes or encourages healthy behavior, aligns with a usage occasion or goal of the user, builds healthy habits and/or provides feedback to one or more users to change behavior or alter environmental conditions with a space or sub-space to improve user health. In some embodiments, a scene may be operating constantly, during a majority of time, at designated times or intervals, for a specific length of time, upon selection by a user or system, etc. For example, a scene may establish environmental conditions within a space or sub-space to help a user regulate the user's circadian rhythm and to improve thermal comfort and air quality within the space or sub-space. Such a scene may be operating continuously or at regular intervals unless altered by the system or user, interrupted by another scene set by the system or selected by a user, etc. In some embodiments, scene settings, launch time and/or duration time may vary by date, day of week, month of year, time of day, season, external weather conditions, user preferences, user needs, user goals, usage occasion, type of space or sub-space, configuration or features of a space or sub-space, intended use of a space or sub-space, number of occupants in a space or sub-space, controllable devices available for a space or sub-space, or other factor.

In some embodiments, a scene may be operating constantly, during a majority of time, at designated times or intervals, for a specific length of time, upon selection by a user or system, etc. For example, a scene may establish environmental conditions within a space or sub-space to help a user regulate the user's circadian rhythm and to improve thermal comfort and air quality within the space or sub-space. Such scene may be operating continuously or at regular intervals unless altered by the system or user, interrupted by another scene set by the system or selected by a user, etc.

In some embodiments, scenes operate in response to measuring some prerequisite event or events. For example, if the wearable device detects that the user has just exercised by measuring an increased heart rate, and tracking a change in location indicating a run a post workout scene is triggered. The scene turns on the television to a fitness channel demonstrating stretches, a screen in the kitchen displays instructions on how to prepare an appropriate post workout meal, and a prompt is sent to the user instructing them to rehydrate and indicating an appropriate amount of water. The system can also estimate the amount of calories burned and the expected results based on stored weight and BMI measurements.

In some embodiments, one or more scenes may be operating simultaneously within a space or sub-space. For example, a relaxation directed scene may be operating in a bedroom within a house or apartment while a focus directed scene may be operating in an office within the house and a circadian rhythm setting scene is operating in one or more other sub-spaces within the house.

Every individual is different and different groups of users, or groups of users occupying a space or sub-space also is unique. As a result, the specific scenes for a specific user state can differ from one user to another user. Similarly, specific scenes for specific groups of users may vary from one group to another group. Therefore, in some embodiments, a system, analysis device, controlling device, and/or one or more controllable devices may constantly or at regular intervals (e.g., every half second, second, five seconds, thirty seconds, minute, five minutes, ten minutes, thirty minutes, hour, two hours, five hours, day, or other time intervals) takes, receives or otherwise obtains information regarding the environment for a space or sub-space and biometric or other information for a specific user (e.g., age, health condition, travel history, location, sleep history, current physical state) to recommend, change or set one or more scenes in one or more spaces or sub-spaces to promote frequently occurring user states or goals, to meet user needs, to help address or satisfy relevant user occasions, help the user overcome a bad habit or establish a good habit, etc. For example, a system, controllable device, controlling device or analysis device may recognize or otherwise determine by itself or based on information received from a user, transducer device, analysis device, input device, or other device or system that the specific user travels a lot by taking in or otherwise accessing or obtaining the user's digital calendar data or other schedule information and that the user is not sleeping well. As a result, dynamically the system may recommend or establish a jet lag scene specifically tailored to the user and/or for the space or sub-space that the user is in or will be in. The dynamically created scene also may have one or more settings that vary depending on the type, number, location, etc. of one or more controllable devices or transducer devices in the space or sub-space. In another example, the system may recognize or otherwise determine that the user always drinks coffee at 3:00 PM. Therefore, the user is prompted to have the energize scene always turn on at 3:00 PM for a defined amount of time to help wake the user up or stay alert. The amount of time may be determined by or based on the user, the system, the type of space or sub-space, features in the space or subs-space, other internal or external environmental factors, etc. which may hinder or aid the user in waking up or staying alert. If the user is in a larger group setting, the scene may be set or established or directed locally to the user (e.g., at the user's desk) as opposed to an entire space or sub-space so as to reduce impact of the energize scene on other users in the space or sub-space, impact on another scene that may be established in the space or sub-space, etc. As another example, a system may establish a specific default or other scene in a space or sub-space based on a specific user's regular occupation of such space or sub-space at a specific time each day (e.g., a user returning home at 5:30 PM each day). Based on information received from or about a user or other information regarding the current environmental conditions within the space or sub-space (e.g., a specific light fixture is broken, a specific odor is present, other occupants are present, temperature is cooler than normal) or external to the space or sub-space (e.g., outside air temperature is hotter than normal, humidity level is higher than normal, rain is present, change in sunset time, cloudy conditions), the system or device may change the default or other scene implemented within the space or sub-space at the specific time to better accommodate the user, to facilitate the completion of the rationale or reasoning behind the original scene, to establish the end environmental conditions desired in the space or sub-space more quickly given the other factors, to overcome conditions that may inhibit performance or implementation of the original scene, etc.

A dynamically established or implemented scene may vary in one or more environmental parameters from a default scene for the same user, for another user, for a group of users, etc., even if the dynamically established or implemented scene is being used or implemented for same general purpose of the default scene or is otherwise similar to the default scene. For example, transitions within or for a dynamically created scene for one or more environmental parameters (e.g., lighting, air temperature, background noise or aroma) may occur at different rates than in the default scene. As another example, light color temperature or light intensity within a dynamically controlled scene may be set or transitioned to or away from differently within the dynamically created scene than other similar scenes.

A breakdown of several illustrative scenes are provided in table 2 below.

TABLE 2

| | | User Initiated Scenes | |
|---|---|---|---|
| Scene | Relevant Room | Parameters and Definition | Rationale |
| Circadian | ALL ROOMS: Bedroom Bathroom Living Room Kitchen Office | Lighting CCT: CCT will be set to 2300-2500 K during the evening since studies using lights with a CCT of 2300-2500 K have demonstrated to have minimal effects on sleep, alertness, and glare. The CCT will increase gradually through astronomical, nautical and civil twilights, reaching a peak of 6500 K where it will remain until the onset of sunset (entering civil twilight again), when it will reverse the process, reducing to 2300-2500 K by nightfall. A table of local sunset times will be included in the programming. Intensity: Lighting intensity will be 100% during the day and maintained at about 5% at night in order to achieve these illuminance levels at eye-height (as indicated before, the actual illuminance levels depend on a number of factors of lighting design, interior design, etc.). A table of local sunset times will be included in the programming. EML: For proper alignment of the circadian system to the normal day, it is essential that there is a contrast between the EML during the day and during the night, with a greater EML throughout the day and lower at night. Blackout Shades The blackout shades will open 1.5 | The purpose of the Circadian Setting for the bedroom is to act as a default scene in order to create ambiance that may help residents maintain a healthy and robust circadian rhythm through specific settings of lighting and blackout shades systems throughout the entire day. |

TABLE 2-continued

User Initiated Scenes

| Scene | Relevant Room | Parameters and Definition | Rationale |
|---|---|---|---|
| | | hour before sunrise and close 1.5 hours after sunset. Shades can be automatically opened if the dawn simulation scene is active, closed during the ready for sleep scene, or can be opened/closed by residents manually. If shades are open, they will automatically close 1.5 hours after sunset. A table of sunrise/sunset times specific to location can be included in the programming. | |
| Energize | Bedroom Bathroom Office | Lighting CCT: 6500 K Intensity: 100% intensity Blackout Out Shades The blackout shade position is controlled by the local sunset time. During daytime before sunset, to maximize the daylight in the bedroom for the energizing scene, the shade is recommended to be set at fully open. At 1.5 hours after sunset, in order to protect the residents' privacy, the blackout shades are recommended to be set at fully closed. Temperature Indoor temperature between 20° C. and 22° C. is found to have positive impact on occupant alertness and performance. Given that the temperature set-point throughout the day and night depends on individual thermal comfort preference, cultural differences, energy considerations, activities, clothing insulation, and many other factors, the temperature value for the Energizing Scene is set to be 2° C. lower than the temperature setting prior to switching on the Energizing Scene | The purpose of the Energizing Scene in the bedroom is to create ambiance that may help the residents feel more energized through lighting, shades, and HVAC system settings at daytime or nighttime. |
| Relax | ALL ROOMS: Bedroom Bathroom Living Room Kitchen Office | Lighting CCT: 2700 K Intensity: 50% intensity Blackout Out Shades The blackout shade position is recommended to be fully closed to protect the residents' privacy. Temperature Given that the temperature set-point throughout the day and night depends on individual thermal comfort preference, cultural differences, energy considerations, activities, clothing insulation, and many other factors, the temperature set-point is set to be 2° C. warmer of its current setting. | The purpose of the relax scene in the bedroom is to create ambiance that may help the residents feel more relaxed through lighting, shades, and HVAC system settings at daytime or nighttime. |
| Play | Bedroom Living Room | Lighting Intensity: 100%, with the ability to adjust via smartphone app. Dynamic colors can be used for the play scene. Time intervals for transitioning can be adjusted (from 1 second to 60 seconds) through a smartphone app. The default transition time is 3 seconds. The residents also may be able to pick a specific color for the entire time through their smartphone app. | The purpose of the play scene in the bedroom is to create exciting and colorful ambiance. |

TABLE 2-continued

User Initiated Scenes

| Scene | Relevant Room | Parameters and Definition | Rationale |
|---|---|---|---|
| | | Rainbow mode: full color light cycles through red colors at the beginning to pink/purple colors at the end; Random mode: use a random algorithm (e.g., Monte Carlo) to select a color from the entire table and cycle through different random colors; Manual mode: the color space is shown on the smartphone app, and the occupant can pick any color manually through the app. Blackout Shades The blackout shade position will be fully closed to protect residents' privacy. The residents will have the ability to raise the shades if they want to. Temperature The play scene is designed for entertainment-related physical activities, which may increase occupants' metabolic rate. Given that the temperature setpoint throughout the day and night depends on individual thermal comfort preference, culture difference, energy considerations, activities, clothing insulation, and many other factors, the air temperature setpoint is set to be 2° C. lower compared to its current setting. | |
| Dawn Simulation | Bedroom ** Could be other rooms if wanted | Lighting EML, CCT, Intensity Gradually increasing light intensity and color temperature during sunrise is the sun's natural pattern seen in nature. Illuminance levels increasing from 0 to 250-300 lux have been found to have an effect on improving cognitive performance; earlier awakening, feeling more alert at awakening, getting up easier and having higher alertness at $2^{nd}$ lesson at school in children and adolescents; improved alerting effect in adolescents; significantly gradient reduction in heart rate during the transition from sleep to wakefulness; improved perceived sleep quality, greater alertness, improved cognitive and physical performance after waking; improved subjective well-being, tension and mood, and improved cognitive performance; significant reduction in sleep inertia severity complaints and improved subjective well-being; significantly lower levels of sleepiness and greater levels of subjective activity; greater arousal (reporting being more alert and less tired); improved subjective sleep quality; and improved quality of awakening. Blackout Out Shades The blinds preferably do not go up earlier than at the end of the 30-minute dawn simulation period because if the light levels outside are greater than those provided by | The Dawn Simulation Scene provides a carefully coordinated schedule of six parameters melanopic lux (m-lux), illuminance (lux), correlated color temperature (CCT), environmental temperature (° C.), sound intensity (dBA), and blackout shade movement— to ensure an improved waking up experience and circadian entrainment over time. |

TABLE 2-continued

User Initiated Scenes

| Scene | Relevant Room | Parameters and Definition | Rationale |
|---|---|---|---|
| | | the dawn simulator at that time, then the lighting schedule would get thrown off track. In some embodiments there may be two or more layers of shades so that when a blackout shade rises, there is still a shade in front of the window that lets some light in but provides privacy for the user or in the space or sub-space. Electrochromatic glass also may be used to provide the benefits or impacts of shades or blinds and visible light transmittance (VLT) value may of such glass may increase over time during dawn simulation scene.<br>Temperature<br>The specific temperature values, or the starting value selected in the evening from which the temperature will start to drop until sunrise and then increase after sunrise may be chosen by the resident. However, the falling/increasing range will be defined, e.g., a drop in 3° C. then an increase in 3° C.. The ranges may be informed by/consider the average drop in nighttime temperature and increase after sunrise at a given time of year, in the geographical area where the residents live; however, the temperature ranges in the home do not need to be as extreme/uncomfortable as they are in nature.<br>Sound<br>The dawn simulator sound could vary between 20 and around 50-55 dBA, with the highest levels occurring during the time after the highest lighting intensity has been reached. The goal is to awaken with increasing light levels, and ultimately circadian entrainment, not to be awoken by greater sound levels; sound is a component of the experience, but is not intended to act as an alarm to ensure awakening. The sound is increased over the final few minutes (e.g., 4 minutes) of the dawn simulation, and the sound continues to play at the loudest level (50-55 dBA) until disabled by the user. | |
| Ready for Sleep | Bedroom | Lighting<br>After the scene is activated, the fully color-tunable LED downlights are programmed to provide a CCT and light intensity that gradually transitions from the current setting to 2500K and 10%, respectively, over 15-60 minutes, depending on the user's choice (15, 30, 45, 60 minutes), then reducing the intensity to 0% 5 seconds after the set time has elapsed.<br>Blackout Out Shades<br>The blackout shades are programmed to stay fully closed.<br>Temperature<br>Since thermal comfort is highly individual, depending on | The purpose of the Ready for Sleep scene in the bedroom is to create a transitional ambiance to prepare the residents for sleep through lighting, shades, and HVAC system settings at nighttime. |

TABLE 2-continued

User Initiated Scenes

| Scene | Relevant Room | Parameters and Definition | Rationale |
|---|---|---|---|
| | | insulation layers, and individual and cultural differences, we are recommending relative changes in temperature, dependent upon what the occupants set as their optimal temperature on the in-built thermostat. A 2° C.-3° C. change in temperature over a 30 minute-3-hour period starting at sunset time has been shown to have significant effects on sleep onset and waking. | |
| Night Light | Bedroom | Illuminance<br>Illuminance below 15 lux (at corneal level in the horizontal angle of gaze) has been found to evoke minimal melatonin phase shift. However, given the dark adapted state of the retina, the intention to not wake up a partner who may also be sleeping in the bedroom, and to minimize melatonin suppression and circadian disruption, the illuminance of night lights may be even lower—at or below 5 lux, as measured at corneal level in the horizontal angle of gaze.<br>CCT<br>The recommended CCT is 2300 K or lower, based on a study that found no effect of melatonin secretion with exposure to light of 2300 K, 200 lux (at eye level) for 1.5 hours at midnight, whereas melatonin secretion was measurably suppressed at 3000 K and acutely suppressed at 5000 K.<br>Light Wavelength<br>The various types of light that make up the electromagnetic spectrum differ in wavelength. The human circadian system is particularly sensitive to short wavelength light in the blue spectrum, with peak circadian sensitivity at 470-490 nm. At the wavelength of 555 nm and greater, the relative sensitivity to melatonin suppression drops significantly. Therefore, the majority of the spectral power of the night lights may be greater than 555 nm, which still significantly stimulates the image formation necessary to safely navigate to the bathroom, while minimizing the proportion of 480 nm band of the spectrum. | The purpose of the Night Light scene in the bedroom is to provide minimum lighting for residents to safely get up and navigate the room at night with reduced disruption to their circadian rhythm. |

EXAMPLES

A number of scenes are described in detail below. These are only intended as illustrative examples. Many scenes not described below can be implemented based on the teachings of the present disclosure. Similarly, the scenes below can be altered and still achieve the desired effect.

Example 1: Circadian Scene

Everyone experiences natural fluctuations in alertness and fatigue or sleepiness on a daily basis. Alertness tends to be lowest in the early morning and in the evening before sleep, also slumping in the mid- to late-afternoon. These patterns are highly associated with the periodicity of the circadian rhythm. Multiple bodily processes, including sleep and digestion are regulated in part by a central circadian clock that is located in an area of the brain called the hypothalamus. The time of the circadian clock is set by the timing of light exposure, which it receives via specialized cells in the eye, called intrinsically photosensitive retinal ganglion cells or ipRGCs. Daily, regularly-timed light exposure is required to maintain a healthy and robust circadian rhythm; this process is called "entrainment". Many aspects of light exposure determine the effectiveness of the exposure, including its timing, intensity, wavelength composition (color), and duration. In general, light in the evening and early night will delay (i.e., events will be timed to occur later the next day) the circadian rhythm, while light in the morning advances it earlier in the day (i.e., events will be timed to occur earlier the next day). Standard electric sources of "white light" can vary significantly in terms of the circadian impact due to different spectral power distributions.

Besides its role in aligning our internal biological clock, light can also evoke an acute and immediate change on subjective and objective measures of alertness, including psychomotor vigilance tests (PVT, a simple sustained attention task) and electroencephalography (EEG). The purpose of the Circadian Setting for the bedroom is to act as a default scene in order to create ambiance that may help residents maintain a healthy and robust circadian rhythm through specific settings of lighting and blackout shades systems throughout the entire day.

The energizing scene is the first and default control scene in the bedroom that can be activated by both the keypad and the smart phone app. After the scene is activated, the fully color-tunable LED downlights are programmed to provide certain intensity and correlated color temperature (CCT) based on local sunrise and sunset times, which vary based on longitude and latitude as well as time of the year. The blackout shades automatically close 1.5 hours after sunset time and open 1.5 hour after sunrise. They can also be automatically opened using the dawn simulation scene or manually by the residents. Sigmoid functions are implemented in the transition periods to minimize the noticeable change among different parameters.

Below are a number of parameter settings, such as equivalent melanopic lux (EML), sunrise and sunset times, intensity, CCT, blackout shades, and temperature, used for a circadian scene. Illuminance is the amount of light reaching a surface area from a light source and is commonly measured in either lux or foot candles (unit: lux or foot candle; 1 lux=1 lumen/m2, 1 fc=1 lumen/ft2). The lux unit, furthermore, is normalized to the color sensitivity of a standard observer at 1 m, with a peak sensitivity at ~550 nm (green), representing the accumulated activity of the three cone system in the foveal region of the eye (short-, middle-, and long-wavelength sensitive, or the blue, green, and red cones). Thus, the lux unit is useful in describing the amount of light that will be perceived by conscious high acuity, image-forming vision. The circadian system, however, relies on a combination of the three cone system and a system that is intrinsic to the ipRGCs—the melanopsin system. Unlike the three cone system used for image-formation, melanopsin is mostly sensitive to short (blue, ~490 nm) wavelengths of light. A new unit, the melanopic lux (also referred to as melanopic illuminance) has been proposed as the amount of light that enters our eye affecting the melanopsin pigment in ipRGCs, taken as a multiple of photopic lux (RGB) and a given melanopic ratio. For proper alignment of the circadian system to the normal day, it is essential that there is a contrast between the EML during the day and during the night, with a greater EML throughout the day and lower at night. The greater the daytime light exposure, the higher the night time light exposure can be without deleterious effects on the circadian system.

The overall illuminance and EML at eye level are dependent on the building's lighting design (e.g., number, installation, and photometrics of light fixtures, etc.), fenestration design (e.g., number, size, layout of windows), interior design (e.g., interior wall color, ceiling color, floor color, furniture color, furniture layout), the orientation of the room, shade positions, and other factors that reflect light. The melanopic ratio is a function of light type and CCT, however, CCT and intensity setting of electric lighting are only some of the parameters that can be influenced by the building control system; all other factors also may also be considered (simulated or measured).

The US Naval Observatory (USNO) uses the definition of sunrise and sunset as the point at which the upper edge of the sun's disc is on the horizon. Civil twilight is a period of time immediately before sunrise and after sunset until the center of the sun is geometrically 6 degrees below the horizon; nearly all objects can still be clearly seen during this period. Nautical twilight refers to a time frame when the center of the sun is 6-12 degrees below the horizon; object shapes and the horizon itself are still visible (named for mariners using the horizon for navigation). Finally, astronomical twilight is when the center of the sun is positioned 12-18 degrees below the horizon, before complete darkness (on a moonless night); illumination is mostly indistinguishable.

Exposure to bright light during the day is significantly correlated with improved 'sleep quality' and lower 'fatigue', when controlling for gender, age, eye correction, seasonal sensitivity and chronotype (i.e., morningness or eveningness of an individual). Daytime exposure to bright light (>1000 lux), as compared to dim light (5 lux), decreases sleepiness and improves sustained attention. Hence, lighting intensity will be 100% during the day and maintained at about 5% at night in order to achieve these illuminance levels at eye-height (as indicated before, the actual illuminance levels depend on a number of factors of lighting design, interior design, etc.). A table of local sunset times will be included in the programming.

A field measurement will typically be conducted to correlate different light intensity levels with illuminance levels in regularly occupied areas in order to meet the requirements.

In one approach, a circadian scene has a CCT set to 2300-2500K during the evening since studies using lights with a CCT of 2300-2500K have demonstrated to have minimal effects on sleep, alertness, and glare. The CCT will increase gradually through astronomical, nautical and civil twilights, reaching a peak of 6500K where it will remain until the onset of sunset (entering civil twilight again), when it will reverse the process, reducing to 2300-2500K by nightfall. A table of local sunset times will be included in the programming.

Although CCT is a widely used parameter in the lighting industry for setting up the system, a certain CCT is not directly correlated with a type of spectral power distribution (SPD), which correlates to the actual EML values. In other words, a particular CCT value can have numerous types of SPD, which may result in different EML values, and therefore may have different circadian effects on the residents.

During the circadian setting, the blackout shades will open 1.5 hour before sunrise and close 1.5 hours after sunset. Shades can be automatically opened if the dawn simulation scene is active, closed during the ready for sleep scene, or can be opened/closed by residents manually. If shades are open, they will automatically close 1.5 hours after sunset (the maximum nautical and civil twilight in Australia). A table of sunrise/sunset times specific to location will be included in the programming.

Given that the temperature setpoint throughout the day and night depends on individual thermal comfort preferences, cultural differences, energy considerations, activities, clothing insulation, and many other factors, the circadian scene will not alter the temperature setpoint, but will allow other scenes to automatically alter the temperature based on different use cases, and allow to be manually changed by the occupants.

Figure 12:
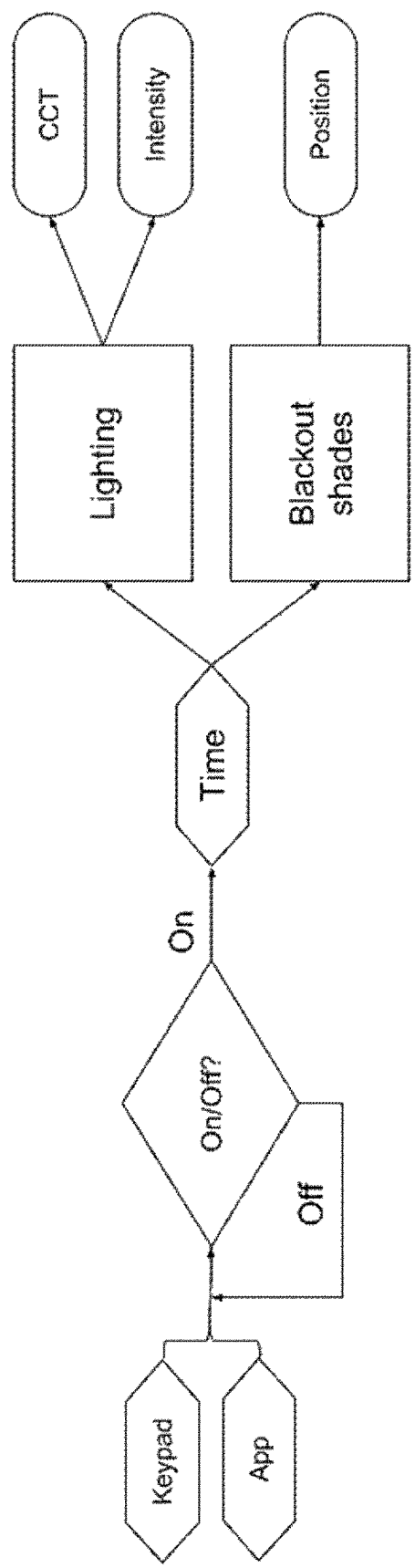
FIG. 12 illustrates a flow diagram showing a sequence of operations of a circadian scene according to an illustrated embodiment of the present invention.

FIG. 12 illustrates the sequence of operations for the circadian scene described above.

Example 2: Energizing Scene

The human body clock runs on a schedule that is naturally about 24 hours and 15-30 minutes long. Unless regularly reset, this 15 to 30-minute discrepancy makes us want to go to sleep later and wake later, relying on alarm clocks in the morning in order to function on a 24-hour day schedule. Bright light is the strongest entraining agent of the human circadian rhythm, and exposure to light in the morning can make waking up easier. Morning use of bright light is known to phase-advance (shifting the sleep phase earlier), whereas evening use is known to phase-delay (shifting the sleep phase later) the circadian rhythm. In order to have sleep and wake patterns that are better aligned with the schedules of work, school or social activities, individuals who are very early risers may want to delay the timing of their sleep, whereas "night owls" may want to advance it. Phase advancing may also be of interest to individuals who are traveling east in order to reduce the symptoms of jet lag, and to shift workers on early morning shifts who want to fall asleep and wake earlier.

There are a variety of psychological factors that determine how "energized" or "awake" an individual feels. Two external factors that influence this internal state are the thermal and lighting environments. It is important to note that thermal perception is related to not only air temperature, but also air velocity, relative humidity, clothing insulation, occupant metabolic rate, and mean radiant temperature of the environment, as defined by ASHRAE thermal comfort model. High indoor illuminance (1000 lux, as compared to the normal 200 lux) at eye level has alertness-enhancing effects (feeling more energetic and less sleepy) during both daytime and nighttime. The relationship between alertness and illuminance can be described as a sigmoid (s-shaped) function with a linear rise, representing increasing effects of light intensity on alertness, in normal room lighting.

The purpose of the Energizing Scene in the bedroom is to create ambiance that may help the residents feel more energized through lighting, shades, and HVAC system settings at daytime or nighttime.

The energizing scene is generally the second control scene in the bedroom that can be activated by both the keypad and the smart phone app. After the energizing scene is activated, the fully color-tunable LED downlights are programmed to provide high correlated color temperature (CCT=6500K) and full intensity (100%). The blackout shades are programmed to stay open during daytime for maximum daylight, but fully closed after sunset for privacy. The thermostat is programmed to provide cooler air temperature by decreasing the current thermostat setting by 2 degrees Celsius.

Below are a number of parameter settings, such as equivalent melanopic lux (EML), intensity, CCT, and temperature, used for an energizing scene. Illuminance is the amount of light reaching a surface area from a light source and is commonly measured in either lux or foot candles (unit: lux or foot candle; 1 lux=1 lumen/m2, 1 fc=1 lumen/ft2). The lux unit, furthermore, is normalized to the color sensitivity of a standard observer at 1 m, with a peak sensitivity at ~550 nm (green), representing the accumulated activity of the three cone system in the foveal region of the eye (short-, middle-, and long-wavelength sensitive, or the blue, green, and red cones). Thus, the lux unit is useful in describing the amount of light that will be perceived by conscious high acuity, image-forming vision. The circadian system, however, relies on a combination of the three cone system and a system that is intrinsic to the ipRGCs—the melanopsin system. Unlike the three cone system used for image-formation, melanopsin is mostly sensitive to short (blue, ~490 nm4) wavelengths of light. A new unit, the melanopic lux (also referred to as melanopic illuminance) has been proposed as the amount of light that enters our eye affecting the melanopsin pigment in ipRGCs, taken as a multiple of photopic lux (RGB) and a given melanopic ratio. For proper alignment of the circadian system to the normal day, it is essential that there is a contrast between the EML during the day and during the night, with a greater EML throughout the day and lower at night. The greater the daytime light exposure, the higher the night time light exposure can be without deleterious effects on the circadian system.

As discussed above, the effects of light on the energized state will be due to an effect that is measured by a combination of lux and melanopic lux. Light has both a direct and indirect effect on mood and emotion. The indirect effect of light would be that mediated by changes in circadian synchronization. A circadian clock that is exposed to regular light patterns will lead to improved mood and energy levels. Individuals with erratic light exposure patterns often express depressive symptoms, which can then lead to a negative cycle in which the depression then leads to increasingly erratic light patterns. Light also has a direct effect on mood and energy levels. This is also mediated by the ipRGC system through the activation of non-circadian circuits in the hypothalamus of the brain. Humans must receive sufficient light exposure to maintain an optimal mood.

The overall illuminance and EML at eye level are dependent on the building's lighting design (e.g., number, installation, and photometrics of light fixtures, etc.), fenestration design (e.g., number, size, layout of windows), interior design (e.g., interior wall color, ceiling color, floor color, furniture color, furniture layout), the orientation of the room, shade positions, and other factors that reflect light. The melanopic ratio is a function of light type and CCT, however, CCT and intensity setting of electric lighting are only some of the parameters that can be influenced by the building control system; all other factors also may be considered (simulated or measured).

The intensity (brightness) of the light has an impact on circadian phase shift, mood, and alertness. To provide the highest level of electric lighting, the intensity is recommended to be set at maximum level (100%) for the energizing scene.

A field measurement may be conducted to ensure that 100% intensity of electric lighting in combination with daylight will result in 1000-2000 lux in regularly occupied areas of the bedroom for an energizing scene, as measured on the horizontal plane or in a typical angle of gaze.

The CCT of a light source is "a specification of the color appearance of the light emitted by a lamp, relating its color to the color of light from a reference source when heated to a particular temperature, measured in degrees Kelvin (K). Based on the research on the effects of bright light exposure on circadian phase shift, mood and alertness, the CCT for the Energizing Light scene is recommended to be set at 6500K for the energizing scene.

Although CCT is a widely used parameter in the lighting industry for setting up the system, a certain CCT is not directly correlated with a type of spectral power distribution (SPD), which correlates to the actual EML values. In other words, a particular CCT value can have numerous types of SPD, which may result in different EML values, and therefore may have different circadian effects on the residents.

In one approach, the blackout shade position is controlled by the local sunset time. During daytime before sunset, to maximize the daylight in the bedroom for the energizing scene, the shade is recommended to be set at fully open. At 1.5 hours after sunset, in order to protect the residents' privacy, the blackout shades are recommended to be set at fully closed. In one illustrative approach, a table of local sunset times will be included in the programming.

Thermal environments can influence physiological and psychological parameters associated with alertness, focus and comfort. Although temperatures below 23 degrees Celsius are typically associated with perceptions of discomfort, moderate exposure to cooler temperatures (20 degrees Celsius) have been shown to activate the nervous system controlling thermoregulation, which elevates mental alertness. Performance in general has been found to decrease as temperature rises above 24 degrees Celsius. Indoor temperature between 20 degrees Celsius and 22 degrees Celsius is found to have positive impact on occupant alertness and performance. Given that the temperature set-point throughout the day and night depends on individual thermal comfort preference, cultural differences, energy considerations, activities, clothing insulation, and many other factors, the temperature value for the energizing Scene is set to be 2 degrees Celsius lower than the temperature setting prior to switching on the Energizing Scene.

Figure 13:
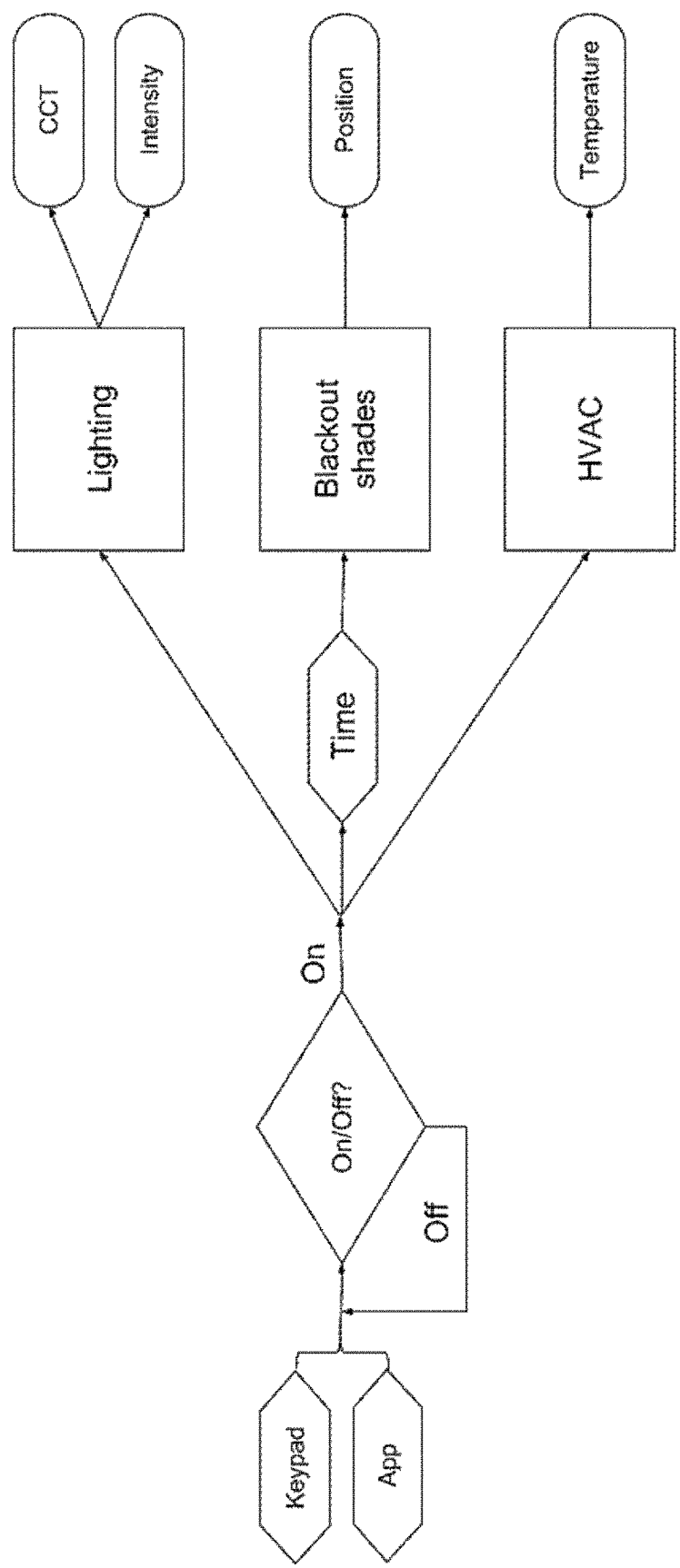
FIG. 13 illustrates a flow diagram showing a sequence of operations of an energizing scene according to an illustrated embodiment of the present invention.

FIG. 13 illustrates the sequence of operations for the energizing scene described above.

Example 3: Relax Scene

The indoor luminous environment has an impact on a person's visual and non-visual physiological and psychological functions. High indoor illuminance (1000 lux, as compared to the normal 200 lux) at eye level has alertness-enhancing effects (feeling more energetic and less sleepy) during both daytime and nighttime. The relationship between alertness and illuminance can be described as a sigmoid (s-shaped) function with a linear rise, representing increasing effects of light intensity on alertness, in normal room lighting. The color temperature of light also impacts alertness, with one study showing that exposure to low correlated color temperature (2700K) in children is "efficient at creating relaxing environments such as for those causing sleepiness". Another study on students showed that diastolic blood pressure under high CCT (7500K) was higher by 15% compared to that under other color temperature conditions. A study on adults also reported that participants felt more relaxed in warmer CCT environments compared to those with higher CCT.

Human thermal perception is related to not only air temperature, but also air velocity, relative humidity, clothing insulation, occupant metabolic rate, and mean radiant temperature of the environment, as defined by ASHRAE thermal comfort model. The perceptions of ambient thermal environments change with age, as elderly populations are physically more vulnerable to colder conditions. Indoor temperature between 20 degrees Celsius and 22 degrees Celsius is found to have positive impact on occupant alertness and performance. Lower room air temperature increased whole-body cooling sensation, which activates the brain and excites the nervous system controlling thermoregulation. Therefore, a higher room air temperature is desired for the Relax Scene.

The purpose of the relax scene in the bedroom is to create ambiance that may help the residents feel more relaxed through lighting, shades, and HVAC system settings at daytime or nighttime.

The Relax Scene is generally a scene for the bedroom that can be activated by both a keypad and smart phone app or other input device. After the relax scene is activated, the fully color-tunable LED downlights are programmed to provide low intensity (50%) and low CCT (2700K) light, the blackout or privacy shades on windows are programmed to be fully closed for both daytime and nighttime for privacy, and the thermostat is programmed to provide warmer temperature (+2 degrees Celsius). The shades may close over time or immediately. In some embodiments where multiple layers of shades are used, privacy shades may be lowered immediately while full blackout shades are lowered over time or also immediately. Electrochomatic glass also may be used to vary the transparency of the glass or the amount of light passing through the glass.

Below are a number of parameter settings, such as equivalent melanopic lux (EML), intensity, CCT, blackout shades, and temperature, used for a relax scene. Illuminance is the amount of light reaching a surface area from a light source and is commonly measured in either lux or foot candles (unit: lux or foot candle; 1 lux=1 lumen/m2, 1 fc=1 lumen/ft2). The lux unit, furthermore, is normalized to the color sensitivity of a standard observer at 1 m, with a peak sensitivity at ~550 nm (green), representing the accumulated activity of the three cone system in the foveal region of the eye (short-, middle-, and long-wavelength sensitive, or the blue, green, and red cones). Thus, the lux unit is useful in describing the amount of light that will be perceived by conscious high acuity, image-forming vision. The circadian system, however, relies on a combination of the three cone system and a system that is intrinsic to the ipRGCs—the melanopsin system. Unlike the three cone system used for image-formation, melanopsin is mostly sensitive to short (blue, ~490 nm4) wavelengths of light. A new unit, the melanopic lux (also referred to as melanopic illuminance) has been proposed as the amount of light that enters our eye affecting the melanopsin pigment in ipRGCs, taken as a multiple of photopic lux (RGB) and a given melanopic ratio. For proper alignment of the circadian system to the normal day, it is essential that there is a contrast between the EML during the day and during the night, with a greater EML throughout the day and lower at night. The greater the daytime light exposure, the higher the night time light exposure can be without deleterious effects on the circadian system.

The overall illuminance and EML at eye level are dependent on the building's lighting design (e.g., number, installation, and photometrics of light fixtures, etc.), fenestration design (e.g., number, size, layout of windows), interior design (e.g., interior wall color, ceiling color, floor color, furniture color, furniture layout), the orientation of the room, shade positions, and other factors that reflect light. The melanopic ratio is a function of light type and CCT, however, CCT and intensity setting of electric lighting are only some of the parameters that can be influenced by the building control system; all other factors also may be considered (simulated or measured).

The intensity (brightness) of the light has an impact on circadian phase shift, mood, and alertness. The relationship between alertness and illuminance can be described as a sigmoid (s-shaped) function with a linear rise, representing increasing effects of light intensity on alertness, in normal room lighting. During daytime when light intensity is greater, meaning that there is a reduction in the sensitivity of the circadian system because the background light intensity is greater. Studies have shown high illuminance (1000 lux compared to 200 lux) at eye level to have alertness-enhancing effects (feeling more energetic and less sleepy) during both daytime and nighttime. In order to help the residents achieve a relaxing effect, the intensity of the Relax Scene is set at 50%. The exact light intensity will be determined in practice when measuring the light levels in the specific room.

A field measurement may be conducted to ensure that 50% intensity will result in less than 200 lux at regularly occupied areas of the bedroom for the relax scene.

The CCT of a light source is "a specification of the color appearance of the light emitted by a lamp, relating its color to the color of light from a reference source when heated to a particular temperature, measured in degrees Kelvin (K). Studies have shown low CCT (2700K) to be efficient in creating a relaxed environment.

Although CCT is a widely used parameter in the lighting industry for setting up the system, a certain CCT is not directly correlated with a type of spectral power distribution (SPD), which correlates to the actual EML values. In other words, a particular CCT value can have numerous types of SPD, which may result in different EML values, and therefore may have different circadian effects on the residents.

The blackout shade position is recommended to be fully closed to protect the residents' privacy and may be programmed to operate as such for the relax scene.

Given that the temperature setpoint throughout the day and night depends on individual thermal comfort preference, cultural differences, energy considerations, activities, clothing insulation, and many other factors, the temperature setpoint is set to be 2 degrees Celsius warmer of its current setting for the relax setting.

Figure 14:
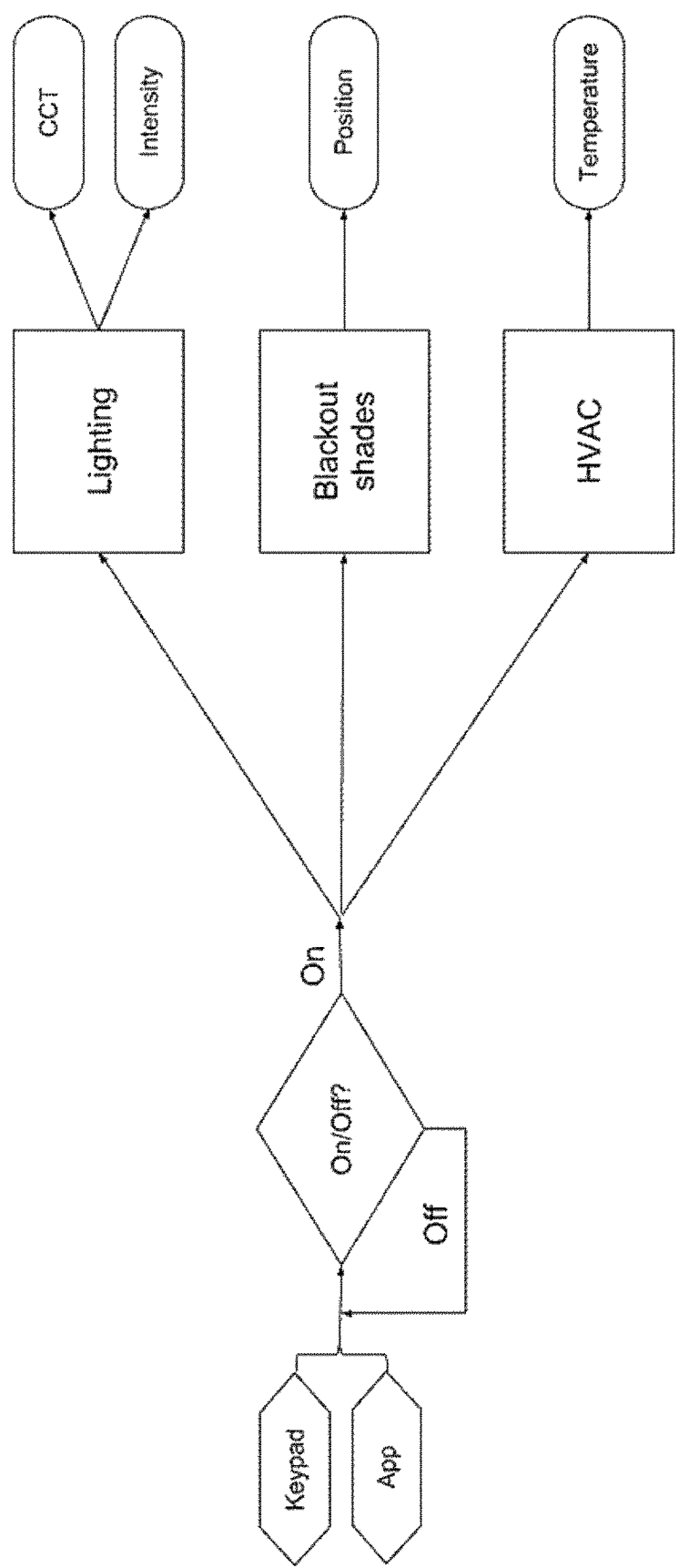
FIG. 14 illustrates a flow diagram showing a sequence of operations of a relaxation scene according to an illustrated embodiment of the present invention.

FIG. 14 illustrates the sequence of operations for the relaxation scene described above.

Example 4: Play Scene

The play scene is designed for residents to perform entertainment-related physical activities. The purpose of the play scene in the bedroom is to create exciting and colorful ambiance through certain settings of lighting, shades, and HVAC systems at daytime or nighttime.

The play scene is generally scene for a bedroom or other sub-space that can be activated by a keypad, smart phone app, or other input device. After the scene is activated, the fully color-tunable LED downlights are programmed to provide dynamic color show with 100% intensity. The blackout shades are programmed to be fully closed for both daytime and nighttime for privacy. The thermostat is programmed to decrease the temperature by 2 degrees Celsius.

Below are a number of parameter settings, such as CCT, intensity, blackout shades, and temperature, used for a play scene. Dynamic colors may be used for the play scene. Possible colors that can be considered for transitioning at certain time intervals and can be adjusted (from 1 second to 60 seconds) through a smartphone app. The default transition time is 3 seconds. The residents also may be able to pick a specific color for the entire time through their smartphone app for the play scene.

Three play scene modes can generally be set: rainbow mode (with full color light cycles through red colors at the beginning to pink/purple colors at the end); random mode (use a random algorithm (e.g., Monte Carlo) to select a color from the entire table and cycle through different random colors); and a manual mode (where the color space is shown on the smartphone app, and the occupant can pick any color manually through the app).

To provide the highest level of electric lighting level in the room for the play scene, the intensity is recommended to be set at the maximum level (100%) for the play scene. The residents have the ability to adjust the lighting intensity through the smart phone app.

The blackout shade position will be fully closed to protect residents' privacy for the play scene. The residents will have the ability to raise the shades if they want to.

The play scene is designed for entertainment-related physical activities, which may increase occupants' metabolic rate. Given that the temperature setpoint throughout the day and night depends on individual thermal comfort preference, culture difference, energy considerations, activities, clothing insulation, and many other factors, the air temperature setpoint is set to be 2 degrees Celsius lower compared to its current setting in the play scene.

Figure 15:
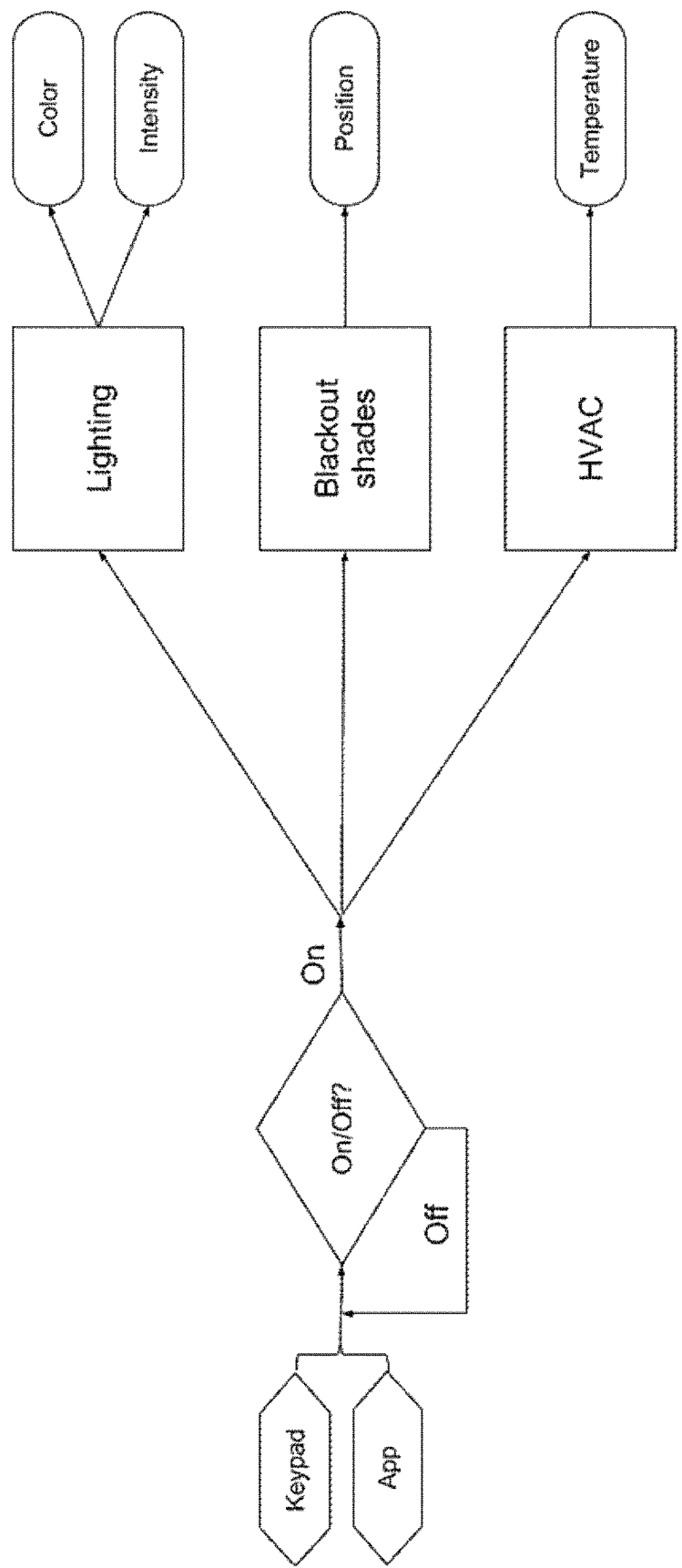
FIG. 15 illustrates a flow diagram showing a sequence of operations of a play scene according to an illustrated embodiment of the present invention.

FIG. 15 illustrates the sequence of operations for the play scene described above.

Example 5: Dawn Simulation Scene

Waking up with gradually increasing light—dawn simulation—can help to create a more pleasant waking up experience, including greater alertness, better mood, lower sleep inertia, and over time lead to improved circadian entrainment. The Dawn Simulation Scene provides a carefully coordinated schedule of six parameters—melanopic lux (m-lux), illuminance (lux), correlated color temperature (CCT), environmental temperature (° C.), sound intensity (dBA), and blackout shade movement—to ensure an improved waking up experience and circadian entrainment over time.

The dawn simulation scene can be activated via the smart phone app; the activation time needs to be set in the evening, prior to going to bed or can be synchronized with the alarm clock setting. Once activated, the fully color-tunable LED downlights are programmed to provide a gradual increase in CCT (1400K-2750K) and intensity (0-100%) over the course of 30 minutes. Over the last 2 minutes, nature sounds (forest birds, ocean waves, rain, etc.) are starting to play at a gradually increasing volume (30 dB-55 dB), reaching the maximum dB level 4 minutes after the maximum illuminance has been reached. At the end of the 30 minutes, the blinds go up, while the lights stay on at the same setting they had reached by the end of the 30 minutes for another 20 minutes, and are then changed to default bedroom control scene—circadian (or can be turned off via keypad or smartphone app). The sounds can either stay on at the maximum level that was reached at the 4-minute peak for the rest of the time that the lights stay on, or can be turned off via keypad or smartphone app. After the dawn simulation scene is complete, the lights may slowly fade over a particular amount of time to correct the circadian setting for the particular time of day.

In addition, after the dawn scene is activated, the thermostat is programmed to gradually increase the temperature by 2 degrees Celsius over the course of 30 minutes, then increase by another 1 degrees Celsius over the course of 20 minutes.

The thermostat is also programmed to decrease in temperature over a period of time via the Ready for Sleep setting until the start of the Dawn Simulation scene is activated. Sigmoid functions are implemented in the transition periods to minimize the noticeable change between different intensity levels.

Below are a number of parameter settings, such as equivalent melanopic lux (EML), intensity, CCT, speaker, blackout shades, and temperature, used for a dawn simulation scene. Illuminance is the amount of light reaching a surface area from a light source and is commonly measured in either lux or foot candles (unit: lux or foot candle; 1 lux=1 lumen/m2, 1 fc=1 lumen/ft2). The lux unit, furthermore, is normalized to the color sensitivity of a standard observer at 1 m, with a peak sensitivity at ~550 nm (green), representing the accumulated activity of the three cone system in the foveal region of the eye (short-, middle-, and long-wavelength sensitive, or the blue, green, and red cones). Thus, the lux unit is useful in describing the amount of light that will be perceived by conscious high acuity, image-forming vision. The circadian system, however, relies on a combination of the three cone system and a system that is intrinsic to the ipRGCs—the melanopsin system. Unlike the three cone system used for image-formation, melanopsin is mostly sensitive to short (blue, ~490 nm) wavelengths of light. A new unit, the melanopic lux (also referred to as melanopic illuminance) has been proposed as the amount of light that enters our eye affecting the melanopsin pigment in ipRGCs, taken as a multiple of photopic lux (RGB) and a given melanopic ratio. For proper alignment of the circadian system to the normal day, it is essential that there is a contrast between the EML during the day and during the night, with a greater EML throughout the day and lower at night. The greater the daytime light exposure, the higher the night time light exposure can be without deleterious effects on the circadian system.

The overall illuminance and EML at eye level are dependent on the building's lighting design (e.g., number, installation, and photometrics of light fixtures, etc.), fenestration design (e.g., number, size, layout of windows), interior design (e.g., interior wall color, ceiling color, floor color, furniture color, furniture layout), the orientation of the room, shade positions, and other factors that reflect light. The melanopic ratio is a function of light type and CCT, however, CCT and intensity setting of electric lighting are only some of the parameters that can be influenced by the building control system; all other factors also may be considered (simulated or measured).

Gradually increasing light intensity and color temperature during sunrise is the sun's natural pattern seen in nature. In several studies, dawn simulation devices had an increasing illuminance levels from 0 to 250-300 lux. These levels were found to have an effect on improving cognitive performance; earlier awakening, feeling more alert at awakening, getting up easier and having higher alertness at 2nd lesson at school in children and adolescents; improved alerting effect in adolescents; significantly gradient reduction in heart rate during the transition from sleep to wakefulness; improved perceived sleep quality, greater alertness, improved cognitive and physical performance after waking; improved subjective well-being, tension and mood, and improved cognitive performance; significant reduction in sleep inertia severity complaints and improved subjective well-being; significantly lower levels of sleepiness and greater levels of subjective activity; greater arousal (reporting being more alert and less tired); improved subjective sleep quality; and improved quality of awakening.

A field measurement may be conducted to correlate different intensity levels with the actual illuminance and EML at the bed surface, as measured on the horizontal plane or in a typical angle of gaze, to ensure the illuminance and EML requirements are met.

Although CCT is a widely used parameter in the lighting industry for setting up the system, a certain CCT is not directly correlated with a type of spectral power distribution (SPD). In other words, a particular CCT value can have numerous types of SPD, which may result in different EML values, and therefore may have different circadian effects on occupants.

The presence of sounds before, at and after sunrise—birds, insects, and other animals, flowing water, rain, thunder, ocean waves and others are commonly heard in nature. Sound intensity depends on the distance from the source of the sound, frequency of the sound, temperature, humidity, and various other factors. The range of dBA levels recorded in nature for bird sounds (flying, singing, song/call notes) varies from 30 to 62 dBA at a distance of 5-100 meters from the source; the range of wind sounds: 20-62 dBA; rainfall: 40-50 dBA; rustling leaves: 20-40 dBA; stream of flowing water: 73 dBA; pounding surf: 70 dBA; thunderstorm: 95-120 dB; waterfall: 45 dBA.

While there is a very wide variation of sound intensities with which people wake up (depending on the person's age, stage of sleep, hearing impaired/non-impaired status, intoxication, gender and others), a review of studies on fire alarm sound levels reports that dBA levels of 55-60 at pillow level will wake the average unimpaired sleeping adult.

The research on the effects of noise/sound and music on waking up/sleep inertia is scarce, but one study looking at the effects of sleep inertia dissipation after a 20-minute nap found greater reduction in subjective sleepiness, and further reduction in sleepiness and subjective comfort when hearing music of a higher preference.

Based on the sound intensity levels observed in nature that are noted above, the dawn simulator sound could vary between 20 and around 50-55 dBA, for the dawn simulation scene, with the highest levels occurring during the time after the highest lighting intensity has been reached. The goal is to awaken with increasing light levels, and ultimately circadian entrainment, not to be awoken by greater sound levels; sound is a component of the experience, but is not intended to act as an alarm to ensure awakening.

The thermal environment just prior to and immediately following a sleep period can have a significant impact on the ease of sleep initiation, the quality of sleep, and the rapidity of the transition from sleep to wake. During sleep, there is a 1° C. drop in the temperature of the brain, which activates cold-sensitive neurons in the brain that help to promote sleep. In the hours prior to normal arousal from sleep, there is a gradual return to daytime temperature in the brain, which helps to deactivate these sleep-promoting neurons and allow for a normal transition to wakefulness. The external thermal environment can be manipulated to accentuate this transition and create a state that is more conducive to arousal from sleep. More specifically, heat loss occurs through specialized blood vessels, arteriovenous anastomoses, which are present in the palms of the hands, soles of the feet, and on the face. During the arousal phase immediately preceding the transition from sleep to wake, there may be an increase in core body and brain temperature, which can be aided by a slightly warmer environment.

Temperature may vary throughout the day to reflect the temperature variation outdoors, both in terms of time of day as well as in terms of seasonality. Changes in temperature during the later portion of the day, starting at or before bed time and continuing until shortly after wake time, are especially important; daytime temperature regulation may be less important considering that the building residents may not be home.

The specific temperature values, or the starting value selected in the evening from which the temperature will start to drop until sunrise and then increase after sunrise may be chosen by the resident. However, the falling/increasing range will be defined, e.g., a drop in 3° C. then an increase in 3° C. The ranges may be informed by/consider the average drop in nighttime temperature and increase after sunrise at a given time of year, in the geographical area where the residents live; however, the temperature ranges in the home do not need to be as extreme/uncomfortable as they are in nature.

Having the blinds go up in the morning at the end of the dawn simulation is intended to allow the light from the outside to come in at the time the person has intended to wake up. The blinds may not go up earlier than at the end of the 30-minute dawn simulation period because if the light levels outside are greater than those provided by the dawn simulator at that time, then the lighting schedule may be thrown off track.

As another example of a dawn simulation scene, albeit one with an alarm type feature, suppose a user sets a wake up time alarm for 7:00 AM and the user goes to sleep in a bedroom or other sub-space. For purposes of the scene, a system, controlling device, controllable device or other device may then trigger an HVAC system to increase temperature two degrees Celsius from a nighttime set point over a thirty minute period starting at 6:30 AM. Prior to the alarm time (e.g., four minutes before 7:00 AM), the system, controlling device, controllable device or other device may trigger a sound or speaker system to gradually increase the dB level of biophila or other sounds in the bedroom or sub-space. At the wake up time of 7:00 AM, the system, controlling device, controllable device or other device raises the dB level of the sound over ten minutes unless the alarm is disabled. At the set alarm time of 7:00 AM, the system, controlling device, controllable device or other device may trigger blackout shades in for windows in the bedroom or space to fully open. Lighting in room also may be varied in a dawn simulation scene fashion prior to the alarm time of 7:00 AM to gradually help the user wake up.

Figure 16:
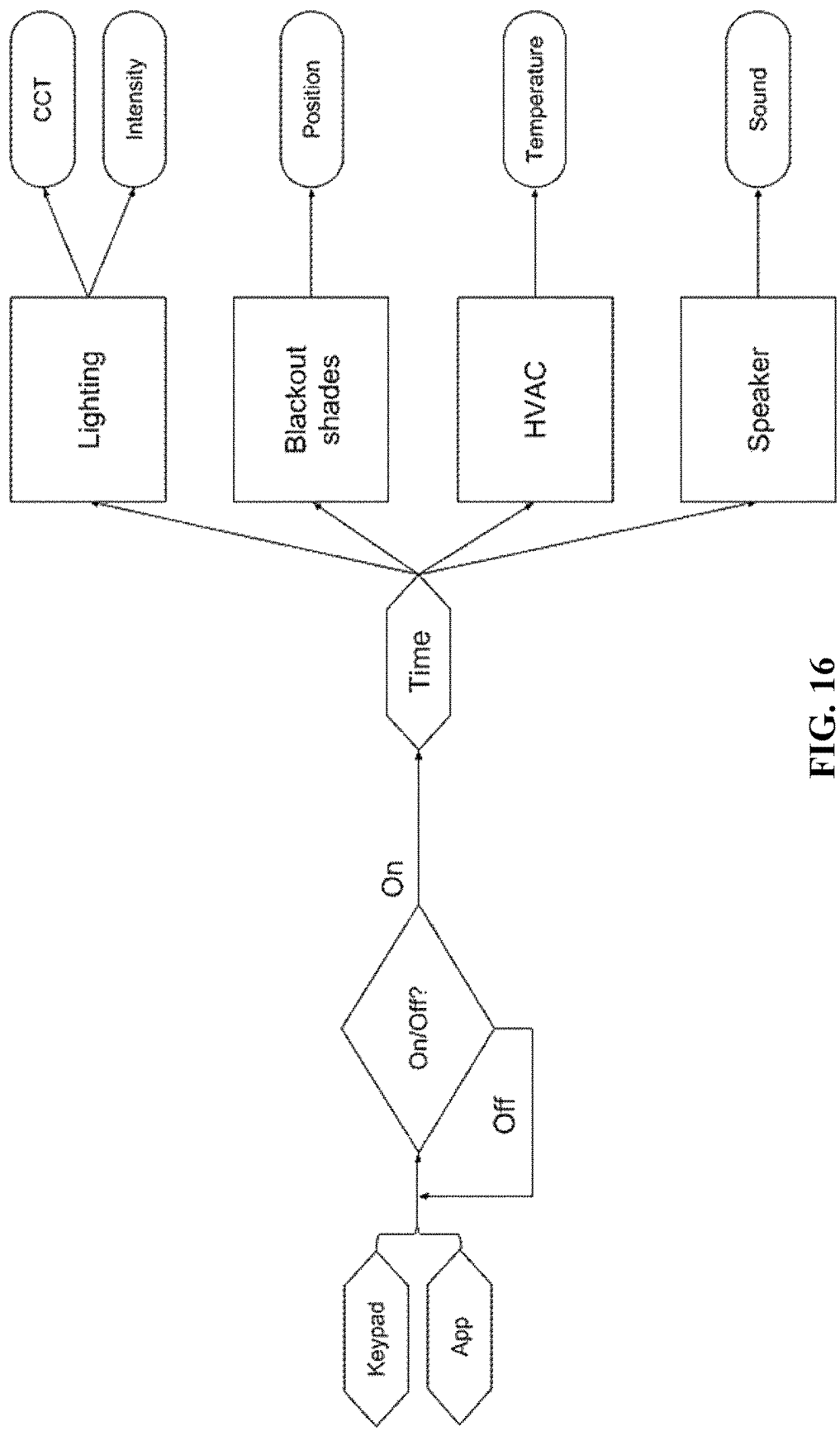
FIG. 16 illustrates a flow diagram showing a sequence of operations of a dawn simulation scene according to an illustrated embodiment of the present invention.

FIG. 16 illustrates the sequence of operations for the dawn simulation scene described above.

After the dawn simulation is complete, the scene transitions over time to the correct circadian setting based on that time of day, for example by fading the lights over the course of several minutes.

Example 6: Ready for Sleep Scene

Exposure to light at night disrupts the circadian rhythm and leads to melatonin suppression—a key hormone that signals to the body that it is time to go to sleep. Even brief exposures to light at night, especially light that is of short wavelength (in the blue spectrum), can disrupt the sleep-wake cycle, making it hard to fall back to sleep and in turn making it harder to wake up early in the morning.

Reduction in thermal climates at night are associated with better sleep quality, and room temperature can reach as low as 15 degrees Celsius while maintaining occupant thermal comfort. Temperatures that are too high (32 degrees Celsius) may increase sleep disturbances due to behavioral thermoregulation, increase incidences of mid-sleep waking, and decrease stage 2 and stage 4 sleep length (so-called, deep sleep). One study examining the cyclic changes in ambient bedroom temperatures found that gradual decreases in temperature from 27 degrees Celsius to 25.5 degrees Celsius between midnight and 4 am resulted in subjective reports of higher sleep quality.

The purpose of the Ready for Sleep scene in the bedroom is to create a transitional ambiance to prepare the residents for sleep through lighting, shades, and HVAC system settings at nighttime.

The Ready for Sleep scene can be activated only by the smart phone app. After the scene is activated, the fully color-tunable LED downlights are programmed to provide a CCT and light intensity that gradually transitions from the current setting to 2500K and 10%, respectively, over 15-60 minutes, depending on the user's choice (15, 30, 45, 60 minutes), then reducing the intensity to 0% 5 seconds after the set time has elapsed. The blackout shades are programmed to stay fully closed. The thermostat has two different settings depending on whether the Dawn Simulation scene is enabled or not. If the Dawn Simulation scene is enabled, the thermostat is programmed to decrease the temperature by 3 degrees Celsius during the whole night until the Dawn Simulation scene is activated in the morning. The decrease is sharpest at the beginning of the night, with a more gradual continuing decrease later in the night. If the Dawn Simulation scene is not enabled, however, the thermostat is programmed to decrease the temperature by 3 degrees Celsius during the 3 hour period after this scene has been activated. Then the thermostat setting will remain the same throughout the night. Then it will be automatically reset to its original setting at 10 am in the morning.

Below are a number of parameter settings, such as equivalent melanopic lux (EML), intensity, CCT, blackout shades, and temperature, used for a ready for sleep scene. Illuminance is the amount of light reaching a surface area from a light source and is commonly measured in either lux or foot candles (unit: lux or foot candle; 1 lux=1 lumen/m2, 1 fc=1 lumen/ft2). The lux unit, furthermore, is normalized to the color sensitivity of a standard observer at 1 m, with a peak sensitivity at ~550 nm (green), representing the accumulated activity of the three cone system in the foveal region of the eye (short-, middle-, and long-wavelength sensitive, or the blue, green, and red cones). Thus, the lux unit is useful in describing the amount of light that will be perceived by conscious high acuity, image-forming vision. The circadian system, however, relies on a combination of the three cone system and a system that is intrinsic to the ipRGCs—the melanopsin system. Unlike the three cone system used for image-formation, melanopsin is mostly sensitive to short (blue, ~490 nm) wavelengths of light. A new unit, the melanopic lux (also referred to as melanopic illuminance) has been proposed as the amount of light that enters our eye affecting the melanopsin pigment in ipRGCs, taken as a multiple of photopic lux (RGB) and a given melanopic ratio. For proper alignment of the circadian system to the normal day, it is essential that there is a contrast between the EML during the day and during the night, with a greater EML throughout the day and lower at night. The greater the daytime light exposure, the higher the night time light exposure can be without deleterious effects on the circadian system.

The overall illuminance and EML at eye level are dependent on the building's lighting design (e.g., number, installation, and photometrics of light fixtures, etc.), fenestration design (e.g., number, size, layout of windows), interior design (e.g., interior wall color, ceiling color, floor color, furniture color, furniture layout), the orientation of the room, shade positions, and other factors that reflect light. The melanopic ratio is a function of light type and CCT, however, CCT and intensity setting of electric lighting are only some of the parameters that can be influenced by the building control system; all other factors also may be considered (simulated or measured).

Melatonin, an essential hormone in the onset of sleep, can be fully suppressed at higher light intensities, typically over 1000 lux. Partial suppression, however, begins at much lower levels of illuminance (~20-50 lux) and even normal room light can cause significant suppression of melatonin. Since it may still be important to have some light for safe navigation before bed, the light intensity is set at 10% in the ready to sleep scene. Once the scene ends, the lights fade off over 5 seconds (0% intensity) in this scene.

A field measurement may be conducted to correlate different intensity levels with the actual illuminance and EML levels at the bed surface to ensure the illuminance and EML requirements are met.

The CCT of a light source is "a specification of the color appearance of the light emitted by a lamp, relating its color to the color of light from a reference source when heated to a particular temperature, measured in degrees Kelvin (K). A study examining the effects of different color temperature on sleepiness found that 2500K had the least impact on alerting effects (reducing sleepiness) and was associated with higher levels of salivary melatonin production.

Although CCT is a widely used parameter in the lighting industry for setting up the system, a certain CCT is not directly correlated with a type of spectral power distribution (SPD). In other words, a particular CCT value can have numerous types of SPD, which may result in different EML values, and therefore may have different circadian effects on the occupants.

The blackout shade position is recommended to be fully closed to protect the residents' privacy and prevent any daylight entering the room during the ready to sleep scene.

Gradual decreases before sleeping have been associated with better quality sleep. Since thermal comfort is highly individual, depending on insulation layers, and individual and cultural differences, relative changes in temperature, dependent upon what the occupants may be set as their optimal temperature on the in-built thermostat. A 3° C. change in temperature over a 3-hour period starting at sunset time has been shown to have significant effects on sleep onset and waking.

As one example, for a sleep scene selected by a user or implemented in a space or sub-space, a system, controlling device, controlled device or other device may cause temperature in the space or sub-space to decrease two degrees Celsius over a thirty minute period and black-out shades or privacy shades to close at the beginning of the scene or gradually over time. Background white noise also may be played to limit the impact or irregular or other sounds which may be heard in the space by the user or which may make it difficult for the user to fall asleep.

Figure 17:
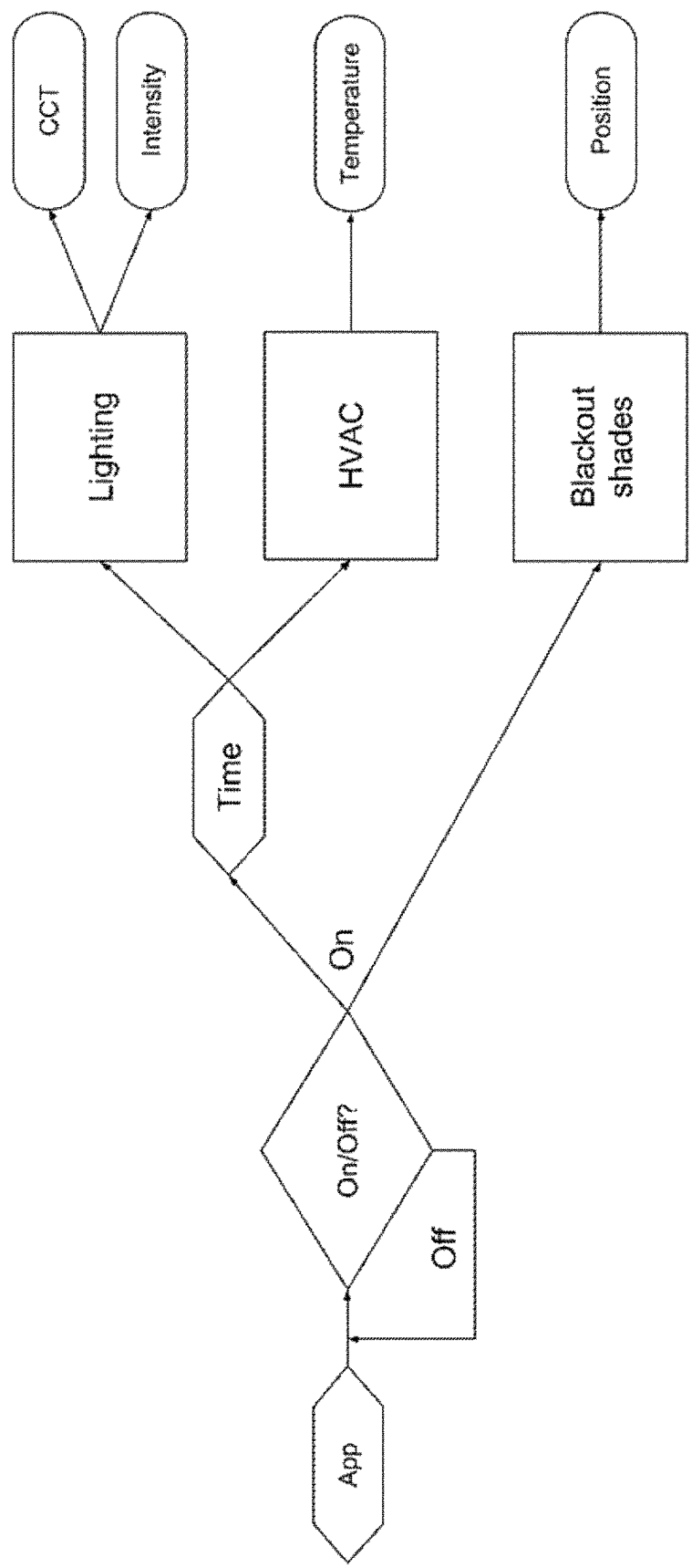
FIG. 17 illustrates a flow diagram showing a sequence of operations of a ready for sleep scene according to an illustrated embodiment of the present invention.

FIG. 17 illustrates the sequence of operations for the sleep scene described above.

Example 7: Night Light Scene

Exposure to light at night disrupts the circadian rhythm and leads to melatonin suppression 34—a key hormone that signals to the body that it is time to go to sleep. Even brief exposures to light at night, especially light that is of short wavelength (in the blue spectrum), can disrupt the sleep-wake cycle, making it hard to fall back to sleep and in turn making it harder to wake up early in the morning. It is therefore essential to provide night lighting that is dim and of a spectrum that minimizes the light in the blue band while providing adequate light levels for safe night time navigation.

Exposure to light at night disrupts the circadian rhythm and leads to melatonin suppression—a key hormone that signals to the body that it is time to sleep. Even brief exposures to light at night, especially light that is of short wavelength (in the blue spectrum), can disrupt the sleep-wake cycle, making it hard to fall back to sleep and in turn making it harder to wake up early in the morning.

The purpose of the Night Light scene in the bedroom is to provide minimum lighting for residents to safely get up and navigate the room at night with reduced disruption to their circadian rhythm.

The Night Light scene is activated by motion and light sensors. After the scene is activated, the night light is turned on. The light is turned off after 5 minutes when no motion is detected. The residents may be able to disable or turn off the night light via a wall switch or smart phone app.

Below are a number of parameter settings, such as equivalent melanopic lux (EML), illuminance, light wavelength, and CCT used for a ready for the night light scene. Illuminance is the amount of light reaching a surface area from a light source and is commonly measured in either lux or foot candles (unit: lux or foot candle; 1 lux=1 lumen/m2, 1 fc=1 lumen/ft2). The lux unit, furthermore, is normalized to the color sensitivity of a standard observer at 1 m, with a peak sensitivity at ~550 nm (green), representing the accumulated activity of the three cone system in the foveal region of the eye (short-, middle-, and long-wavelength sensitive, or the blue, green, and red cones). Thus, the lux unit is useful in describing the amount of light that will be perceived by conscious high acuity, image-forming vision. The circadian system, however, relies on a combination of the three cone system and a system that is intrinsic to the ipRGCs—the melanopsin system. Unlike the three cone system used for image-formation, melanopsin is mostly sensitive to short (blue, ~490 nm) wavelengths of light. A new unit, the melanopic lux (also referred to as melanopic illuminance) has been proposed as the amount of light that enters our eye affecting the melanopsin pigment in ipRGCs, taken as a multiple of photopic lux (RGB) and a given melanopic ratio. For proper alignment of the circadian system to the normal day, it is essential that there is a contrast between the EML during the day and during the night, with a greater EML throughout the day and lower at night. The greater the daytime light exposure, the higher the night time light exposure can be without deleterious effects on the circadian system.

The overall illuminance and EML at eye level are dependent on the building's lighting design (e.g., number, installation, and photometrics of light fixtures, etc.), fenestration design (e.g., number, size, layout of windows), interior design (e.g., interior wall color, ceiling color, floor color, furniture color, furniture layout), the orientation of the room, shade positions, and other factors that reflect light. The melanopic ratio is a function of light type and CCT, however, CCT and intensity setting of electric lighting are only some of the parameters that can be influenced by the building control system; all other factors also may be considered (simulated or measured).

Illuminance is the amount of light reaching a surface area from the light source and is measured in either lux or foot candles (unit: lux or foot candle; 1 lux=1 lumen/m2, 1 fc=1 lumen/ft2). Illuminance below 15 lux (at corneal level in the horizontal angle of gaze) has been found to evoke minimal melatonin phase shift. However, given the dark adapted state of the retina, the intention to not wake up a partner who may also be sleeping in the bedroom, and to minimize melatonin suppression and circadian disruption, the illuminance of night lights may be even lower—at or below 5 lux, as measured at corneal level in the horizontal angle of gaze.

If needed, the lighting can be programmed to provide greater illuminance (15-20 lux) for individuals with vision impairments such as cataracts or glaucoma, as less light would be penetrating the lens in these conditions.

The various types of light that make up the electromagnetic spectrum differ in wavelength. The human circadian system is particularly sensitive to short wavelength light in the blue spectrum, with peak circadian sensitivity at 470-490 nm.4 At the wavelength of 555 nm and greater, the relative sensitivity to melatonin suppression drops significantly. Therefore, the majority of the spectral power of the night lights may be greater than 555 nm, which still significantly stimulates the image formation necessary to safely navigate to the bathroom, while minimizing the proportion of 480 nm band of the spectrum.

The CCT of a light source is "a specification of the color appearance of the light emitted by a lamp, relating its color to the color of light from a reference source when heated to a particular temperature, measured in degrees Kelvin (K)". for a night light scene, the recommended CCT is 2300 K or lower, based on a study that found no effect of melatonin secretion with exposure to light of 2300 K, 200 lux (at eye level) for 1.5 hours at midnight, whereas melatonin secretion was measurably suppressed at 3000 K and acutely suppressed at 5000 K.

Figure 18:
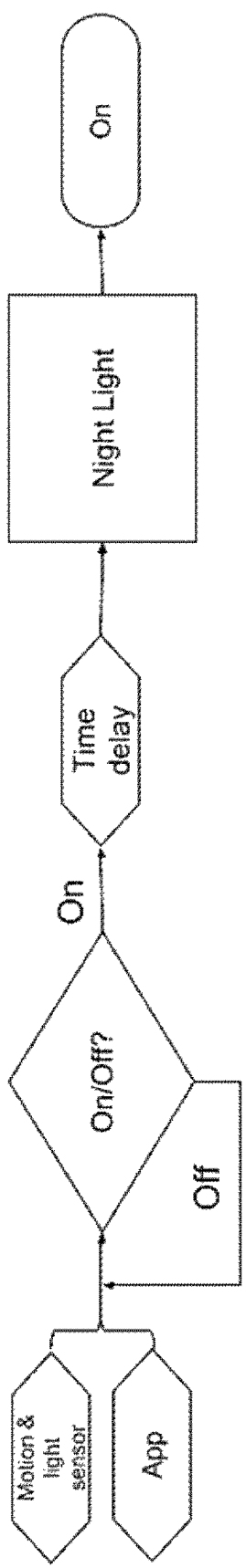
FIG. 18 illustrates a flow diagram showing a sequence of operations of a night light scene according to an illustrated embodiment of the present invention.

FIG. 18 illustrates the sequence of operations for the night light scene described above.

Several other scenes are also possible in any of the spaces or sub-spaces discussed above. The following are additional illustrative examples of scenes for use in an office space or work space. In one illustrative approach, a focus scene is configured with work lights that brighten and a temperature that drops in order to help a user focus on the task at hand. In another approach, a dynamic scene includes lighting, temperature, and/or ambient noise that varies overtime to simulate the dynamic conditions one would experience outside. For example, the lights could slightly dim and temperature slightly drop to simulate a cloud passing in front of the sun.

By one approach, one or more office scenes may be triggered by certain scheduled events. For example, when the calendar has a meeting scheduled for a conference room, the ventilation can be increased and the temperature decreased shortly before the meeting in order to correct for or anticipate the large amount of people scheduled to be entering the conference room. The breakroom can be cooled in anticipation for the lunch break and sound masking can be increased to correct for the large number of people expected. Or sound masking can be increased in an office at the start of the business day to cover the noise of people arriving at work and making their small talk as they enter.

By another approach, one or more office scenes may be triggered by sensors. If a user's wearable sensors or chair sensors detect that the user has been seated for an extended period of time or is seated with poor posture, it may prompt the user to get up and move around and/or cause the configuration of the workspace to change by converting the desk to a standing desk. If the wearable sensor or sensors in the kitchen detect that a user has made several trips to a soft drink fridge or snack cabinet the user may be prompted to adjust their diet. If emergency sensors detect an emergency situation, workstation lights may shutoff to prevent a user from continuing to work, alarms may notify the user of the emergency, and lights may illuminate the pathway to the appropriate exit or shelter.

Residences of senior citizens or other at risk individuals are also well suited for a number of scenes. Wearable sensors, smart floor sensors, bed sensors, motion sensors, and/or door sensors can detect the amount of time a person spends in bed. If the user spends too much time in bed the system may alert them to get up and move around, or could alert a caregiver to help the user get up and move around. In some embodiments, the wearable device includes a UV sensor, when it detects that the user has not spent enough time in sunlight it may prompt the user to go outside and/or opens blinds. The prompt could be an audio queue signifying the outside, such as the sound of birds chirping. When a wearable sensor, motion sensor, floor sensors, and/or door sensors detect that the user has not entered the kitchen in an extended period of time, the system may notify the user to get food. When the emergency sensors detect an emergency (such as, for example, the floor sensors detecting a sudden and large force hitting the floor), an emergency scene alerting the user (and medical personnel) can be triggered. Furthermore, the emergency scene may be personalized to compensate for any weakened senses the user(s) have, for example the indicators can be sound based in the residence of a user with poor eyesight, or sight based in the residence of a user with poor hearing. Additionally, sensors can monitor the user's ECG, pulse, blood pressure, or activity level. When a medical emergency is detected the system may contact medical personnel, emergency services, and/or an emergency contact and may unlock the door to grant the first responder access to the space or sub-space. Lights and/or sound may be used to direct the first responder to the user.

Residential scenes can also be used to prompt users to carry out basic household chores. Illustrative examples include indications to walk, feed, and/or water pets, indicators when it is time to prepare meals, indicators to take out the garbage on garbage day, and indicators to mow the lawn, among many others.

Gyms are another space with a number of possible scenes. Sensors can be used to detect the number of patrons in a gym, their location within the gym, and their activity. HVAC, humidity controls, noise masking, aroma control, and other systems can be controlled to preemptively mitigate the problems associated with smaller or larger groups. Lights and sound can also be used to direct the gym patrons through their exercise. For example, higher tempo music and or strobe lights can be used to set a fast workout pace, and slower music and dim lights can be used to set a cooldown pace.

In the above examples, the means used to alert the user can vary. Alerts can involve blinking or adjusting lights, emitting sounds, emailing or texting the user, or having an application give a notification on a smartphone, tablet, or computer. Alternatively, the user may direct the system to automatically adjust for certain detected conditions without alerting the user or other inhabitants.

In some embodiments, a system may set a scene within a space or sub-space at a certain or preset time, upon request from a user or input or other device in the space or sub-space, upon request from a user or input or other device external to the space or sub-space, automatically upon a user condition (e.g., heart rate, body temperature, galvanic skin response, lack of movement for a designated period of time), upon the identification or determination of a usage occasion or user goal, automatically upon a condition within the space or sub-space preset by a user internal to or external to the space or sub-space, upon a specific environmental condition within the space or sub-space, and/or upon a specific environmental condition external to the space or sub-space, among others. In some embodiments, preset or operating times for one or more scenes for a space or sub-space may vary by date, day of week, month of year, time of day, season, external weather conditions, user preferences, user needs, user goals, type of space or sub-space, configuration of space or sub-space, intended use of space or sub-space, number of occupants in a space or sub-space, controllable devices available for the space or sub-space, and/or other factors.

In some embodiments, if a user regularly changes a setting within a scene in a space or sub-space, a system may reset the default conditions for the scene automatically or upon requesting and/or receiving approval from the user and/or based on one or more other inputs. For example, if a user regularly reduces the air temperature or lighting intensity in a space or sub-space after the system sets a default scene for the space or sub-space, the system may adjust the default for the scene so that the lower air temperature and lighting intensity is established as the default setting for the scene. As another example, if multiple users in different but similar spaces or sub-spaces, regularly change a setting within a scene for such space or sub-space, a system monitoring, managing and/or controlling such spaces or sub-spaces may change the default settings for the scene in some or all of the spaces or sub-spaces monitored, managed or controlled by the system, even if one or more users in one or more similar spaces or sub-spaces have not made similar changes to the default settings for the scene or requests for such changes.

In some embodiments, a system may change one or more settings temporarily or permanently in a scene due to external conditions, time of day, day of week, month of year, season, date, cultural norms or traditions, location of space or sub-space, attribute of a user, attribute of a group of users, user goal, usage occasion, attribute or feature of a space or sub-space, etc. This may happen automatically on a temporary or permanent basis by a system, upon request and/or approval from a user, upon receipt of a signal from an input device, upon request from the system, only after multiple users make such a request, after other conditions or requirements are met, etc. For example, if the air temperature outside a space or sub-space is unusually high or depending on the date or season, the system may change the default setting for a scene temporarily or permanently to facilitate creation of or shorten transition to the scene within the space or sub-space or to increase likelihood of the scene being maintained with the space or sub-space. As another example, if a space or sub-space is located in a city or other location having poor air quality, the system may change the air quality setting for a scene to make sure that the opening of doors or windows do not adversely impact environmental conditions within the space or sub-space or that that a scene having specific air quality requirements is obtained faster within the space or sub-space. As another example, desired lighting levels when dining may vary by type or location of a restaurant, type of food being served at the restaurant, cultural differences, etc. A system may change default one or more default settings associated with the scene based on such variances.

In some embodiments, a system or device associated with a space or sub-space may provide or help provide one or more outputs to a system or one or more devices in or related to the system, to a space or sub-space, one or more devices in or related to a space or sub-space, one or more users, etc. Outputs may include or be signals, data, information, etc. For example, such outputs may include one or more of the outputs described in the table below or one or more other outputs.

TABLE 3

| OUTPUTS | |
|---|---|
| Signal or information sent to controlled device | Turn on, turn off, reconfigure, reset, recalibrate<br>Change or override setting limits<br>Change or override user preferences or settings<br>Change or override default setting<br>Turn on, turn off, reconfigure, reset, recalibrate<br>Establish, end or change a scene |
| Signal or information sent to controlling device | Change setting or operation of controlled device<br>Provide information regarding current setting or operation of controlled device<br>Turn on, turn off, reconfigure, reset, recalibrate a controlled device<br>Turn on, turn off, reconfigure, reset, recalibrate<br>Establish or change a scene |
| Signal or information sent to data storage device | Change, delete or add data<br>Change, add or delete access, security, or back-up processes<br>Turn on, turn off, reconfigure, reset, recalibrate<br>Document scene setting, scene change, scene launch, scene end, etc.<br>Document information regarding a user, space, sub-space or scene |
| Signal or information sent to alerting device | Create low, medium or high alert<br>Send additional alarm notification<br>Operate independently going forward<br>Activate additional sensor or transducer device capability<br>Turn on, turn off, reconfigure, reset, recalibrate |
| Signal or information sent to sensor or other transducer device | Collect additional or new data<br>Change measurement target or measuring process<br>Turn on, turn off, reconfigure, reset, recalibrate<br>Send alert or notification to local device, space or sub-space manager or managing device, etc. |
| Signal or information sent to user | Via phone, computer, speaker, terminal, tablet, display, controlling device, controlled device, alerting device, wearable device, space or sub-space feature or device, other device, etc.<br>Via local or remote third party<br>Via known or unknown third party<br>Via direct or indirect route or means<br>In conjunction with alerting, configuration, tagging or other information regarding controlled device, controlling device, alerting device, sensors or other transducer devices, location, space, sub-space, data storage device, etc.<br>Current environmental condition within a space or sub-space<br>Current operational state of a device within a space or sub-space<br>Potential operational state of a device with a space or sub-space<br>Current or expected environmental condition external to a space or sub-space<br>Recommended scene, scene schedule, scene change, etc.<br>Current scene, scene setting, scene change, scene duration, scene feature, scene transition plan, etc. |
| Signal or information sent to analysis device | Update, ignore, replace, add or delete data or input<br>Turn on, turn off, reconfigure, reset, recalibrate<br>Update, modify, reset or ignore inputs, previous results, algorithms, user requests, scene default settings, etc.<br>Resend or recalculate prior output<br>Evaluate or analyze scene, user, space, sub-space, device, usage occasion, user attribute, etc.<br>Determine or establish a new scene<br>Determine transition plan to new scene<br>Determine capability of controlled device in a space or sub-space |

TABLE 3-continued

| OUTPUTS |
| --- |
| Determine location of user in a space of sub-space |
| Determine current or prior environmental parameter in a space or sub-space |
| Establish new default setting for scene |
| Determine ability of scene to be established in a space or sub-space |
| Determine ability of a controlled device to establish an environmental parameter in a scene, space or sub-space |

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs) or programmable gate arrays or programmable logic circuits (PLCs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

The above discloses the use of air filters, aromatherapy, blackout shades, circadian lighting, comfort flooring, energizing light, interior wall acoustics, night lights, point of use water filtration, and UVGI lights. Exemplary specifications for each of these are provided below. The exemplary specifications below can be used in any of the embodiments described above.

Air constantly flows into homes and is subject to a wide range of pollutants both from outdoor air pollution and source contaminants within the home. Indoor air pollution is among the top five environmental health risks and has been shown to be 2-5 times higher than the pollution of outdoor spaces—up to 100 times higher in extreme cases. Therefore, effectively managing indoor air quality through the filtration of air drawn from outdoors and the circulation of indoor air can help reduce the concentration of contaminants in the home. Table 4, below, outlines exemplary specifications for the use of air filters used in some embodiments.

TABLE 4

| CRITERIA | DEFINITION AND REQUIREMENTS |
| --- | --- |
| MERV 13 Filter or higher Based on A SHRAE 52.2 | According to ASHRAE 52.2 (2012, with 2015 amendments), filters with MERV ratings of 10 or higher will remove at least 50% of all particles of 1 to 3 µm, those of 13 or higher will remove at least 85%, and those with a MERV 14 filter will remove at least 75% of particles with a diameter of 0.3 to 1 µm (see table below). The MERV 13 requirement only applies to the ducted air distribution systems; non-ducted air systems should have similar air filters inside the airhandling unit. Note: Higher MERV ratings do not contribute to significant changes in energy consumption; in a study on two typical residential systems (forced air for heating and direct expansion for cooling), one of the conclusions was that "daily energy consumption did not significantly differ between low- and high-MERV filter installations' (low = MERV 4 and high = MERV 11). Between MERV 8 and MERV 11, there was minimum difference in energy. |
| No Electronic Air Cleaners | Electronic air cleaners may be effective in removing small particles but are not as effective in removing large ones. In addition, they can produce ozone (amounts vary depending on the model), which is a lung irritant. When ozone produced by the electronic air cleaners reacts with particles from household cleaning products, off-gassed particles and other chemicals present in the space, ultrafine particles can be formed, which may be associated with adverse health outcomes in sensitive populations. |
| Fine Fiber Media | Filters with a fine fiber media are preferable to those with coarse fibers. Fine fiber media does not rely on an electrostatic charge whereas coarse fiber does; this allows fine fiber media to maintain efficiency over time, while the electrostatic charge in coarse fibers loses efficiency over time. |
| No Ozone Emissions | Based on the evidence on the harmful effects of ozone, and products formed via reaction of ozone with other particles on human health, the U.S. EPA recommends not to use air cleaners that emit ozone. When present in the air and inhaled, ozone can lead to chest pain, coughing, lung damage, and lead to worsening of chronic respiratory diseases (e.g., asthma). Based on the EPA's recommendation, air filters preferably do not produce ozone. |
| Ventilation Rate Requirements | The air distribution systems with the required air filters preferably meet the minimum ventilation rate requirements defined by ASHRAE 62.1-2013. |

Derived from traditional remedies, aromatherapy is the use of essential oils from herbs, flowers and trees to support emotional and spiritual well-being. Aromatherapy is preferably delivered through cool diffusion to avoid changing the natural properties of the essential oils. Some benefits of aromatherapy include alleviating anxious behaviors and aiding in relaxation. Table 5, below, outlines exemplary specifications for the use of essential oils used in some embodiments.

TABLE 5

| CRITERIA | DEFINITION AND REQUIREMENTS |
| --- | --- |
| 100% Natural Essential Oils | Since synthetic fragrances can be produced from petrochemicals, aromatherapy products are preferably made from 100% natural essential oils. |
| Steam Distillation | Essential oils are preferably extracted through a steam distillation process in order to minimize or remove human toxicity. |
| Non Toxic | Oils used do not fall into toxicity/poison schedules of the following bodies: US Food & Drugs Administration (FDA), Australian Government Therapeutic Goods Administration (TGA), and Council of Europe (Active principals list). |
| Cool Diffusion Methods | Diffusion methods involving heat can change the natural properties of essential oils and leave behind a sticky residue. Cool diffusion methods are preferably utilized. |
| Safety Labels | All aromatherapy products are labelled for intended use (e.g., inhalation, topical, consumption, etc.) and precautions in handling (e.g., Keep out of reach of children; Do NOT swallow) and storage (temperature, relative humidity ranges). Information for recovery of immediate exposure is made readily available. |

Exposure to light at night during sleep time—even in minute quantities—can have dramatic impacts on the circadian rhythm. Especially in urban settings, light pollution at night has become a major concern for human health. While indoor lighting can be easily controlled by occupants, it is also important to provide means for occupants to minimize light from outdoors through fenestrations.

Blackout shades are typically used to help minimize outdoor light intrusions during night time, including but not limited to roller shades, cellular shades and drapery shades. Table 6, below, outlines exemplary specifications for the use of blackout shades used in some embodiments.

TABLE 6

| CRITERIA | DEFINITION AND REQUIREMENTS |
| --- | --- |
| Visible Light Transmittance (VLT) | VLT is defined as the percentage of the total visible light allowed to pass through the shades and fenestrations combined. In order to minimize the outdoor light intrusions, the blackout shades preferably have a VLT rating of approximately 0. |
| Side and Bottom Channels (or pockets) (only applies to roller shades) | Channels or pockets are utilized to prevent outdoor light leakage into the interior spaces. |
| Minimal VOC Emissions | The blackout shades preferably meet third party certification low VOC (e.g., Greenguard Gold or Green Tag Certification) requirements. |
| Controls | Motorized (or automated) blackout shades are recommended. Studies show that compared to manual shades, motorized (or automated) shades are more often used by occupants, which may increase the occupants' willingness to use blackout shades at night. |

In addition to vision, light influences the human body in a number of ways to which people respond subconsciously, including mood, alertness, and cognitive ability. Humans and animals have an internal clock that keeps the body on a roughly 24-hour cycle, in what is called the circadian rhythm. Multiple bodily processes, including sleep and digestion are regulated in part by the daily hormonal fluctuations of the circadian rhythm. These hormones are released by an area in the brain called the hypothalamus. The hypothalamus times its hormonal outputs based on the timing of light exposure, which it receives via specialized cells in the eye, called ipRGCs. Daily, regularly-timed light exposure is required to maintain a healthy and robust circadian rhythm, called "entrainment". Table 7, below, outlines exemplary specifications for the use of circadian lighting used in some embodiments.

TABLE 7

| CRITERIA | DEFINITION AND REQUIREMENTS |
| --- | --- |
| Correlated color temperature (CCT) range | The CCT of a light source is "a specification of the color appearance of the light emitted by a lamp, relating its color to the color of light from a reference source when heated to a particular temperature, measured in degrees Kelvin (K)". 17 The range of CCT capability is preferably 2700-6500 K. |
| Fully Color-Tunable | The circadian lighting solutions preferably allow for full color tunability. This allows for infinite and appropriate color selection. |
| Programmable Light Parameters | Ability to customize CCT, light output (lumens) and chromaticity via manual or automated controls. The lighting parameters are be programmable. |
| Color Rendering Index (CRI) | The color rendering index (CRI) is a quantitative measure of the ability of a light source to reveal the colors of various objects accurately in comparison to a reference light source. The CRI is preferably greater than 80 and the light is capable of maintaining that CRI at any point along the Black Body Curve from 2700 K to 6500 K. |
| Dimming Range | Ability to increase or decrease light output (lumens). The dimming range is from 0.1% to 100%. |
| Color Point Accuracy | LED lights preferably employ closed loop optical and thermal feedback capable of maintaining color point accuracy of <1 MacAdam Ellipse. |
| Light Output | A measure of the total quantity of visible light emitted by a source. A-Lamps preferably have a lumen output rating of at least 600 lumens. |

Whether standing all day or working in the kitchen, the air contained between the millions of cork cells provides a supported feel underfoot. It does not feel spongy since it layers under the floor tiles, but it does act as a shock absorber and provides sufficient comfort to people standing on their feet for long periods of time. Table 8, below, outlines exemplary specifications for the use of comfort flooring used in some embodiments.

TABLE 8

| CRITERIA | DEFINITION AND REQUIREMENTS |
| --- | --- |
| Compression | ASTM F36-15 is a standard test method to understand the short-time compressibility and resilience at room temperature of gasket materials. Cork flooring with higher compression versus lower compression should be used. |
| Minimal VOC Emissions | Cork flooring preferably meets third party certification low VOC (e.g., Greenguard Gold or Green Tag Certification) requirements. |
| Tensile Strength | ASTM F152-95 is a standard test method to understand the tensile strength of nonmetallic gasket materials such as cork (Type 2 in Classification F104), given as a measurement of force in kilopascals (kPa). Cork flooring with higher tensile strength versus lower tensile strength should be used. |
| Recovery | Describes the amount of indentation that remains after the cork has been depressed and allowed to recover for a certain amount of time. It is usually stated as a percentage of the original depression. Cork flooring with higher recovery rate versus lower recovery rate should be used. |

The human body clock runs on a schedule that is naturally about 24 hours and 15-30 minutes long. Unless regularly reset, this 15 to 30-minute discrepancy makes us want to go to sleep later and wake later, relying on alarm clocks in the morning in order to function on a 24-hour day schedule. Bright light is the strongest entraining agent of the human circadian rhythm, and exposure to light in the morning can make waking up easier.

Morning use of bright light is known to phase-advance (shifting the sleep phase earlier), whereas evening use is known to phase-delay (shifting the sleep phase later) the circadian rhythm. In order to have sleep and wake patterns that are better aligned with the schedules of work, school or social activities, individuals who are very early risers may want to delay the timing of their sleep, whereas "night owls" may want to advance it. Phase advancing may also be of interest to individuals who are traveling east in order to reduce the symptoms of jet lag, and to shift workers on early morning shifts who want to fall asleep and wake earlier. Table 9, below, outlines exemplary specifications for the use of energizing light used in some embodiments.

TABLE 9

| CRITERIA | DEFINITION AND REQUIREMENTS |
|---|---|
| Illuminance | Illuminance is the amount of light reaching a surface area from the light source and is measured in either lux or foot candles (unit: lux or foot candle; 1 lux = 1 lumen/$m^2$, 1 fc = 1 lumen/$ft^2$). Based on four studies examining the effects of bright light exposure on circadian phase shift, mood and alertness, the level of illuminance for the Energizing Light is between ~3000 lux and ~9000 lux, as measured at eye level in the angle of gaze. Due to the high illuminance levels towards the higher end of this range, the illuminance of the Energizing Light should preferably be towards the lower end (~3000 lux) of the spectrum. |
| Correlated Color Temperature (CCT) | The CCT of a light source is "a specification of the color appearance of the light emitted by a lamp, relating its color to the color of light from a reference source when heated to a particular temperature, measured in degrees Kelvin (K)". Based on four studies examining the effects of bright light exposure on circadian phase shift, mood and alertness, the CCT for Energizing Light is be between 4100 K to 6500 K. |
| Duration of Exposure | Based on three studies examining the effects of bright light exposure on circadian phase shift, mood and alertness, the duration of exposure is preferably between 12 and 30 minutes to achieve an effect of increased mood, alertness, and phase shifting of about 1-2 hours. Longer exposures may have longer phase shifting effects. |
| Time of Exposure | To phase-advance the circadian rhythm, exposure needs to occur in the morning: "from before a few hours before habitual wake time and for several hours after habitual wake time"; to phase-delay, it needs to occur in the evening: "before bedtime and in the first part of habitual sleep". However, light in the morning is preferably not administered more than one hour before habitual wake time as it could result in phase-delay instead of the desired phase-advance effect. |

The American Academy of Sleep Medicine and the Sleep Research Society recommend at least 7 hours of sleep per night for adults aged 18-60 years old to promote optimal health and well-being. Sleep is one of the body's most critical activities and there are wide ranges of environmental factors that can impact it. For example, noise at night can make it difficult to fall asleep and can create short disturbances of natural sleep patterns by causing shifts from deep to lighter stages. Since most people get the majority of their sleep in their home, a bedroom conducive to healthy and restorative rest requires the creation of a quiet environment. In the bedroom, utilizing materials with a high sound transmission class and high sound reduction index can minimize noise intrusion from outside the bedroom and outside the home. Table 10, below, outlines exemplary specifications for using and manipulating interior wall acoustics in some embodiments.

TABLE 10

| CRITERIA | DEFINITION AND REQUIREMEMNTS |
|---|---|
| Sound Transmission Class (STC) Rating | Interior bedroom walls preferably have an STC rating of 50 or higher. |
| Low VOC Compliance | The interior wall materials preferably meet third party certification low VOC (e.g., Greenguard Gold or Green Tag Certification) requirements. |

Exposure to light at night disrupts the circadian rhythm and leads to melatonin suppression—a key hormone that signals to the body that it is time to go to sleep. Even brief exposures to light at night, especially light that is of short wavelength (in the blue spectrum), can disrupt the sleep-wake cycle, making it hard to fall back to sleep and in turn making it harder to wake up early in the morning. It is therefore essential to provide night lighting that is dim and of a spectrum that minimizes the light in the blue band while providing adequate light levels for safe night time navigation. Table 11, below, outlines exemplary specifications for the use of night lights used in some embodiments.

TABLE 11

Figure 19:
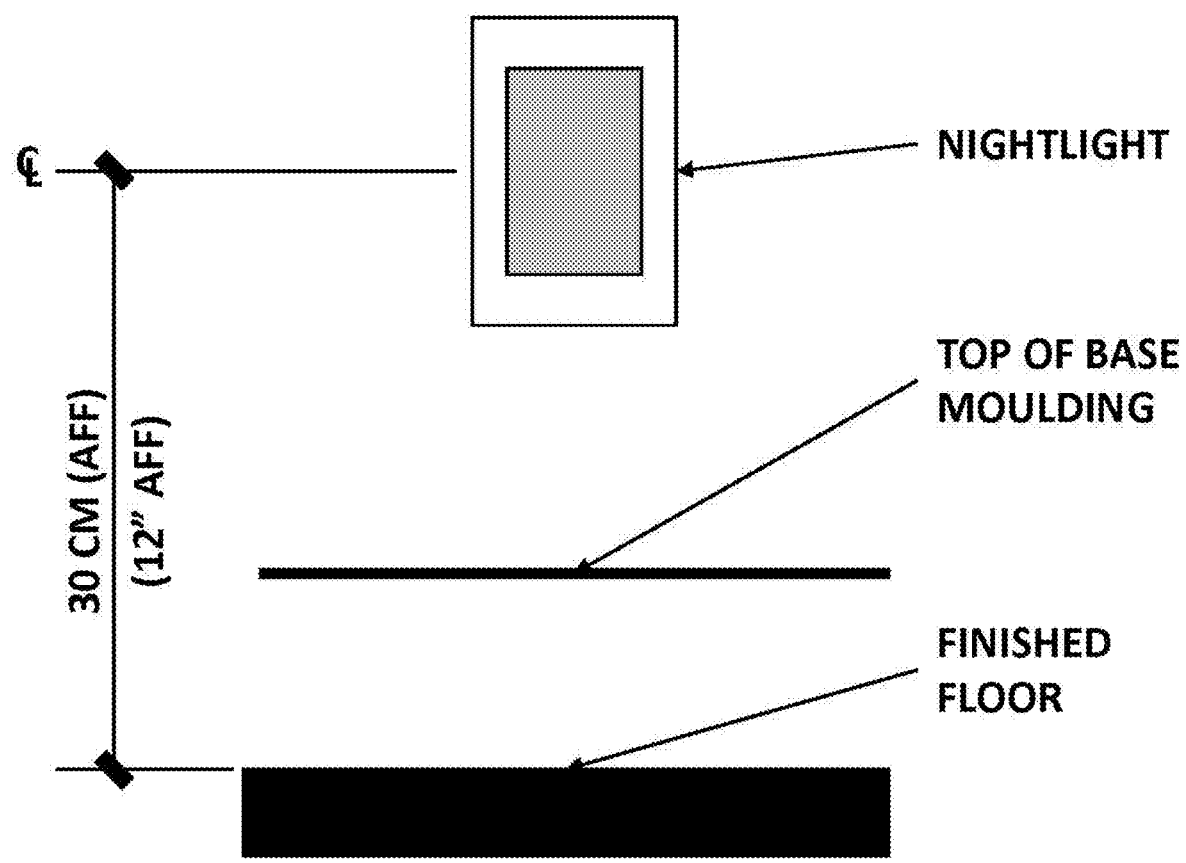
FIG. 19 illustrates the location of a nightlight relative to flooring and moulding.
Figure 20:
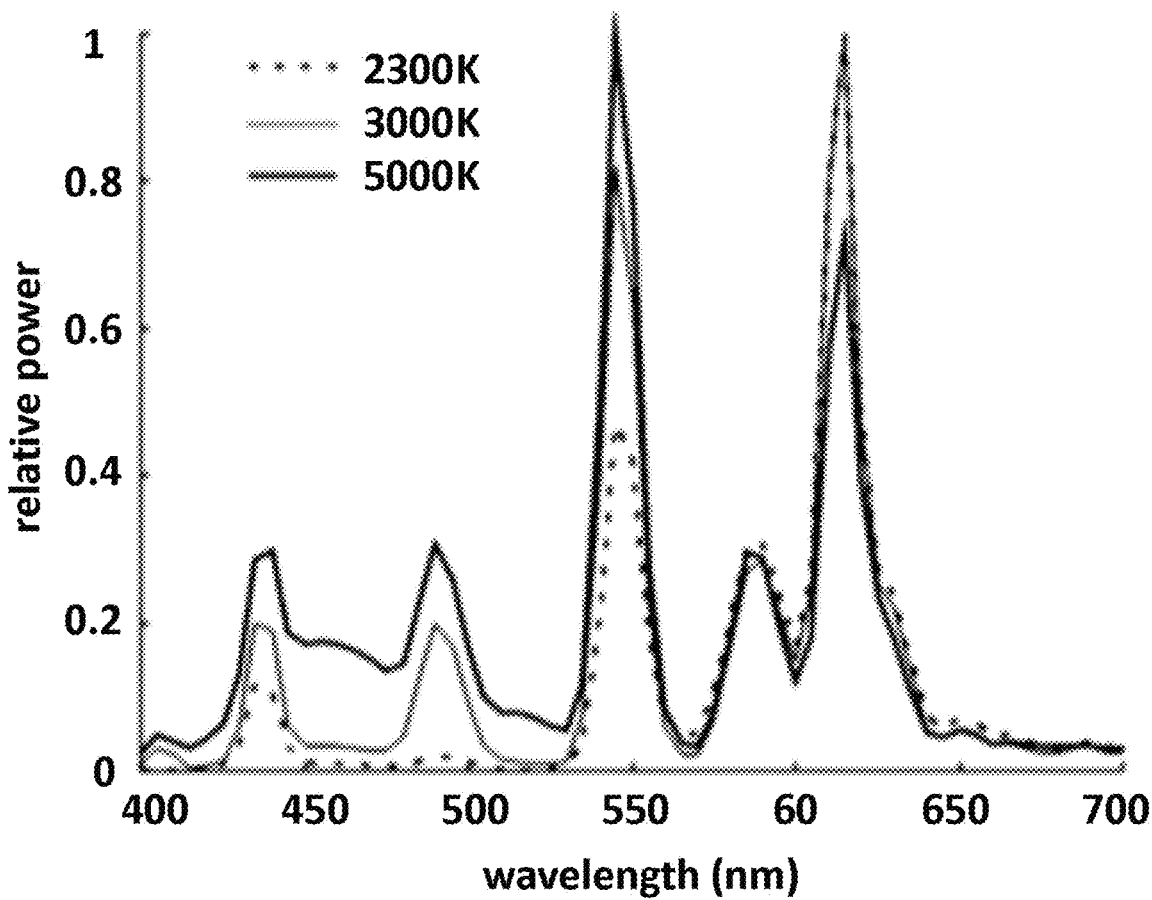
FIG. 20 illustrates the properties of different temperature or CCT of light.

| CRITERIA | DEFINITION AND PARAMETER REQUIREMENTS |
|---|---|
| Light Wavelength | The various types of light that make up the electromagnetic spectrum differ in wavelength. The human circadian system is particularly sensitive to short wavelength light in the blue spectrum, with peak circadian sensitivity at 460-480 nm. At the wavelength of 555 nm and greater, the relative sensitivity to melatonin suppression drops significantly. Therefore, the majority of the spectral power of the night lights are greater than 555 nm, while minimizing the proportion of 460-480 nm band of the spectrum. |
| Illuminance | Illuminance is the amount of light reaching a surface area from the light source and is measured in either lux or foot candles (unit: lux or foot candle; 1 lux = 1 lumen/$m^2$, 1 fc = 1 lumen/$ft^2$). Illuminance below 15 lux (at corneal level in the horizontal angle of gaze) has been found to evoke minimal melatonin phase shift. Therefore, to minimize melatonin suppression and circadian disruption, the illuminance of night lights are preferably below 15 lux, as measured at corneal level in the horizontal angle of gaze. |
| Correlated Color Temperature (CCT) | The CCT of a light source is "a specification of the color appearance of the light emitted by a lamp, relating its color to the color of light from a reference source when heated to a particular temperature, measured in degrees Kelvin (K)". The CCT is 2300-2500 K or lower, since studies using lights with a CCT of 2300-2500 K have demonstrated to have minimal effects on sleep, alertness, and glare. The properties of different CCT of lights are illustrated in FIG. 20. |
| Motion and Light Activated | The night lights are only activated when motion is detected and when the lighting levels in the room are low (below 15 lux, as measured on the vertical of the night light). Alternatively, night lights can be connected to the home automation system and be activated by separate motion or light sensors. |
| Manual Override | A manual override is preferably in place to disable the night light when it is not needed. |
| Installation Location | Location where the night light is installed. The night light is preferably be installed no higher than 30 cm [1 ft] above the floor, without a beam angle above the horizontal plane. FIG. 19 illustrates the location of the night light relative to the floor and moulding. |

Access to water that is clear of inorganic, organic and biological contaminants is essential for maintaining optimal human health. These contaminants, especially in high doses, can be toxic and impair health and overall quality of life. Removal of contaminants can be achieved by installing filters at the point-of-use (assuming the water is mostly potable), most commonly at sink and shower faucets. When selecting a water filter, strict performance criteria must be met to minimize the risks posed by contaminants. Table 12, below, outlines exemplary specifications for the incorporation of point of use water filtration systems used in some embodiments.

TABLE 12

| CRITERIA | DEFINITION AND REQUIREMENTS |
|---|---|
| NSF/ANSI 42 Rated or Equivalent | Testing for aesthetic effects reducing chlorine, taste, odor, and particulates. The product is preferably certified through NSF 42 or testing to the NSF 42 protocol. |
| NSF/ANSI 53 Rated or Equivalent | Reduce specific contaminants including organic volatile impurities (VOIC), biological contaminants, methyl tert-butyl ether (MTBE). Includes material safety, structural |

TABLE 12-continued

| CRITERIA | DEFINITION AND REQUIREMENTS |
|---|---|
| | integrity, and health related contaminants performance. The product is preferably be certified through NSF 53 or tested to the NSF 53 protocol. |
| Micron Rating | The maximum size of openings in a filter media. The point of use is preferably be less than 1 micron (<1 μm in diameter) since this would filter out cryptosporidium and giardia. |
| Flow Rate | Measured in either liters per minute (1 pm) or gallons per minute (gpm), flow rates specify how much water can flow through the specified filter. Depending on the use case, filters have different flow rates. If the goal is not to install a separate faucet for drinking water, the flow rate is preferably be no greater than 2.2 GPM [8.33 LPM]. |
| Pressure | A measure of the force of the water, and is measured in pound-force per square inch (PSI). Measurements are taken when no water is flowing ("static" pressure). The pressure is between 10-125 PSI. |
| Lifetime | The life of the media rated in terms of removal efficiency of a specific chemical. |

The growth and spread of health-threatening biotic agents is a primary concern for moisture buildup in HVAC systems. The use of ultraviolet germicidal irradiation (UVGI) lights installed on the upstream side of the coil in HVAC systems has been associated with a significant reduction in microorganism concentrations on irradiated cooling coils and drip pans. According to a study conducted on office workers, significantly fewer work-related respiratory, mucosal, and overall health symptoms were reported when a UVGI system was used; the use of UVGI also resulted in a 99% reduction in the concentrations of bacteria, fungi, and endotoxins on irradiated surfaces in the HVAC system. Table 13, below, outlines exemplary specifications for the use of UVGI lights used in some embodiments.

TABLE 13

| CRITERIA | DEFINITION AND REQUIREMENTS |
|---|---|
| UVGI Light Wavelength Range | Ultraviolet light in the range of 100-280 nm is the UVC spectrum of radiation. Over 90% of the total spectral power of low-pressure mercury vapor lamps is emitted at 253.7 nm, which is effective in minimizing HVAC system buildup of bacteria, fungi and dust mites. The UVGI lights have at least 90% of their total spectral power distributed at 253.7 (~254) nm. |
| Third Party Testing Conducted | Third party lab testing is preferably used to verify that a company's product effectively reduces microbial concentrations on irradiated cooling coils and drip pans. |
| UVGI Light Lifetime | Lights preferably have a lifetime of at least 1 year before needing to be replaced. |
| No Ozone Production | Ozone is harmful for health and exposure to ozone creates a risk for a variety of symptoms and diseases associated with the respiratory tract; therefore, products are tested and confirmed to emit no ozone. |

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of nontransitory signal bearing media include, but are not limited to, the following: recordable type media such as portable disks and memory, hard disk drives, CD/DVD ROMs, digital tape, computer memory, and other non-transitory computer-readable storage media.

In addition, the sensors used in above can be used to provide other notifications to the user. These include alerts to remind the user to change water filters or air filters, or alerts when a water leak is detected. Alternatively, the system can be programmed to automatically order replacement water filters or air filters when they are needed.

U.S. Provisional Patent Application No. 61/694,125, filed Aug. 28, 2012 and U.S. patent application Ser. No. 14/012,444, filed Aug. 28, 2013 are incorporated herein by reference in their entirety. The various embodiments described above can be combined to provide further embodiments. Aspects of the embodiments can be modified, if necessary or desirable to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for establishing a scene in at least one sub-space associated with a space, comprising the steps of:
   determining a first scene to be implemented in a sub-space during a first period of time based on a first usage occasion, the first usage occasion including at least one of a number of occupants in said sub-space during the first period of time or an activity scheduled to occur in the sub-space during at least a portion the first period of time, the first scene having a lighting parameter setting and an acoustic parameter setting associated therewith;
   sending signals to at least two controllable devices operable in said sub-space;
   implementing said first scene in said sub-space via the at least two controllable devices;
   receiving a signal indicative of a second usage occasion, the second usage occasion including at least one of a number of occupants in said sub-space during a second period of time or a particular activity scheduled to occur in the sub-space during at least a portion of the second period of time; and
   upon receiving said signal indicative of the second usage occasion, implementing a second scene in said sub-space via said at least two controllable devices, the second scene having a lighting parameter setting and an acoustic parameter setting associated therewith; and
   wherein when the number of occupants in said sub-space during the second period of time is greater than the number of occupants in said sub-space during the first period of time, the second scene includes at least one setting specifying a change in at least one of an lighting parameter setting and an acoustic parameter setting in said sub-space in anticipation of the second usage occasion.

2. The method of claim 1, further comprising at least one of:
   determining a current state of at least one environmental parameter for said sub-space;
   receiving a signal indicative of a desired scene to be established in said sub-space;
   receiving a signal indicative of a change to an active scene;
   sending a signal indicative of a desired scene to be established in said sub-space; and
   sending a signal indicative of a change to an active scene.

3. The method of claim 1, further comprising at least one of:
   receiving a signal indicative of a user goal; and
   receiving a signal related to a user.

4. The method of claim 1, further comprising at least one of:
sending a signal indicative of a usage occasion;
sending a signal indicative of a user goal; and
sending a signal related to a user.

5. The method of claim 1, further comprising receiving a signal indicative of an environmental condition associated with said sub-space.

6. The method of claim 1, further comprising sending a signal indicative of an environmental condition associated with said sub-space.

7. The method of claim 1, further comprising sending a signal indicative of an environmental condition external to said sub-space.

8. The method of claim 1, further comprising receiving a signal indicative of a transition from the first scene to the second scene in said sub-space.

9. The method of claim 1, further comprising sending a signal indicative of a transition from the first scene to the second scene in said sub-space.

10. The method of claim 1, further comprising receiving a signal indicative of a change in a default setting associated with said first scene.

11. The method of claim 1, further comprising sending a signal indicative of a change in a default setting associated with said first scene.

12. The method of claim 1 wherein the usage occasion is a particular activity including at least one of personal physical activity, school activity, cognitive activity, work activity, social activity, play, or navigating in a room at night.

13. The method of claim 1 wherein the number of occupants in the sub-space during the first period of time is 1.

14. The method of claim 1 wherein the first scene includes at least one of an energize scene, a relax scene, a play scene, a dawn simulation, and a ready for sleep scene.

15. The method of claim 1 further comprising:
determining a third scene to be implemented in a second sub-space during the first period of time based on a third usage occasion, the third usage occasion including at least one of a number of occupants in said second sub-space during the first period of time or an activity occurring or schedule to occur in the second sub-space during at least a portion the first period of time;
sending a signal to at least one controllable device operable in said second sub-space; and
implementing said third scene in said second sub-space via said at least one controllable device based on said signal.

16. The method of claim 15 further comprising:
receiving a fourth signal indicative of a fourth usage occasion for a second period of time, the fourth usage occasion including at least one of a number of occupants in said second sub-space during the second period of time or a particular activity occurring or scheduled to occur in the second sub-space during at least a portion of the second period of time; and
upon receiving said signal indicative of the second usage occasion, implementing a second scene in said second sub-space via said at least one controllable device.

17. A system comprising:
one or more sensors configured to monitor lighting conditions of a space or sub-space;
one or more controllable devices configured to adjust the lighting conditions of the space or sub-space;
one or more sensors configured to monitor acoustic conditions of the space or sub-space;
one or more controllable devices configured to adjust the acoustic conditions of the space or sub-space;
a scene database with a plurality of scenes therein, each of the scenes having lighting parameter settings and acoustic parameter settings associated therewith, the settings being adjustable in the space or sub-space via the one or more controllable devices;
an electronic user device configured to receive inputs from user regarding a particular one of the scenes; and
a control circuit in communication with the one or more sensors, the one or more controllable devices, the electronic user device, and the scene database, the control circuit configured to:
receive a measurement of the at least one lighting condition and the at least one acoustic condition from the one or more sensors;
receive a scene request from the electronic user device;
instruct the one or more controllable devices to adjust the at least one lighting condition and the at least one acoustic condition of the space or sub-space to render the at least one lighting condition and the at least one acoustic condition within the settings associated with the particular requested scene;
receive notice of or detect a usage occasion for the space or sub-space via the electronic user device; and
change the particular requested scene based on the usage occasion,
wherein the usage occasion is the number of occupants in the space or sub-space or a meeting scheduled to occur in the space or sub-space, and wherein the change in the particular requested scene occurs in advance of the usage occasion, the change in the particular requested scene adjusting a sound masking parameter in anticipation of the usage occasion.

18. The system of claim 17 wherein the change in the particular requested scene also adjusts at least one lighting parameter in anticipation of the usage occasion.

19. The system of claim 17 wherein the scene database further includes scene transition data for transitioning the one or more controllable devices and the environmental conditions of the space or sub-space from a first active scene to a second scene.

20. The system of claim 17, wherein the control circuit is further configured to:
detect a particular condition, the particular condition including at least one of a time of day or external environment factors; and
changing the particular requested scene based, at least in part, on the particular condition.

21. The system of claim 17, wherein each scene has at least one environmental parameter setting configured to govern at least one input device located in the enclosed space to accommodate one or more former, current, or expected occupants of the enclosed space.

22. A system comprising:
one or more sensors configured to monitor lighting conditions of a space or sub-space;
one or more controllable devices configured to adjust the lighting conditions of the space or sub-space;
one or more sensors configured to monitor air quality conditions of the space or sub-space;
one or more controllable devices configured to adjust the air quality conditions of the space or sub-space;
a scene database with a plurality of scenes therein, each of the scenes having lighting parameter settings and air quality parameter settings associated therewith, the settings being adjustable in the space or sub-space via the one or more controllable devices;
an electronic user device configured to receive inputs from a user regarding a particular one of the scenes; and
a control circuit in communication with the one or more sensors, the one or more controllable devices, the electronic user device, and the scene database, the control circuit configured to:
  receive a measurement of the at least one lighting condition and at least one acoustic condition from the one or more sensors;
  receive a scene request from the electronic user device;
  instruct the one or more controllable devices to adjust the at least one lighting condition and the at least one air quality condition of the space or sub-space to render the at least one lighting condition and the at least one air quality condition within the settings associated with the particular requested scene;
  receive notice of or detect a usage occasion for the space or sub-space via the electronic user device, the usage occasion including at least one of a number of occupants in the space or sub-space or a particular activity; and
change the particular requested scene based on the usage occasion,
wherein the sub-space is a conference room and the usage occasion is the number of occupants in the conference room or a meeting scheduled to occur in the conference room, and wherein the change in the particular requested scene occurs in advance of the usage occasion, the change in the particular requested scene adjusting at least one of ventilation or air filtration in anticipation of the usage occasion.

23. A system comprising:
one or more sensors configured to monitor lighting conditions of a space or sub-space;
one or more controllable devices configured to adjust the lighting conditions of the space or sub-space;
one or more sensors configured to monitor air quality conditions of the space or sub-space;
one or more controllable devices configured to adjust the air quality conditions of the space or sub-space;
a scene database with a plurality of scenes therein, each of the scenes having lighting parameter settings and air quality parameter settings associated therewith, the settings being adjustable in the space or sub-space via the one or more controllable devices;
an electronic user device configured to receive inputs from a user regarding a particular one of the scenes; and
a control circuit in communication with the one or more sensors, the one or more controllable devices, the electronic user device, and the scene database, the control circuit configured to:
  receive a measurement of the at least one lighting condition and at least one acoustic condition from the one or more sensors;
  receive a scene request from the electronic user device;
  instruct the one or more controllable devices to adjust the at least one lighting condition and the at least one air quality condition of the space or sub-space to render the at least one lighting condition and the at least one air quality condition within the settings associated with the particular requested scene;
  receive notice of or detect a usage occasion for the space or sub-space via the electronic user device, the usage occasion including at least one of a number of occupants in the space or sub-space or a particular activity; and
change the particular requested scene based on the usage occasion,
wherein the usage occasion is the number of occupants in the space or sub-space or a meeting scheduled to occur in the space or sub-space, and wherein the change in the particular requested scene occurs in advance of the usage occasion, the change in the particular requested scene adjusting at least one of ventilation or air filtration in anticipation of the usage occasion.

24. A system comprising:
one or more controllable devices configured to adjust at least two of a temperature condition, a scent condition, an air quality condition, and an acoustic condition in a space or sub-space;
a control circuit in communication with the one or more controllable devices, the control circuit configured to:
  determine a first scene to be implemented in the space or the sub-space during a first period of time based on a first usage occasion, the first usage occasion including a number of occupants in the space or sub-space during the first period of time, and the first scene including at least one setting specifying an acoustic parameter setting and an air temperature parameter setting in the space or sub-space;
  send signals to at least two controllable devices operable in the space or sub-space;
  implement the first scene in the space or sub-space via the at least two controllable devices;
  receive a signal indicative of a second usage occasion, wherein the second usage occasion includes a number of occupants in the space or sub-space during a second period of time; and
  upon receiving the signal indicative of the second usage occasion, implement a second scene in the space or sub-space via the at least two controllable devices, the second scene having an air temperature parameter setting and an acoustic parameter setting associated therewith;
wherein when the number of occupants in the space or sub-space during the second period of time is greater than the number of occupants in the space or sub-space during the first period of time, the second scene includes at least one setting specifying increased sound masking or decreased air temperature in the space or sub-space.

25. A method for establishing a scene in at least one space or sub-space, comprising the steps of:
receiving a measurement of at least one acoustic condition and at least one air temperature condition from one or more sensors configured to monitor acoustic conditions and air temperature conditions of the at least one space or sub-space;
receiving a scene request from at least one electronic user device configured to receive inputs from a user regarding a particular scene having acoustic parameter and air temperature parameter settings associated therewith, the settings being adjustable in the at least one space or sub-space via one or more controllable devices;
instructing the one or more controllable devices to adjust the at least one acoustic condition and the at least one air temperature condition of the space or sub-space to render the at least one acoustic condition and the at least one air temperature condition within the settings associated with the particular requested scene;

receiving notice of or detecting a usage occasion for the at least one space or sub-space via at least one electronic user device, the usage occasion including at least one of a number of occupants in the at least one space or sub-space or a particular activity; and changing the particular requested scene based on the usage occasion;

wherein the usage occasion is the number of occupants in the space or sub-space or a meeting scheduled to occur in the space or sub-space, and wherein the change in the particular requested scene occurs in advance of the usage occasion, the change in the particular requested scene adjusting acoustics in anticipation of the usage occasion.

* * * * *